(12) United States Patent
Harris et al.

US009668994B2

(10) Patent No.: US 9,668,994 B2
(45) Date of Patent: Jun. 6, 2017

(54) METHODS AND COMPOSITIONS FOR INCREASING THE ANAEROBIC WORKING CAPACITY IN TISSUES

(71) Applicant: Natural Alternatives International, Inc., San Marcos, CA (US)

(72) Inventors: Roger Harris, New Market (GB); Mark Dunnett, Suffolk (GB)

(73) Assignee: Natural Alternatives International, Inc., Carlsbad, CA (US)

( * ) Notice: Subject to any disclaimer, the term of this patent is extended or adjusted under 35 U.S.C. 154(b) by 0 days.

(21) Appl. No.: 14/673,556

(22) Filed: Mar. 30, 2015

(65) Prior Publication Data

US 2016/0051502 A1 Feb. 25, 2016

Related U.S. Application Data

(63) Continuation of application No. 13/900,244, filed on May 22, 2013, now Pat. No. 8,993,610, which is a continuation of application No. 13/356,182, filed on Jan. 23, 2012, now Pat. No. 8,470,865, which is a continuation of application No. 12/806,356, filed on Aug. 10, 2010, now Pat. No. 8,129,422, which is a continuation of application No. 12/231,240, filed on Aug. 29, 2008, now Pat. No. 7,825,084, which is a continuation of application No. 10/717,217, filed on Nov. 18, 2003, now Pat. No. 7,504,376.

(60) Provisional application No. 60/462,238, filed on Apr. 10, 2003.

(51) Int. Cl.
*A61K 31/195* (2006.01)
*A61K 31/197* (2006.01)
*A61K 31/155* (2006.01)
*A61K 31/175* (2006.01)
*A61K 31/198* (2006.01)
*A61K 31/385* (2006.01)
*A61K 31/415* (2006.01)
*A61K 31/44* (2006.01)
*A61K 38/05* (2006.01)
*A61K 38/28* (2006.01)
*A61K 45/06* (2006.01)
*A61K 9/00* (2006.01)
*A23P 10/40* (2016.01)
*A23L 33/175* (2016.01)

(52) U.S. Cl.
CPC .......... *A61K 31/197* (2013.01); *A23L 33/175* (2016.08); *A23P 10/40* (2016.08); *A61K 9/0053* (2013.01); *A61K 31/155* (2013.01); *A61K 31/175* (2013.01); *A61K 31/195* (2013.01); *A61K 31/198* (2013.01); *A61K 31/385* (2013.01); *A61K 31/415* (2013.01); *A61K 31/44* (2013.01); *A61K 38/05* (2013.01); *A61K 38/28* (2013.01); *A61K 45/06* (2013.01); *A23V 2002/00* (2013.01)

(58) Field of Classification Search
CPC ............................ A61K 31/197; A61K 31/155
USPC .................................................. 514/400, 561
See application file for complete search history.

(56) References Cited

U.S. PATENT DOCUMENTS

| | | |
|---|---|---|
| 2,334,163 A | 11/1943 | Kirk |
| 2,336,067 A | 12/1943 | Carlson |
| 2,364,538 A | 12/1944 | Kirk et al. |
| 2,416,630 A | 2/1947 | Kirk |
| 2,734,081 A | 2/1956 | Boatright |
| 3,934,036 A | 1/1976 | Irikura |
| 3,966,988 A | 6/1976 | Wilson et al. |
| 4,120,852 A | 10/1978 | Bauer et al. |
| RE30,370 E | 8/1980 | Pittet et al. |
| 4,761,399 A | 8/1988 | Pilotto et al. |
| 4,833,125 A | 5/1989 | Neer et al. |
| 4,883,861 A | 11/1989 | Grill et al. |
| 5,561,110 A | 10/1996 | Michaelis et al. |
| 5,612,375 A | 3/1997 | Sueoka |
| 5,767,159 A | 6/1998 | Hultman et al. |
| 5,869,068 A | 2/1999 | De Lacharriere et al. |
| 5,965,596 A | 10/1999 | Harris et al. |
| 5,966,457 A | 10/1999 | Lemelson |
| 5,968,544 A | 10/1999 | Howard et al. |
| 5,976,559 A | 11/1999 | De Lacharriere et al. |
| 6,071,888 A | 6/2000 | Rihova et al. |
| 6,168,802 B1 | 1/2001 | Howard et al. |
| 6,172,098 B1 | 1/2001 | Harris et al. |
| 6,274,161 B1 | 8/2001 | Howard et al. |
| 6,426,361 B2 | 7/2002 | Harris et al. |
| 6,524,611 B2 | 2/2003 | Howard et al. |
| 6,680,294 B2 | 1/2004 | Harris et al. |
| 6,855,727 B2 | 2/2005 | Matahira et al. |
| 6,903,136 B2 | 6/2005 | Miller et al. |

(Continued)

FOREIGN PATENT DOCUMENTS

DE 3424781 1/1985
EP 0280593 8/1988

(Continued)

OTHER PUBLICATIONS

In the U.S. Patent and Trademark Office, Office Action in re: U.S. Appl. No. 08/909,513, dated Aug. 31, 1998, 4 pages.

(Continued)

*Primary Examiner* — Raymond Henley, III
(74) *Attorney, Agent, or Firm* — Porzio, Bromberg & Newman P.C.

(57) ABSTRACT

Provided are compositions comprising beta-alanylhistidine peptides and/or beta-alanines, and methods for administering these peptides and amino acids. In one aspect, the compositions and methods cause an increase in the blood plasma concentrations of beta-alanine and/or creatine.

28 Claims, 19 Drawing Sheets

(56) References Cited

U.S. PATENT DOCUMENTS

| | | |
|---|---|---|
| 7,150,880 B2 | 12/2006 | Howard et al. |
| 7,504,376 B2 | 3/2009 | Harris et al. |
| 7,825,084 B2 | 11/2010 | Harris et al. |
| 8,067,381 B1 | 11/2011 | Harris et al. |
| 8,128,955 B2 | 3/2012 | Howard et al. |
| 8,129,422 B2 | 3/2012 | Harris et al. |
| 8,470,865 B2 | 6/2013 | Harris et al. |
| 8,993,610 B2 | 3/2015 | Harris et al. |
| RE45,947 E | 3/2016 | Harris et al. |
| 2004/0229773 A1 | 11/2004 | Harris et al. |
| 2009/0005293 A1 | 1/2009 | Harris et al. |
| 2009/0220575 A1 | 9/2009 | Harris et al. |
| 2011/0009346 A1 | 1/2011 | Harris et al. |

FOREIGN PATENT DOCUMENTS

| | | |
|---|---|---|
| EP | 0449787 A2 | 10/1991 |
| EP | 1210940 A2 | 6/2002 |
| FR | 2658013 | 8/1991 |
| JP | S 54-159393 | 12/1979 |
| JP | 61204120 | 9/1986 |
| JP | S-6442425 | 2/1989 |
| JP | H 0395125 | 4/1991 |
| JP | H 0495026 | 3/1992 |
| JP | H 04112825 | 4/1992 |
| JP | H 0624976 | 2/1994 |
| JP | H 7-236460 | 9/1995 |
| JP | 7509230 | 10/1995 |
| JP | H 8224073 | 9/1996 |
| JP | 2002-51730 | 2/2002 |
| WO | WO-90/06102 A1 | 6/1990 |
| WO | WO-93/04690 A1 | 3/1993 |
| WO | WO-98/06278 A1 | 2/1998 |
| WO | WO-2004/091497 | 10/2004 |

OTHER PUBLICATIONS

In the U.S. Patent and Trademark Office, Notice of Allowance in re: U.S. Appl. No. 08/909,513, dated Apr. 30, 1999, 4 pages.
In the U.S. Patent and Trademark Office, Notice of Allowance in re: U.S. Appl. No. 09/318,530, dated Jul. 20, 2000, 2 pages.
In the U.S. Patent and Trademark Office, Office Action in re: U.S. Appl. No. 10/209,169, dated Mar. 13, 2003.
In the U.S. Patent and Trademark Office, Office Action in re: U.S. Appl. No. 10/209,169, dated Sep. 3, 2003.
In the U.S. Patent and Trademark Office, Notice of Allowance in re: U.S. Appl. No. 10/209,169, dated Oct. 9, 2003.
In the U.S. Patent and Trademark Office, Notice of Allowance in re: U.S. Appl. No. 10/717,217, dated Oct. 30, 2008, 5 pages.
In the U.S. Patent and Trademark Office, Notice of Allowance in re: U.S. Appl. No. 10/717,217, dated Oct. 2, 2008, 6 pages.
In the U.S. Patent and Trademark Office, Notice of Allowance in re: U.S. Appl. No. 10/717,217, dated May 30, 2008. 7 pages.
In the U.S. Patent and Trademark Office, Notice of Allowance in re: U.S. Appl. No. 10/717,217, dated Apr. 25, 2008, 4 pages.
In the U.S. Patent and Trademark Office, Office Action in re: U.S. Appl. No. 10/717,217, dated Sep. 21, 2007, 9 pages.
In the U.S. Patent and Trademark Office, Requirement for Restriction/Election in re: U.S. Appl. No. 10/717,217, dated Jan. 5, 2007, 8 pages.
In the U.S. Patent and Trademark Office, Notice of Allowance in re: U.S. Appl. No. 12/231,240, dated May 25, 2010, 4 pages.
In the U.S. Patent and Trademark Office, Office Action in re: U.S. Appl. No. 12/231,240, dated Oct. 19, 2010, 5 pages.
In the U.S. Patent and Trademark Office, Report on the filing or determination of an action regarding a patent in re: U.S. Appl. No. 12/806,356, dated Jun. 19, 2012, 11 pages.
In the U.S. Patent and Trademark Office, Notice of Allowance in re: U.S. Appl. No. 12/806,356, dated Oct. 21, 2011, 7 pages.
In the U.S. Patent and Trademark Office, Notice of Allowance in re: U.S. Appl. No. 12/806,356, dated Jul. 11, 2011, 1 page.
In the U.S. Patent and Trademark Office, Office Action in re: U.S. Appl. No. 12/806,356, dated May 12, 2011, 5 pages.
In the U.S. Patent and Trademark Office, First Preliminary Amendment in re: U.S. Appl. No. 13/215,073, dated Aug. 22, 2011, 6 pages.
In the U.S. Patent and Trademark Office, Information Disclosure Statement in re: U.S. Appl. No. 13/215,073,dated Aug. 22, 2011, 12 pages.
In the U.S. Patent and Trademark Office, Notice of Allowance in re: U.S. Appl. No. 13/215,073, dated Oct. 17, 2011, 7 pages.
In the U.S. Patent and Trademark Office, Office Action in re: U.S. Appl. No. 13/356,182, dated Aug. 3, 2012, 5 pages.
In the U.S. Patent and Trademark Office, Notice of Allowance in re: U.S. Appl. No. 13/356,182, dated Feb. 22, 2013, 5 pages.
In the U.S. Patent and Trademark Office, Notice of Allowance in re: U.S. Appl. No. 13/900,244, dated Nov. 24, 2014, 8 pages.
In the U.S. Patent and Trademark Office, Final Office Action in re: U.S. Appl. No. 13/900,244, dated Jun. 6, 2014, 5 pages.
In the U.S. Patent and Trademark Office, Office Action in re: U.S. Appl. No. 13/900,244, dated Jul. 24, 2013, 7 pages.
In the U.S. Patent and Trademark Office, Requester Comments on Patent Owner Response after Board Decision in re: U.S. Appl. No. 95/002,001 (Re-Examination of U.S. Pat. No. 8,067,381), dated Sep. 11, 2015, 5 pages.
In the U.S. Patent and Trademark Office, Reexam Petition Decision—Dismissed in re: U.S. Appl. No. 95/002,001 (Re-Examination of U.S. Pat. No. 8,067,381), dated Aug. 28, 2015, 5 pages.
In the U.S. Patent and Trademark Office, Request for rehearing to Patent Board in re: U.S. Appl. No. 95/002,001 (Re-Examination of U.S. Pat. No. 8,067,381), dated Aug. 31, 2015, 8 pages.
In the U.S. Patent and Trademark Office, Patent Board Decision—Examiner Affirmed in re: U.S. Appl. No. 95/002,001 (Re-Examination of U.S. Pat. No. 8,067,381), dated Jul. 17, 2015, 33 pages.
In the U.S. Patent and Trademark Office, Reexam Petition Decision—Dismissed in re: U.S. Appl. No. 95/002,001 (Re-Examination of U.S. Pat. No. 8,067,381), dated May 21, 2015, 3 pages.
In the U.S. Patent and Trademark Office, Reexam Petition Letter Acknowledging That an Improper Paper in a Reexam Proceeding Has Been Returned/Destroyed in re: U.S. Appl. No. 95/002,001 (Re-Examination of U.S. Pat. No. 8,067,381), dated May 19, 2015, 11 pages.
In the U.S. Patent and Trademark Office, Reexam Petition Letter Acknowledging That an Improper Paper in a Reexam Proceeding Has Been Returned/Destroyed in re: U.S. Appl. No. 95/002,001 (Re-Examination of U.S. Pat. No. 8,067,381), dated May 7, 2015, 8 pages.
In the U.S. Patent and Trademark Office, Transcript Record of Oral Hearing held Apr. 15, 2015 in re: U.S. Appl. No. 95/002,001 (Re-Examination of U.S. Pat. No. 8,067,381), mailed May 1, 2015, 51 pages.
In the U.S. Patent and Trademark Office, Reexam—Opposition filed in response to petition in re: U.S. Appl. No. 95/002,001 (Re-Examination of U.S. Pat. No. 8,067,381), dated Apr. 14, 2015, 5 pages.
In the U.S. Patent and Trademark Office, Reexam—Opposition filed in response to petition in re: U.S. Appl. No. 95/002,001 (Re-Examination of U.S. Pat. No. 8,067,381), dated Apr. 10, 2015, 5 pages.
In the U.S. Patent and Trademark Office, Petition Entered in re: U.S. Appl. No. 95/002,001 (Re-Examination of U.S. Pat. No. 8,067,381), dated Apr. 7, 2015, 8 pages.
In the U.S. Patent and Trademark Office, Petition under Rule 41.3 to Chief Admin Patent Judge in re: U.S. Appl. No. 95/002,001 (Re-Examination of U.S. Pat. No. 8,067,381), dated Apr. 7, 2015, 7 pages.
In the U.S. Patent and Trademark Office, Reexam Petition Letter Acknowledging That an Improper Paper in a Reexam Proceeding Has Been Returned/Destroyed in re: U.S. Appl. No. 95/002,001 (Re-Examination of U.S. Pat. No. 8,067,381), dated Apr. 3, 2015, 24 pages.
In the U.S. Patent and Trademark Office, Hearing Postponement Denied in re: U.S. Appl. No. 95/002,001 (Re-Examination of U.S. Pat. No. 8,067,381), dated Mar. 31, 2015, 5 pages.

(56) References Cited

OTHER PUBLICATIONS

In the U.S. Patent and Trademark Office, Reexam—Miscellaneous Action in re: U.S. Appl. No. 95/002,001 (Re-Examination of U.S. Pat. No. 8,067,381), dated Mar. 31, 2015, 5 pages.
In the U.S. Patent and Trademark Office, Reexam—Miscellaneous Action in re: U.S. Appl. No. 95/002,001 (Re-Examination of U.S. Pat. No. 8,067,381), dated Mar. 30, 2015, 4 pages.
In the U.S. Patent and Trademark Office, Appeal to CAFC in re: U.S. Appl. No. 95/002,001 (Re-Examination of U.S. Pat. No. 8,067,381), dated Feb. 2, 2015, 2 pages.
In the U.S. Patent and Trademark Office, Notification of Appeal Hearing in re: U.S. Appl. No. 95/002,001 (Re-Examination of U.S. Pat. No. 8,067,381), dated Jan. 13, 2015, 4 pages.
In the U.S. Patent and Trademark Office, Appeal Docketing Notice in re: U.S. Appl. No. 95/002,001 (Re-Examination of U.S. Pat. No. 8,067,381), dated Oct. 9, 2014, 3 pages.
In the U.S. Patent and Trademark Office, Appeal Docketing Notice in re: U.S. Appl. No. 95/002,001 (Re-Examination of U.S. Pat. No. 8,067,381), dated Oct. 9, 2014, 5 pages.
In the U.S. Patent and Trademark Office, Oral Hearing Request—Owner in re: U.S. Appl. No. 95/002,001 (Re-Examination of U.S. Pat. No. 8,067,381), dated Sep. 30, 2014, 2 pages.
In the U.S. Patent and Trademark Office, Rebuttal Brief—Owner in re: U.S. Appl. No. 95/002,001 (Re-Examination of U.S. Pat. No. 8,067,381), dated Sep. 2, 2014, 14 pages.
In the U.S. Patent and Trademark Office, Examiner's Answer to Appeal Brief in re: U.S. Appl. No. 95/002,001 (Re-Examination of U.S. Pat. No. 8,067,381), dated Jul. 31, 2014, 3 pages.
In the U.S. Patent and Trademark Office, Respondent Brief—Requester in re: U.S. Appl. No. 95/002,001 (Re-Examination of U.S. Pat. No. 8,067,381), dated Jun. 13, 2014, 26 pages.
In the U.S. Patent and Trademark Office, Appeal Brief—Owner in re: U.S. Appl. No. 95/002,001 (Re-Examination of U.S. Pat. No. 8,067,381), dated May 14, 2014, 363 pages.
In the U.S. Patent and Trademark Office, Reexam Petition Letter Acknowledging That an Improper Paper in a Reexam Proceeding Has Been Returned/Destroyed in re: U.S. Appl. No. 95/002,001 (Re-Examination of U.S. Pat. No. 8,067,381), dated May 5, 2014, 4 pages.
In the U.S. Patent and Trademark Office, Reexam Petition Decision—Dismissed in re: U.S. Appl. No. 95/002,001 (Re-Examination of U.S. Pat. No. 8,067,381), dated Apr. 30, 2014, 8 pages.
In the U.S. Patent and Trademark Office, Reexam—Opposition filed in response to petition in re: U.S. Appl. No. 95/002,001 (Re-Examination of U.S. Pat. No. 8,067,381), dated Mar. 6, 2014, 3 pages.
In the U.S. Patent and Trademark Office, Reexam Petition Decision—Granted-in-Part in re: U.S. Appl. No. 95/002,001 (Re-Examination of U.S. Pat. No. 8,067,381), dated Mar. 6 2014, 4 pages.
In the U.S. Patent and Trademark Office, Petition decided by Patent Legal Administration in response to petition in re: U.S. Appl. No. 95/002,001 (Re-Examination of U.S. Pat. No. 8,067,381), dated Mar. 4, 2014, 4 pages.
In the U.S. Patent and Trademark Office, Reexam—Opposition filed in response to petition in re: U.S. Appl. No. 95/002,001 (Re-Examination of U.S. Pat. No. 8,067,381), dated Jan. 7, 2014, 8 pages.
In the U.S. Patent and Trademark Office, Reexam Petition Decision—Dismissed in re: U.S. Appl. No. 95/002,001 (Re-Examination of U.S. Pat. No. 8,067,381), dated Dec. 31, 2013, 8 pages.
In the U.S. Patent and Trademark Office, Receipt of Petition in a Reexam in a Reexam Proceeding Has Been Returned/Destroyed in re: U.S. Appl. No. 95/002,001 (Re-Examination of U.S. Pat. No. 8,067,381), dated Dec. 24, 2013, 7 pages.
In the U.S. Patent and Trademark Office, Right of Appeal Notice in re: U.S. Appl. No. 95/002,001 (Re-Examination of U.S. Pat. No. 8,067,381), dated Dec. 6, 2013, 38 pages.
In the U.S. Patent and Trademark Office, Reexam Petition Decision—Dismissed in re: U.S. Appl. No. 95/002,001 (Re-Examination of U.S. Pat. No. 8,067,381), dated Nov. 15, 2013, 3 pages.
In the U.S. Patent and Trademark Office, Reexam—Opposition filed in response to petition in re: U.S. Appl. No. 95/002,001 (Re-Examination of U.S. Pat. No. 8,067,381), dated Nov. 1, 2013, 8 pages.
In the U.S. Patent and Trademark Office, Receipt of Petition in a Reexam in re: U.S. Appl. No. 95/002,001 (Re-Examination of U.S. Pat. No. 8,067,381), dated Oct. 15, 2013, 4 pages.
In the U.S. Patent and Trademark Office, Notice of concurrent proceedings/decisions in re: U.S. Appl. No. 95/002,001 (Re-Examination of U.S. Pat. No. 8,067,381), dated Aug. 23, 2013, 3 pages.
In the U.S. Patent and Trademark Office, Reexam Petition Decision—Dismissed in re: U.S. Appl. No. 95/002,001 (Re-Examination of U.S. Pat. No. 8,067,381), dated Jul. 10, 2013, 4 pages.
In the U.S. Patent and Trademark Office, Reexam—Opposition filed in response to petition in re: U.S. Appl. No. 95/002,001 (Re-Examination of U.S. Pat. No. 8,067,381), dated Apr. 4, 2013, 13 pages.
In the U.S. Patent and Trademark Office, Receipt of Petition in a Reexam in re: U.S. Appl. No. 95/002,001 (Re-Examination of U.S. Pat. No. 8,067,381), dated Mar. 21, 2013, 6 pages.
In the U.S. Patent and Trademark Office, Reexam—Opposition filed in response to petition in re: U.S. Appl. No. 95/002,001 (Re-Examination of U.S. Pat. No. 8,067,381), dated Dec. 28, 2012, 19 pages.
In the U.S. Patent and Trademark Office, Receipt of Petition in a Reexam in re: U.S. Appl. No. 95/002,001 (Re-Examination of U.S. Pat. No. 8,067,381), dated Dec. 14, 2012, 10 pages.
In the U.S. Patent and Trademark Office, Response after Non-Final Action—owner timely in re: U.S. Appl. No. 95/002,001 (Re-Examination of U.S. Pat. No. 8,067,381), dated Dec. 12, 2012, 33 pages.
In the U.S. Patent and Trademark Office, Third Party Requester Comments after Non-Final Action in re: U.S. Appl. No. 95/002,001 (Re-Examination of U.S. Pat. No. 8,067,381), dated Nov. 28, 2012, 49 pages.
In the U.S. Patent and Trademark Office, Notification of Defective Paper in a Reexam in re: U.S. Appl. No. 95/002,001 (Re-Examination of U.S. Pat. No. 8,067,381), dated Nov. 13, 2012, 4 pages.
In the U.S. Patent and Trademark Office, Response after Non-Final Office Action—owner timely in re: U.S. Appl. No. 95/002,001 (Re-Examination of U.S. Pat. No. 8,067,381), dated Oct. 29, 2012, 33 pages.
In the U.S. Patent and Trademark Office, Reexam Extension of Time Period for Response Granted in re: U.S. Appl. No. 95/002,001 (Re-Examination of U.S. Pat. No. 8,067,381), dated Oct. 26, 2012, 3 pages.
In the U.S. Patent and Trademark Office, Reexam Request for Extension of Time in re: U.S. Appl. No. 95/002,001 (Re-Examination of U.S. Pat. No. 8,067,381), dated Oct. 25, 2012, 5 pages.
In the U.S. Patent and Trademark Office, Reexam Petition Decision—Granted—in—part in re: U.S. Appl. No. 95/002,001 (Re-Examination of U.S. Pat. No. 8,067,381), dated Sep. 19, 2012, 3 pages.
In the U.S. Patent and Trademark Office, Reexam Request for Extension of Time in re: U.S. Appl. No. 95/002,001 (Re-Examination of U.S. Pat. No. 8,067,381), dated Sep. 17, 2012, 7 pages.
In the U.S. Patent and Trademark Office, Order Granting Request for Inter Partes Reexamination in re: U.S. Appl. No. 95/002,001 (Re-Examination of U.S. Pat. No. 8,067,381), dated Jul. 26, 2012, 19 pages.
In the U.S. Patent and Trademark Office, Reexam Non-Final Office Action in re: U.S. Appl. No. 95/002,001 (Re-Examination of U.S. Pat. No. 8,067,381), dated Jul. 26, 2012, 19 pages.
In the U.S. Patent and Trademark Office, Reexam Litigation Search Conducted in re: U.S. Appl. No. 95/002,001 (Re-Examination of U.S. Pat. No. 8,067,381), dated Jun. 7, 2012, 33 pages.
In the U.S. Patent and Trademark Office, Reexam Miscellaneous Incoming Letter by third party requester in re: U.S. Appl. No. 95/002,001 (Re-Examination of U.S. Pat. No. 8,067,381), dated Jun. 7, 2012, 33 pages.

(56) References Cited

OTHER PUBLICATIONS

In the U.S. Patent and Trademark Office, Receipt of Original Inter Partes Reexam Request in re: U.S. Appl. No. 95/002,001 (Re-Examination of U.S. Pat. No. 8,067,381), dated May 31, 2012, 40 pages.
In the U.S. Patent and Trademark Office, Inter Partes Reexamination, for U.S. Pat. No. 8,067,381, Reexam Office Action in re: Reexam Application No. 95/002,001, dated Jul. 26, 2012, 19 pages.
In the U.S. Patent and Trademark Office, Inter Partes Reexamination, for U.S. Pat. No. 8,067,381, Determination—Reexam Ordered in re: Reexam Application No. 95/002,001, dated Jul. 26, 2012, 19 pages.
In the U.S. Patent and Trademark Office, Inter Partes Reexamination, for U.S. Pat. No. 8,067,381, Patent Owner response to Non-Final Action in re: Reexam Application No. 95/002,001, dated Dec. 12, 2012, 33 pages.
In the U.S. Patent and Trademark Office, Inter Partes Reexamination, for U.S. Pat. No. 8,067,381, Third Party Requester Comments after Non-Final Action in re: Reexam Application No. 95/002,001, dated Nov. 28, 2012, 49 pages.
In the U.S. Patent and Trademark Office, Inter Partes Reexamination, for U.S. Pat. No. 8,067,381, Patent Owner response to Non-Final Action in re: Reexam Application No. 95/002,001, dated Oct. 29, 2012, 33 pages.
In the U.S. Patent and Trademark Office, Confirmation of Hearing by Appellant in re: U.S. Appl. No. 95/002,048 (Re-Examination of U.S. Pat. No. 8,129,422), dated Jan. 29, 2016, 3 pages.
In the U.S. Patent and Trademark Office, Oral Hearing Request—Third Party Requester in re: U.S. Appl. No. 95/002,048 (Re-Examination of U.S. Pat. No. 8,129,422), dated Jan. 29, 2016, 4 pages.
In the U.S. Patent and Trademark Office, Notification of Appeal Hearing in re: U.S. Appl. No. 95/002,048 (Re-Examination of U.S. Pat. No. 8,129,422), dated Jan. 13, 2016, 4 pages.
In the U.S. Patent and Trademark Office, Reexam Petition Decision—Denied in re: U.S. Appl. No. 95/002,048 (Re-Examination of U.S. Pat. No. 8,129,422), dated Sep. 14, 2015, 12 pages.
In the U.S. Patent and Trademark Office, Inter Partes Reexamination, for U.S. Pat. No. 8,067,381, Notice of concurrent proceedings/decisions in re: Reexam Application No. 95/002,048, dated Jul. 29, 2015, 37 pages.
In the U.S. Patent and Trademark Office, Inter Partes Reexamination, for U.S. Pat. No. 8,067,381, Reexam—Opposition filed in response to petition in re: Reexam Application No. 95/002,048, dated May 8, 2015, 5 pages.
In the U.S. Patent and Trademark Office, Improper Paper in a Reexam Proceeding Has Been Returned/Destroyed in re: U.S. Appl. No. 95/002,048 (Re-Examination of U.S. Pat. No. 8,129,422), dated May 7, 2015, 8 pages.
In the U.S. Patent and Trademark Office, Inter Partes Reexamination, for U.S. Pat. No. 8,067,381, Reexam—Opposition filed in response to petition in re: Reexam Application No. 95/002,048, dated Apr. 24, 2015, 5 pages.
In the U.S. Patent and Trademark Office, Inter Partes Reexamination, for U.S. Pat. No. 8,067,381, Reexam—Opposition filed in response to petition in re: Reexam Application No. 95/002,048, dated Apr. 21, 2015, 8 pages.
In the U.S. Patent and Trademark Office, Inter Partes Reexamination, for U.S. Pat. No. 8,067,381, Receipt of Petition in a Reexam in re: Reexam Application No. 95/002,048, dated Apr. 9, 2015, 6 pages.
In the U.S. Patent and Trademark Office, Inter Partes Reexamination, for U.S. Pat. No. 8,067,381, Receipt of Petition in a Reexam in re: Reexam Application No. 95/002,048, dated Apr. 2, 2015, 2 pages.
In the U.S. Patent and Trademark Office, Inter Partes Reexamination, for U.S. Pat. No. 8,067,381, Request for Oral Hearing in re: Reexam Application No. 95/002,048, dated Mar. 27, 2015, 2 pages.
In the U.S. Patent and Trademark Office, Inter Partes Reexamination, for U.S. Pat. No. 8,067,381, Rebuttal Brief—Owner in re: Reexam Application No. 95/002,048, dated Mar. 27, 2015, 14 pages.
In the U.S. Patent and Trademark Office, Inter Partes Reexamination, for U.S. Pat. No. 8,067,381, Reexam Petition Decision—Dismissed in re: Reexam Application No. 95/002,048, dated Mar. 12, 2015, 10 pages.
In the U.S. Patent and Trademark Office, Inter Partes Reexamination, for U.S. Pat. No. 8,067,381, Examiner's Answer to Appeal Brief in re: Reexam Application No. 95/002,048, dated Feb. 27, 2015, 4 pages.
In the U.S. Patent and Trademark Office, Inter Partes Reexamination, for U.S. Pat. No. 8,067,381, Appeal Brief—Owner in re: Reexam Application No. 95/002,048, Feb. 27, 2015, 46 pages.
In the U.S. Patent and Trademark Office, Inter Partes Reexamination, for U.S. Pat. No. 8,067,381, Respondent Brief—Requester in re: Reexam Application No. 95/002,048, Feb. 5, 2015, 22 pages.
In the U.S. Patent and Trademark Office, Inter Partes Reexamination, for U.S. Pat. No. 8,067,381, Notice—Defective Brief in Reexam in re: Reexam Application No. 95/002,048, Jan. 30, 2015, 7 pages.
In the U.S. Patent and Trademark Office, Inter Partes Reexamination, for U.S. Pat. No. 8,067,381, Appeal Brief—Owner in re: Reexam Application No. 95/002,048, Jan. 6, 2015, 45 pages.
In the U.S. Patent and Trademark Office, Inter Partes Reexamination, for U.S. Pat. No. 8,067,381, Reexam Petition Decision—Denied in re: Reexam Application No. 95/002,048, Jan. 6, 2015, 9 pages.
In the U.S. Patent and Trademark Office, Inter Partes Reexamination, for U.S. Pat. No. 8,067,381, Reexam—Opposition filed in response to petition in re: Reexam Application No. 95/002,048, Nov. 19, 2014, 9 pages.
In the U.S. Patent and Trademark Office, Inter Partes Reexamination, for U.S. Pat. No. 8,067,381, Reexam Petition Decision—Granted-in-Part in re: Reexam Application No. 95/002,048, Nov. 6, 4 pages.
In the U.S. Patent and Trademark Office, Inter Partes Reexamination, for U.S. Pat. No. 8,067,381, Receipt of Petition in Reexam in re: Reexam Application No. 95/002,048, Nov. 4, 2014, 5 pages.
In the U.S. Patent and Trademark Office, Inter Partes Reexamination, for U.S. Pat. No. 8,067,381, Receipt of Petition in Reexam in re: Reexam Application No. 95/002,048, Nov. 4, 2014, 26 pages.
In the U.S. Patent and Trademark Office, Inter Partes Reexamination, for U.S. Pat. No. 8,067,381, Receipt of Petition in Reexam in re: Reexam Application No. 95/002,048, Nov. 4, 2014, 24 pages.
In the U.S. Patent and Trademark Office, Inter Partes Reexamination, for U.S. Pat. No. 8,067,381, Notice of Appeal Filed in re: Reexam Application No. 95/002,048, Sep. 8, 2014, 1 page.
In the U.S. Patent and Trademark Office, Inter Partes Reexamination, for U.S. Pat. No. 8,067,381, Right of Appeal Notice in re: Reexam Application No. 95/002,048, Aug. 8, 2014, 70 pages.
In the U.S. Patent and Trademark Office, Inter Partes Reexamination, for U.S. Pat. No. 8,067,381, Reexam Petition Decision—Dismissed in re: Reexam Application No. 95/002,048, dated Dec. 31, 2013, 8 pages.
In the U.S. Patent and Trademark Office, Inter Partes Reexamination, for U.S. Pat. No. 8,067,381, Third Party Requester Comments after Action Closing Prosecution in re: Reexam Application No. 95/002,048, dated Nov. 25, 2013, 25 pages.
In the U.S. Patent and Trademark Office, Inter Partes Reexamination, for U.S. Pat. No. 8,067,381, Affidavit submitted prior to Mar. 15, 2013 in re: Reexam Application No. 95/002,048, dated Oct. 30, 2013, 19 pages.
In the U.S. Patent and Trademark Office, Inter Partes Reexamination, for U.S. Pat. No. 8,067,381, Affidavit submitted prior to Mar. 15, 2013 in re: Reexam Application No. 95/002,048, dated Oct. 30, 2013, 20 pages.
In the U.S. Patent and Trademark Office, Notice of concurrent proceedings/decisions in re: U.S. Appl. No. 95/002,048 (Re-Examination of U.S. Pat. No. 8,129,422), dated Oct. 30, 2013, 4 pages.

(56) References Cited

OTHER PUBLICATIONS

In the U.S. Patent and Trademark Office, Patent Owner Comments after Action Closing Prosecution in re: U.S. Appl. No. 95/002,048 (Re-Examination of U.S. Pat. No. 8,129,422), dated Oct. 30, 2013, 40 pages.
In the U.S. Patent and Trademark Office, Action Closing Prosecution (nonfinal) in re: U.S. Appl. No. 95/002,048 (Re-Examination of U.S. Pat. No. 8,129,422), dated Sep. 30, 2013, 62 pages.
In the U.S. Patent and Trademark Office, Inter Partes Reexamination, for U.S. Pat. No. 8,067,381, Affidavit submitted prior to Mar. 15, 2013 in re: Reexam Application No. 95/002,048, dated Sep. 27, 2013, 21 pages.
In the U.S. Patent and Trademark Office, Action Closing Prosecution (nonfinal) in re: U.S. Appl. No. 95/002,048 (Re-Examination of U.S. Pat. No. 8,129,422), dated Sep. 19, 2013, 61 pages.
In the U.S. Patent and Trademark Office, Reexam Petition Decision—Dismissed in re: U.S. Appl. No. 95/002,048 (Re-Examination of U.S. Pat. No. 8,129,422), dated Jun. 4, 2013, 3 pages.
In the U.S. Patent and Trademark Office, Reexam—Opposition filed in resopnse to petition in re: U.S. Appl. No. 95/002,048 (Re-Examination of U.S. Pat. No. 8,129,422), dated Apr. 4, 2013, 13 pages.
In the U.S. Patent and Trademark Office, Receipt of Petition in a Reexam in re: U.S. Appl. No. 95/002,048 (Re-Examination of U.S. Pat. No. 8,129,422), dated Mar. 21, 2013, 6 pages.
In the U.S. Patent and Trademark Office, Reexam Peition Decision—Dismissed in re: U.S. Appl. No. 95/002,048 (Re-Examination of U.S. Pat. No. 8,129,422), dated Mar. 13, 2013, 6 pages.
In the U.S. Patent and Trademark Office, Reexam—Opposition filed in resopnse to petition in re: U.S. Appl. No. 95/002,048 (Re-Examination of U.S. Pat. No. 8,129,422), dated Mar. 7, 2013, 19 pages.
In the U.S. Patent and Trademark Office, Receipt of Petition in a Reexam in re: U.S. Appl. No. 95/002,048 (Re-Examination of U.S. Pat. No. 8,129,422), dated Feb. 21, 2013, 12 pages.
In the U.S. Patent and Trademark Office, Third Party Requester Comments after Non-Final Office Action in re: U.S. Appl. No. 95/002,048 (Re-Examination of U.S. Pat. No. 8,129,422), dated Jan. 16, 2013, 48 pages.
In the U.S. Patent and Trademark Office, Response after Non-Final Office Action—owner timely in re: U.S. Appl. No. 95/002,048 (Re-Examination of U.S. Pat. No. 8,129,422), dated Dec. 17, 2012, 36 pages.
In the U.S. Patent and Trademark Office, Reexam Non-Final Office Action in re: U.S. Appl. No. 95/002,048 (Re-Examination of U.S. Pat. No. 8,129,422), dated Dec. 17, 2012, 36 pages.
In the U.S. Patent and Trademark Office, Receipt of Petition in a Reexam in re: U.S. Appl. No. 95/002,048 (Re-Examination of U.S. Pat. No. 8,129,422), dated Sep. 25, 2012, 9 pages.
In the U.S. Patent and Trademark Office, Determination—Reexam Ordered in re: U.S. Appl. No. 95/002,048 (Re-Examination of U.S. Pat. No. 8,129,422), dated Aug. 17, 2012, 22 pages.
In the U.S. Patent and Trademark Office, Reexam—Non-Final Office Action in re: U.S. Appl. No. 95/002,048 (Re-Examination of U.S. Pat. No. 8,129,422), dated Aug. 17, 2012, 24 pages.
In the U.S. Patent and Trademark Office, Reexam Litigation Search Conducted in re: U.S. Appl. No. 95/002,048 (Re-Examination of U.S. Pat. No. 8,129,422), dated Aug. 13, 2012, 18 pages.
In the U.S. Patent and Trademark Office, Reexam Litigation Search Conducted in re: U.S. Appl. No. 95/002,048 (Re-Examination of U.S. Pat. No. 8,129,422), dated Jul. 25, 2012, 43 pages.
In the U.S. Patent and Trademark Office, Receipt of Original Inter Partes Reexam Request in re: U.S. Appl. No. 95/002,048 (Re-Examination of U.S. Pat. No. 8,129,422), dated Jul. 19, 2012, 40 pages.
In the U.S. Patent and Trademark Office, Inter Partes Reexamination for U.S. Pat. No. 8,129,422, Reexam Office Action in re: Reexam Application No. 95/002,048, dated Oct. 16, 2012, 28 pages.
In the U.S. Patent and Trademark Office, Inter Partes Reexamination for U.S. Pat. No. 8,129,422, Determination—Reexam Ordered in re: Reexam Application No. 95/002,048, dated Aug. 17, 2012, 22 pages.
In the U.S. Patent and Trademark Office, Inter Partes Reexamination for U.S. Pat. No. 8,129,422, Reexam Office Action in re: Reexam Application No. 95/002,048, dated Aug. 17, 2012, 24 pages.
In the U.S. Patent and Trademark Office, Inter Partes Reexamination for U.S. Pat. No. 8,129,422, Third Party Requester Comments after Non-Final Action in re: Reexam Application No. 95/002,048, dated Jan. 16, 2013, 48 pages.
In the U.S. Patent and Trademark Office, Inter Partes Reexamination for U.S. Pat. No. 8,129,422, Patent Owner response to Non-Final Action in re: Reexam Application No. 95/002,048, dated Dec. 17, 2012, 36 pages.
In the U.S. Patent and Trademark Office, Inter Partes Reexamination for U.S. Pat. No. 8,129,422, Affidavit submitted prior to Mar. 15, 2013 in re: Reexam Application No. 95/002,048, dated Dec. 17, 2012, 21 pages.
In the U.S. Patent and Trademark Office, Office Action in re: U.S. Appl. No. 14/189,198, dated Dec. 12, 2014, 14 pages.
In the U.S. Patent and Trademark Office, Notice of Allowance in re: U.S. Appl. No. 14/189,198, dated Feb. 1, 2016, 6 pages.
In the U.S. Patent and Trademark Office, Final Office Action in re: U.S. Appl. No. 14/189,198, dated Dec. 24, 2015, 13 pages.
*DNP International Co. Inc. v. Natural Alternatives International Inc. et al*, filed Dec. 22, 2011, U.S. District Court District of Delaware (Wilmington) Civil Docket for Case #: 1:11-cv-01283-GMS; Amended Complaint against Compound Solutions Inc., Natural Alternatives International Inc.—filed by DNP International Co. Inc . . . (Attachments: # I Exhibits A through C, # 2 Exhibit D, # I Patent/Trademark Report)(Russell, Andrew) (Entered: Jan. 27, 2012).
*DNP International Co. Inc. v. Natural Alternatives International Inc. et al*, filed Dec. 22, 2011, U.S. District Court District of Delaware (Wilmington) Civil Docket for Case #: 1:11-cv-01283-GMS; Answer to 17 Answer to Amended Complaint, Counterclaim Plaintiff DNP International Co., Inc.'s Answer to Natural Alternatives International, Inc.'s Counterclaim and Affirmative Defenses by DNP International Co. Inc . . . (Keller, Karen) (Entered: Feb. 27, 2012).
*DNP International Co. Inc. v. Natural Alternatives International Inc. et al*, filed Dec. 22, 2011, U.S. District Court District of Delaware (Wilmington) Civil Docket for Case #: 1:11-cv-01283-GMS; Answer to Amended Complaint Answer to 11 Amended Complaint with Jury Demand, Counterclaim against DNP International Co. Inc. By Natural Alternatives International Inc . . . (Attachments: # 1 Exhibit 1-6)(Moore, David) (Entered: Feb. 6, 2012).
*DNP International Co. Inc. v. Natural Alternatives International Inc. et al*, filed Dec. 22, 2011, U.S. District Court District of Delaware (Wilmington) Civil Docket for Case #: 1:11-cv-01283-GMS; Complaint for Declaratory Judgment filed with Jury Demand against Compound Solutions Inc., Natural Alternatives International Inc.—Magistrate Consent Notice to Pltf. ( Filing fee $350, receipt No. 0311-997358.)—filed by DNP International Co. Inc . . . (Attachments: # 1 Exhibit A, # 2 Exhibit B, # 3 Exhibit C, # 4 Civil Cover Sheet)(dzs,) (Entered: Dec. 23, 2011).
*Natural Alternatives International Inc. v. Vital Pharmaceuticals Inc. et al*, filed Aug. 20, 2009, U.S. District Court District of Delaware (Wilmington) Civil Docket for Case #: 1:09-cv-00626-GMS; Claim Construction Answering Brief re 76 Claim Construction Opening Brief Defendants' Answering Claim Construction Brief filed by DNP International Co Inc., Vital Pharmaceuticals Inc . . . (Attachments: # I Certificate of Service)(DiGiovanni, Francis) (Entered: Apr. 12, 2011).
*Natural Alternatives International Inc. v. Vital Pharmaceuticals Inc. et al*, filed Aug. 20, 2009, U.S. District Court District of Delaware (Wilmington) Civil Docket for Case #: 1:09-cv-00626-GMS; Claim Construction Answering Brief re 77 Claim Construction Opening Brief Plaintiffs' Answering Brief in Support of Claim Construction filed by Mark Dunnett, Roger Harris, Kenneth Johannsson, Natural

(56) References Cited

OTHER PUBLICATIONS

Alternatives International Inc. . . (Moore, David) Modified on Apr. 13, 2011 (mmm). (Entered: Apr. 12, 2011).
*Natural Alternatives International Inc.* v. *Vital Pharmaceuticals Inc. et al*, filed Aug. 20, 2009, U.S. District Court District of Delaware (Wilmington) Civil Docket for Case #: 1:09-cv-00626-GMS; Claim Construction Chart by DNP International Co Inc., Natural Alternatives International Inc., Vital Pharmaceuticals Inc . . . (DiGiovanni, Francis) (Entered: Mar. 10, 2011).
*Natural Alternatives International Inc.* v. *Vital Pharmaceuticals Inc. et al*, filed Aug. 20, 2009, U.S. District Court District of Delaware (Wilmington) Civil Docket for Case #: 1:09-cv-00626-GMS; Claim Construction Opening Brief filed by Compound Solutions, Inc., Mark Dunnett, Roger Harris, Kenneth Johannsson, Natural Alternatives International Inc . . . (Moore, David) (Entered: Mar. 25, 2011).
*Natural Alternatives International Inc.* v. *Vital Pharmaceuticals Inc. et al*, filed Aug. 20, 2009, U.S. District Court District of Delaware (Wilmington) Civil Docket for Case #: 1:09-cv-00626-GMS; Claim Construction Opening Brief filed by DNP International Co Inc., Vital Pharmaceuticals Inc . . . (DiGiovanni, Francis) (Entered: Mar. 25, 2011).
*Natural Alternatives International Inc.* v. *Vital Pharmaceuticals Inc. et al*, filed Aug. 20, 2009, U.S. District Court District of Delaware (Wilmington) Civil Docket for Case #: 1:09-cv-00626-GMS; Declaration re 77 Claim Construction Opening Brief of Keith A. Walter by DNP International Co Inc., Vital Pharmaceuticals Inc . . . (Attachments:#1 Exhibit A, # 2 Exhibit B, # 3 Exhibit C, # 4 Exhibit D, # 5 Exhibit E, # 6 Exhibit F, # 7 Exhibit G, # 8 Exhibit H, # 9. Exhibit I, # 10 Certificate of Service)(DiGiovanni, Francis) (Entered: Mar. 25, 2011).
*Natural Alternatives International Inc.* v. *Vital Pharmaceuticals Inc. et al*, filed Aug. 20, 2009, U.S. District Court District of Delaware (Wilmington) Civil Docket for Case #: 1:09-cv-00626-GMS; Declaration re 77 Claim Construction Opening Brief of Malcolm Watford, D.Phil. by DNP International Co Inc., Vital Pharmaceuticals Inc . . . (Attachments: #I Exhibit A, # 2 Certificate of Service)(DiGiovanni, Francis) (Entered: Mar. 25, 2011).
*Natural Alternatives International Inc.* v. *Vital Pharmaceuticals Inc. et al*, filed Aug. 20, 2009, U.S. District Court District of Delaware (Wilmington) Civil Docket for Case #: 1:09-cv-00626-GMS; Declaration re 91 Claim Construction Answering Brief, Declaration of William John McKeague by Mark Dunnett, Roger Harris, Kenneth Johannsson, Natural Alternatives International Inc . . . (Attachments:# 1 Exhibit A-E)(Moore, David) (Entered: Apr. 12, 2011).
*Natural Alternatives International Inc.* v. *Vital Pharmaceuticals Inc. et al*, filed Aug. 20, 2009, U.S. District Court District of Delaware (Wilmington) Civil Docket for Case #: 1:09-cv-00626-GMS; Joint Appendix re 91 Claim Construction Answering Brief, Joint Appendix of Intrinsic Evidence by Mark Dunnett, Roger Harris, Kenneth Johannsson, Natural Alternatives International Inc . . . (Attachments: # 1 Exhibit 1-12)(Moore, David) (Entered: Apr. 12, 2011).
*Natural Alternatives International Inc.* v. *Vital Pharmaceuticals Inc. et al*, filed Aug. 20, 2009, U.S. District Court District of Delaware (Wilmington) Civil Docket for Case #: 1:09-cv-00626-GMS; Official Transcript of Markman Hearing held on May 12, 2011 before Judge Sleet. Court Reporter/Transcriber Maurer. Transcript may be viewed at the court public terminal or purchased through the Court Reporter/Transcriber before the deadline for Release of Transcript Restriction. After that date it may be obtained through PACER. Redaction Request due Jun. 7, 2011. Redacted Transcript Deadline set for Jun. 17, 2011. Release of Transcript Restriction set for Aug. 15, 2011. (kjm) (Entered: May 17, 2011).
*Natural Alternatives International Inc.* v. *Vital Pharmaceuticals Inc. et al*, filed Aug. 20, 2009, U.S. District Court District of Delaware (Wilmington) Civil Docket for Case #: 1:09-cv-00626-GMS; Second Declaration re 94 Claim Construction Answering Brief, Second Declaration of Keith A. Walter by Vital Pharmaceuticals Inc . . . (Attachments: #I Exhibit J-0, # 2 Certificate of Service)(DiGiovanni, Francis) (Entered: Apr. 12, 2011).

*Natural Alternatives International, Inc.* v. *Woodbolt Distribution, LLC et al*, filed Jun. 14, 2013, U.S. District Court Southern District of Texas (Houston) Civil Docket for Case #: 4:13-cv-01742; Complaint against Natural Alternatives International, Inc. (Filing fee $ 400 receipt No. 0541-11572506) filed by Natural Alternatives International Inc . . . (Attachments:# I Exhibit 1, # 2 Exhibit 2)(Oparil, Richard) (Entered: Jun. 14, 2013).
*Natural Alternatives International, Inc.* v. *Woodbolt Distribution, LLC et al*, filed Jun. 14, 2013, U.S. District Court Southern District of Texas (Houston) Civil Docket for Case #: 4:13-cv-01742; Motion for Preliminary Injunction by Natural Alternatives International, Inc., filed. Motion Docket Date Jul. 5, 2013. (Attachments:# 1 Memorandum in Support, # 2 Declaration of Kenneth Wolf, # 3 Declaration of Matthew Titlow, # 4 Exhibit 3, # 5 Exhibit 4, # 6. Exhibit 5, # 7 Exhibit 6, # 8 Exhibit 7, # 9 Exhibit 8, # 10 Exhibit 9, # 11 Exhibit 10, # 12 Exhibit 11, # 13 Exhibit 12, # 14 Exhibit 13, # 15 Exhibit 14, # I6 Exhibit 15, # 17 Exhibit 16, # 18 Exhibit 17, # 19 Exhibit 18, # 20 Exhibit 19, # 21 Proposed Order)(Oparil, Richard) (Entered: Jun. 14, 2013).
*Natural Alternatives International, Inc.* v. *Woodbolt Distribution, LLC et al*, filed May 3, 2012, U.S. District Court Southern District of Texas (Houston) Civil Docket for Case #: 4:12-cv-01388; Complaint against Woodbolt Distribution, LLC (Filing fee$ 350 receipt No. 0541-9685733) filed by Natural Alternatives International, Inc . . . (Attachments: # I Exhibit 1, # 2 Exhibit 2, # 3 Exhibit 3, # 4 Exhibit 4, # 5 Exhibit 5, # 6 Exhibit 6, # 7 Exhibit 7, # 8 Exhibit 8, # 9 Exhibit 9, # 10 Exhibit 10, # 11 Exhibit 11,# 12 Exhibit 12, # 13 Exhibit 13, #I4 Exhibit 14, # 15 Exhibit 15, # 16 Exhibit 16, # 17 Exhibit 17, # 18 Exhibit 18, # 19 Exhibit 19, # 20 Civil Cover Sheet, # 21 Summons)(Oparil, Richard) (Entered: May 3, 2012).
*Natural Alternatives International, Inc.* v. *Woodbolt Distribution, LLC et al*, filed May 3, 2012, U.S. District Court Southern District of Texas (Houston) Civil Docket for Case #: 4:12-cv-01388; Motion for Preliminary Injunction by Natural Alternatives International, Inc., filed. Motion Docket Date Jun. 7, 2012. (Attachments:# I Memorandum in Support, # 2 Affidavit Kenneth Wolf, # 3 Affidavit Richard Oparil, # 4 Exhibit 20, # 5 Exhibit 21, # 6 Exhibit 22, # 7 Exhibit 23, # 8 Exhibit 24, # 9 Exhibit 25, # 10 Exhibit 26, # 11 Exhibit 27, # 12 Exhibit 28, # 13 Exhibit 29, # 14 Exhibit 30, # 15 Exhibit 31, # 16 Exhibit 32, # 17 Exhibit 33, # 18 Proposed Order)(Oparil, Richard) (Entered: May 17, 2012).
*Natural Alternatives International, Inc.* v. *Woodbolt Distribution, LLC et al*, filed May 3, 2012, U.S. District Court Southern District of Texas (Houston) Civil Docket for Case #: 4:12-cv-01388; Response in Opposition to 14 Motion for Preliminary Injunction, filed by Woodbolt Distribution, LLC. (Attachments:# 1 Exhibit A, # 2 Exhibit B, # 3 Exhibit C, # 4 Exhibit D, # 5 Exhibit E, # 6 Exhibit F, # 7 Exhibit G, # 8 Exhibit H, # 9 Exhibit I, # 10 Exhibit J, # 11 Exhibit K, # 12 Exhibit L, # 13 Exhibit M, # 14 Exhibit N, # 15 Proposed Order)(Partridge, Jayme) (Entered: Jun. 7, 2012).
*Woodbolt Distribution LLC* v. *Natural Alternatives International Inc. et al*, filed Dec. 21, 2011, U.S. District Court District of Delaware (Wilmington) Civil Docket for Case #: 1:11-cv-01266-GMS; Complaint for Declaratory Judgment of Patent Non-Infringement and Invalidity filed with Jury Demand against Compound Solutions Inc., Natural Alternatives International Inc.—Magistrate Consent Notice to Pltf. ( Filing fee $350, receipt No. 311-995916.)—filed by Woodbolt Distribution LLC. (Attachments:# I Exhibit 1,# 2 Civil Cover Sheet)(dmp, ) (Entered: Dec. 21, 2011).
*Woodbolt Distribution LLC* v. *Natural Alternatives International Inc. et al*, filed Dec. 21, 2011, U.S. District Court District of Delaware (Wilmington) Civil Docket for Case #: 1:11-cv-01266-GMS; First Amended Complaint For Declaratory Judgment of Patent Non-Infringement, Invalidity and Unenforceability, and for Violation of Antitrust Laws and Unfair Competition against Natural Alternatives International Inc.—filed by Woodbolt Distribution LLC. (Attachments:# I Exhibit 1-2) (Rawnsley, Jason) (Entered: Feb. 17, 2012).
*Woodbolt Distribution LLC* v. *Natural Alternatives International Inc. et al*, filed Jun. 24, 2013, U.S. District Court Southern District of Texas (Houston) Civil Docket for Case #: 4:13-cv-01834; Complaint against Natural Alternatives International, Inc. (Filing fee

(56) References Cited

OTHER PUBLICATIONS $400 receipt No. 0541-11614849) filed by Woodbolt Distribution, LLC.(Partridge, Jayme) (Entered: Jun. 24, 2013).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Complaint against All Defendants (Filing fee $ 350 receipt No. 0541-9035111) filed by Natural Alternatives International, Inc . . . (Attachments: # 1 Exhibit 1—US Patent)(Oparil, Richard) (Entered: Dec. 21, 2011).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Motion for Preliminary Injunction by Natural Alternatives International, Inc., filed. Motion Docket Date Jan. 31, 2012. (Attachments: # 1 Memorandum in Support, # 2 Declaration of Kenneth Wolf, # 3 Declaration of Lacy Kolo, # 4 Exhibit 1, # 5 Exhibit 2, # 6 Exhibit 3, # 7 Exhibit 4, # 8 Exhibit 5, # 9 Exhibit 6, # 10 Exhibit 7, # 11 Exhibit 8, # 12 Exhibit 9, # 13 Exhibit 10, # 14 Exhibit 11, # 15 Exhibit 12, # 16 Exhibit 13, # 17 Exhibit 14, # 18 Exhibit 15, # 19 Exhibit 16, # 20 Exhibit 17, # 21 Exhibit 18, # 22 Exhibit 19, # 23 Exhibit 20, # 24 Exhibit 21, # 25 Exhibit 22, # 26 Exhibit 23, # 27 Proposed Order)(Oparil, Richard) (Entered: Jan. 10, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Declaration of Kenneth Wolf re: 10 Motion for Preliminary Injunction, filed.(Oparil, Richard) (Entered: Jan. 10, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Reply in Support of NAI's Motion for a Preliminary Injunction (C.A. No. 12-1388 Dkt. No. 14), filed by Natural Alternatives International, Inc.. (Attachments: # 1 Exhibit A, # 2 Exhibit B, # 3 Exhibit C, # 4 Exhibit D, # 5 Exhibit E, # 6 Exhibit F, # 7 Exhibit G, # 8 Exhibit H, # 9 Exhibit I, # 10 Exhibit J, # 11 Exhibit K, # 12 Exhibit L, # 13 Exhibit M)(Oparil, Richard) (Entered: Jul. 18, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Answer to 1 Complaint with Jury Demand, Counterclaim against Natural Alternatives International, Inc. by Woodbolt Distribution, LLC, filed. (Attachments: # 1 Exhibit 1, # 2 Exhibit 2, # 3 Exhibit 3)(Partridge, Jayme) (Entered: Jul. 27, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Defendant Woodbolt's Answer to Plaintiff's Complaint in Member Case 12cv1388 by Woodbolt Distribution, LLC, filed. (Attachments: # 1 Exhibit 1, # 2 Exhibit 2, # 3 Exhibit 3)(Partridge, Jayme) (Entered: Jul. 27, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Stipulation re: as to Accused Products by Woodbolt Distribution, LLC, filed. (Attachments: # 1 Exhibit 1)(Partridge, Jayme) (Entered: Jul. 27, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Motion for Summary Judgment of Patent Invalidity of Plaintiffs U.S. Pat. No. 8,067,381 and U.S. Pat. No. 8,129,422 by Woodbolt Distribution, LLC, filed. Motion Docket Date Aug. 24, 2012. (Attachments: # 1 Proposed Order, # 2 Exhibit 1, # 3 Exhibit 2, # 4 Exhibit 3, # 5 Exhibit 4, # 6 Exhibit 5 Pt 1, # 7 Exhibit 5 Pt 2, # 8 Exhibit 6, # 9 Exhibit 7, # 10 Exhibit 8, # 11 Exhibit 9, # 12 Exhibit 10, # 13 Exhibit 11, # 14 Exhibit 12, # 15 Exhibit 13, # 16 Exhibit 14, # 17 Exhibit 15)(Partridge, Jayme) (Entered: Aug. 3, 2012) (pp. 1-358 of 699 pages total).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Motion for Summary Judgment of Patent Invalidity of Plaintiffs U.S. Pat. No. 8,067,381 and U.S. Pat. No. 8,129,422 by Woodbolt Distribution, LLC, filed. Motion Docket Date Aug. 24, 2012. (Attachments: # 1 Proposed Order, # 2 Exhibit 1, # 3 Exhibit 2, # 4 Exhibit 3, # 5 Exhibit 4, # 6 Exhibit 5 Pt 1, # 7 Exhibit 5 Pt 2, # 8 Exhibit 6, # 9 Exhibit 7, # 10 Exhibit 8, # 11 Exhibit 9, # 12 Exhibit 10, # 13 Exhibit 11, # 14 Exhibit 12, # 15 Exhibit 13, # 16 Exhibit 14, # 17 Exhibit 15)(Partridge, Jayme) (Entered: Aug. 3, 2012) (pp. 359-699 of 699 pages total).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Transcript re: Conference held on Jul. 23, 2012 before Judge Lynn N. Hughes. Court Reporter/Transcriber K. Metzger. Release of Transcript Restriction set for Nov. 5, 2012, filed. (kmetzger) (Entered: Aug. 6, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Answer to 50 Answer to Complaint, Counterclaim with Jury Demand by Natural Alternatives International, Inc., filed.(Oparil, Richard) (Entered: Aug. 9, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Response in Opposition to 53 Motion for Summary Judgment of Patent Invalidity of Plaintiffs U.S. Pat. No. 8,067,381 and U.S. Pat. No. 8,129,422, filed by Natural Alternatives International, Inc . . . (Oparil, Richard) (Entered: Aug. 17, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Cross Motion for Summary Judgment by Natural Alternatives International, Inc., filed. Motion Docket Date Sep. 7, 2012. (Attachments: # 1 Proposed Order, # 2 Affidavit)(Oparil, Richard) (Entered: Aug. 17, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Notice of filing of Exhibits 1-25 re: 62 Response in Opposition to Motion by Natural Alternatives International, Inc., filed. (Attachments: # 1 Exhibit 1, # 2 Exhibit 2, # 3 Exhibit 3, # 4 Exhibit 4, # 5 Exhibit 5, # 6 Exhibit 6, # 7 Exhibit 7, # 8 Exhibit 8, # 9 Exhibit 9, # 10 Exhibit 10, # 11 Exhibit 11, # 12 Exhibit 12, # 13 Exhibit 13, #14 Exhibit 14, #15 Exhibit 15, # 16 Exhibit 16, # 17 Exhibit 17, # 18 Exhibit 18, # 19 Exhibit 19, # 20 Exhibit 20, # 21 Exhibit 21, # 22 Exhibit 22, # 23 Exhibit 23, # 24 Exhibit 24, # 25 Exhibit 25)(Oparil, Richard) (Entered: Aug. 18, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Reply to Response to 63 Cross Motion for Summary Judgment, filed by Woodbolt Distribution, LLC. (Attachments: # 1 Exhibit 1, # 2 Exhibit 2, # 3 Exhibit 3)(Evans, Barry) (Entered: Aug. 24, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Reply in Support of 63 Cross Motion for Summary Judgment, filed by Natural Alternatives International, Inc . . . (Attachments: # 1 Exhibit A, # 2 Exhibit B, # 3 Exhibit C, # 4 Exhibit D, # 5 Exhibit E, # 6 Exhibit F, # 7 Exhibit G, # 8 Exhibit H, # 9 Affidavit of Richard J. Oparil)(Oparil, Richard) (Entered: Aug. 27, 2012).
*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Supplement to 63 Cross Motion for Summary Judgment, 53 Motion for Summary Judgment of Patent Invalidity of Plaintiffs U.S. Pat. No. 8,067,381 and U.S. Pat. No. 8,129,422 by Natural Alternatives International, Inc., filed.(Oparil, Richard) (Entered: Sep. 6, 2012).

(56) References Cited

OTHER PUBLICATIONS

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Transcript re: Conference held on Aug. 28, 2012 before Judge Lynn N. Hughes. Court Reporter/Transcriber Cher Barron. Release of Transcript Restriction set for Dec. 10, 2012., filed. (cbarron, ) (Entered: Sep. 10, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Motion for Leave to File surreply in response to plaintiff NAI Inc.s reply in support of summary judgment of infringement and patents not invalid, Motion to Strike Plaintiff's reply (D.I. 67) (Motion Docket Date Oct. 1, 2012.) by Woodbolt Distribution, LLC, filed. (Evans, Barry) (Entered: Sep. 10, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Motion for Leave to File Surreply in Response to Plaintiff's Reply in Support of Summary Judgment of Infringement and Patents Not Invalid, Motion to Strike Plaintiff's reply (D.I. 67) ( Motion Docket Date Oct. 1, 2012.) by Woodbolt Distribution, LLC, filed. (Attachments: # 1 Exhibit Proposed Surreply)(Evans, Barry) (Entered: Sep. 10, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Response to 72 Supplement NAI's Notice of Supplemental Authority, filed by Woodbolt Distribution, LLC. (Evans, Barry) (Entered: Sep. 27, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Reply to Response to 63 Cross Motion for Summary Judgment, filed by Woodbolt Distribution, LLC. (Evans, Barry) (Entered: Sep. 27, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Motion for Leave to File Supplemental Complaint and Summary Judgment Motion on Defendant Woodbolt's New COR-Performance-BCAA and COR-Performance Creatine Products by Natural Alternatives International, Inc., filed. Motion Docket Date Nov. 5, 2012. (Attachments: # 1 Exhibit A—Proposed Supplemental Complaint, # 2 Exhibit 1, # 3 Exhibit 2, # 4 Exhibit 3, # 5 Exhibit 4, # 6 Exhibit 5, # 7 Exhibit 6, # 8 Exhibit 7, # 9 Exhibit 8, # 10 Exhibit 9, # 11 Exhibit 10, # 12 Exhibit 11, # 13 Exhibit 12, # 14 Exhibit 13, # 15 Exhibit B—Proposed Summary Judgment Motion, # 16 Exhibit C, # 17 Affidavit, # 18 Proposed Order)(Oparil, Richard) (Entered: Oct. 15, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Response to 81 Motion for Leave to File Supplemental Complaint and Summary Judgment Motion on Defendant Woodbolt's New COR-Performance—BCAA and COR-Performance Creatine Products filed by Woodbolt Distribution, LLC. (Evans, Barry) (Entered: Oct. 16, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Supplement by Natural Alternatives International, Inc., filed. (Attachments: # 1 Exhibit 1, # 2 Exhibit 2, # 3 Exhibit 3, # 4 Exhibit 4, # 5 Exhibit 5, # 6 Exhibit 6, # 7 Exhibit 7, # 8 Exhibit 8, # 9 Exhibit 9, # 10 Exhibit 10, # 11 Exhibit 11, # 12 Exhibit 12, # 13 Exhibit 13)(Oparil, Richard) (Entered: Oct. 26, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Motion for Partial Summary Judgment of Patent Infringement by Woodbolt's Cellucor COR-Performance—BCAA and COR-Performance Creatine Products by Natural Alternatives International, Inc., filed. Motion Docket Date Nov. 16, 2012. (Attachments: # 1 Affidavit, # 2 Proposed Order)(Oparil, Richard) (Entered: Oct. 26, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Supplemental Complaint with jury demand against Woodbolt Distribution, LLC filed by Natural Alternatives International, Inc. (Attachments: # 1 Exhibit 1, # 2 Exhibit 2, # 3 Exhibit 3, # 4 Exhibit 4, # 5 Exhibit 5, # 6 Exhibit 6, # 7 Exhibit 7, # 8 Exhibit 8, # 9 Exhibit 9, # 10 Exhibit 10, # 11 Exhibit 11, # 12 Exhibit 12, # 13 Exhibit 13) (ghassan, ) (Entered: Nov. 14, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Supplemental Motion for Summary Judgment of Patent Infringement by Natural Alternatives International, Inc., filed. Motion Docket Date Nov. 30, 2012. (ghassan, ) (Entered: Nov. 14, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Answer to 89 Amended Complaint/Counterclaim/Crossclaim etc., with Jury Demand, Counterclaim against Natural Alternatives International, Inc. by Woodbolt Distribution, LLC, filed.(Evans, Barry) (Entered: Nov. 30, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Response in Opposition to 90 Motion for Summary Judgment, filed by Woodbolt Distribution, LLC. (Attachments: # 1 Exhibit 1)(Evans, Barry) (Entered: Nov. 30, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Reply in Support of 90 Motion for Summary Judgment, filed by Natural Alternatives International, Inc.. (Attachments: # 1 Exhibit 1, # 2 Exhibit 2, # 3 Exhibit 3, # 4 Exhibit 4, # 5 Exhibit 5, # 6 Exhibit 6, # 7 Affidavit of Richard J Oparil)(0paril, Richard) (Entered: Dec. 18, 2012).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Notice of Supplemental Authority by Natural Alternatives International, Inc., filed. (Oparil, Richard) (Entered: Jan. 23, 2013).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Notice of Supplemental Authority by Natural Alternatives International, Inc., filed. (Oparil, Richard) (Entered: Feb. 21, 2013).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Notice of Supplemental Authority by Natural Alternatives International, Inc., filed. (Attachments: # 1 Exhibit 1, # 2 Exhibit 2, # 3 Exhibit 3)(Oparil, Richard) (Entered: Feb. 22, 2013).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Management Order. By Mar. 8, 2013, Natural Alternatives must tell the court when it was known the function of dipeptides in muscles was to delay the onset of fatigue. By Mar. 8, 2013, Natural Alternatives must tell the court what Harris read that led him to begin his work with beta alanine. By Mar. 8, 2013, Natural Alternatives may brief the court on Woodbolt's priority argument. By Mar. 13, 2013, Woodbolt may respond. (Signed by Judge Lynn N. Hughes) Parties notified. (ghassan,) (Entered: Feb. 26, 2013).

*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Memorandum in Support of the Position that Patent Applications Can

(56) References Cited

OTHER PUBLICATIONS

Have Multiple Effective Filing Dates and in Support of its Claim for Priority by Natural Alternatives International, Inc., filed. (Attachments: # 1 Exhibit 1, # 2 Exhibit 2, # 3 Exhibit 3, # 4 Exhibit 4, # 5 Exhibit 5, # 6 Exhibit 6, # 7 Exhibit 7, # 8 Exhibit 8)(Oparil, Richard) (Entered: Mar. 8, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Memorandum Statement Regarding the Inventor's Research and the Declaration of Roger C. Harris, Ph.D. by Natural Alternatives International, Inc., filed.(Oparil, Richard) (Entered: Mar. 8, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Memorandum in Opposition to NAI's Memorandum in Support of the Position that Patent Applications Can Have Multiple Effective Filing Dates and in Support of its Claim for Priority by Woodbolt Distribution, LLC, filed. (Attachments: # 1 Exhibit A)(Evans, Barry) (Entered: Mar. 13, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Memorandum in Opposition to NAI's Memorandum Statement Regarding the Inventor's Research and the Declaration of Roger C. Harris, Ph.D. by Woodbolt Distribution, LLC, filed. (Attachments: # 1 Exhibit A, # 2 Exhibit B)(Evans, Barry) (Entered: Mar. 13, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Transcript re: Hearing held on Feb. 22, 2013 before Judge Lynn N. Hughes. Court Reporter J. Sanchez. Release of Transcript Restriction set for Jun. 13, 2013., filed. (jsanchez, ) (Entered: Mar. 15, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Motion for Leave to File Reply to Woodbolts Misleading Statements to the Court Regarding Dr. Harris Declaration and Attempt to Change Its Argument to Create a Genuine Issue of Material Fact on Its Priority Argument by Natural Alternatives International, Inc., filed. Motion Docket Date Apr. 8, 2013. (Attachments: # 1 Exhibit 1, # 2 Exhibit 2, # 3 Exhibit 3, # 4 Exhibit 4, # 5 Attachment A to Motion—Proposed Reply)(Oparil, Richard) (Entered: Mar. 18, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Response to 112 Motion for Leave to File Reply to Woodbolts Misleading Statements to the Court Regarding Dr. Harris Declaration and Attempt to Change Its Argument to Create a Genuine Issue of Material Fact on Its Priority Argument filed by Woodbolt Distribution, LLC. (Evans, Barry) (Entered: Apr. 8, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Management Order. The motion for a preliminary injunction by Natural Alternatives is denied 10 . The joint motion to expedite briefing is denied 18 . Natural Alternative's motion to strike is denied 32 . (Signed by Judge Lynn N. Hughes) Parties notified. (ghassan, ) (Entered: Apr. 15, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Reply to 109 , 110 , filed by Natural Alternatives International, Inc. (ghassan, ) (Entered: Apr. 15, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Reply to 117 Reply to Plaintiff Natural Alternative International, inc.s Reply, filed by Woodbolt Distribution, LLC. (Evans, Barry) (Entered: Apr. 19, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Declaration of Roger Charles Harris, Ph.D., filed.(0paril, Richard) (Entered: May 7, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Response to 119 Declaration of Roger Charles Harris, Ph.D., filed by Woodbolt Distribution, LLC. (Evans, Barry) (Entered: May 23, 2013).

*Natural Alternatives International, Inc. v. Woodbolt Distribution, LLC et al.*, filed Dec. 21, 2011, U.S. District Court Southern District of Texas (Houston) Civil Docket for Case #: 4:11-cv-04511; Notice of Additional Supplemental Authority in Opposition re: 53 Motion for Summary Judgment of Patent Invalidity of Plaintiffs U.S. Pat. No. 8,067,381 and U.S. Pat. No. 8,129,422 by Natural Alternatives International, Inc., filed. (Attachments: # 1 Exhibit A)(Ballard, Glenn) (Entered: Jul. 8, 2013).

Declaration of Dr. Roger Charles Harris, submitted Mar. 8, 2013, 11 pages, in *Natural Alternatives International, Inc. v. Woodbolt Distribution, LLC et al.*, filed Dec. 21, 2011, U.S. District Court Southern District of Texas (Houston) Civil Docket for Case #: 4:11-cv-04511.

Supplemental Declaration of Dr. Roger Charles Harris, submitted May 7, 2013, 11 pages, in *Natural Alternatives International, Inc. v. Woodbolt Distribution, LLC et al.*, filed Dec. 21, 2011, U.S. District Court Southern District of Texas (Houston) Civil Docket for Case #: 4:11-cv-04511.

Declaration of Frank L Margolis, PhD., submitted Jul. 8, 2013, 5 pages, in *Natural Alternatives International, Inc. v. Woodbolt Distribution, LLC et al.*, filed Dec. 21, 2011, U.S. District Court Southern District of Texas (Houston) Civil Docket for Case #: 4:11-cv-04511.

Declaration of Dr. Roger Charles Harris for U.S. Appl. No. 95/002,001 (Re-Examination of U.S. Pat. No. 8,067,381), submitted Oct. 29, 2012, 14 pages.

Declaration of Dr. Craig Sale for U.S. Appl. No. 95/002,001 (Re-Examination of U.S. Pat. No. 8,067,381), submitted Oct. 29, 2012, 6 pages.

Declaration of Dr. Roger Charles Harris for U.S. Appl. No. 95/002,048 (Re-Examination of U.S. Pat. No. 8,129,422), submitted Dec. 17, 2012, 15 pages.

Declaration of Dr. Robert F. Zoeller for U.S. Appl. No. 95/002,048 (Re-Examination of U.S. Pat. No. 8,129,422), submitted Dec. 17, 2012, 6 pages.

Margolis et al., "Carnosine Synthesis in Olfactory Tissue During Ontogeny: Effect of Exogenous β-Alanine," Journal of Neurochemistry, 44(5): 1459-1464 (1985).

Margolis, "Neurotransmitter Biochemistry of the Mammalian Olfactory Bulb," Biochemistry of Tast and Olfaction, 17: 369-394 (1981).

*Natural Alternatives International Inc. et al. v. DNP International Co. Inc.*, U.S. District Court District of Delaware (Wilmington) Civil Docket for Case #: 1:11-cv-788-GMS; Defendant DNP International Co., Inc.'s Initial Invalidity Contentions under Paragraph 4(D) of the Court's "Default Standard for Discovery," Jul. 10, 2013, 179 pages.

*Natural Alternatives International Inc. et al. v. DNP International Co. Inc.*, U.S. District Court District of Delaware (Wilmington) Civil Docket for Case #: 1:11-cv-788-GMS; Defendant DNP International Co., Inc.'s Responses & Objections to Plaintiffs Natural Alternatives International, Inc.'s and Compound Solutions, Inc.'s First Set of Interrogatories, Jul. 1, 2013, 37 pages.

*Natural Alternatives International Inc. et al. v. DNP International Co. Inc.*, U.S. District Court District of Delaware (Wilmington) Civil Docket for Case #: 1:11-cv-788-GMS; Defendant DNP International Co., Inc.'s Responses & Objections to Plaintiffs Natural

(56) References Cited

OTHER PUBLICATIONS

Alternatives International, Inc.'s and Compound Solutions, Inc.'s First Set of Requests for the Production of Documents, Jul. 1, 2013, 47 pages.
*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Docket Listing, 20 pages. (First entry dated Dec. 21, 2011).
*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Woodbolt's Answer to Complaint for Infringement of U.S. Pat. No. 8,067,381 and U.S. Pat. No. 8,129,422 and Counterclaims. (Entered: Jul. 16, 2013).
*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; GNC Corporation's Answer to Complaint for Infringement of U.S. Pat. No. 8,067,381 and U.S. Pat. No. 8,129,422 and Counterclaims. (Entered: Jul. 16, 2013).
*Natural Alternatives International, Inc.* v. *Woodbolt Distribution, LLC et al.*, filed Dec. 21, 2011, U.S. District Court Southern District of Texas (Houston) Civil Docket for Case #: 4:11-cv-04511; Bodybuilding.com's Answer to Complaint for Infringement of U.S. Pat. No. 8,067,381 and U.S. Pat. No. 8,129,422 and Counterclaims. (Entered: Jul. 16, 2013).
Admin, Beta-Alanine Review, (May 23, 2008) Retrieved from: -www.musclesweb.net/blog/beta-alanine-review/ [Retrieved on Jan. 5, 2010] [2 pages].
Asatoor et al., "Intestinal absorption of carnosine and its constituent amino acids in man," Gut, II: 250-254 (1970).
Babizhayev et al., "L-carnosine (beta-alanyl-L-histidine) and carcinine (beta-alanylhistamine) act as natural antioxidants with hydroxyl-radical-scavenging and lipid-peroxidase activities," Biochem J. 304 ( Pt 2):509-516 (1994).
Bakardjiev, A. and K. Bauer, "Transport of beta-alanine and biosynthesis of carnosine by skeletal muscle cells in primary culture," Eur. J. Biochem. 225(2):617-623 (1994).
Balcombe et al., "The Beta-Alanine Revolution featuring-IntraXCell®, The Definitive Guide on How Beta-Alanine Can Delay Muscular Fatigue, Allowing You to Train Harder & Longer," Athletic Edge Nutrition, 79 pages (2010).
Barger, G. and F. Tutin, "Carnosine, constitution and synthesis," Biochem J 12:402-407 (1918).
Batcombe et al., "Beta-Alanine: science meets real world results," (2006) Retrieved from: www.beta-alanine.net/ [Retrieved on Jan. 5, 2010] [8 pages].
Bauer et al. "Biosynthesis of carnosine and related peptides by skeletal muscle cells in primary culture," Eur. J. Biochem, 219: 43-47 (1994).
Bergström, J. "Muscle electrolytes in man," Scand. J. Clin. Invest. 14(Suppl. 68):1-110 (1962).
Beta-Alanine, information on Beta-Alanine, Carnosine and the CarnoSyn® product Frequently Asked Questions, (2007) Retrieved from: www.beta-alanine.com/Beta-alanine-faqs.asp [Retrieved on Jan. 5, 2010] [6 pages].
Beta-Alanine. The Facts., Retrieved from: www.betaalanine.info/background-on-beta-alanine/ [Retrieved on Jan. 5, 2010] [2 pages].
Biolo et al., "Insulin action on protein metabolism," Baillière's Clinical Endocrinology and Metabolism, 7(4), (1993).
Brooke, M. and K. Kaiser, "Muscle fiber types: how many and what kind?," Arch. Neruol. 23:369-379 (1970).
Burd et al., "Carnosine in primary afferents of the olfactory system: an autoradiographic and biochemical study," J. Neurosci. 2:244-255 (1982).
Casey et al., "Creatine ingestion favorably affects performance and muscle metabolism during maximal exercise in humans," Am. J. Physiol 271 (Endocrinol. Metab 34): E31-E37 (1996).

Certified English translation of Japanese patent of JP 2002 51730, published Feb. 19, 2002, entitled "Food Product for Sports". [9 pages].
Certified English translation of JP 61-204120, published Sep. 10, 1986 entitled "Immunomodulatory Agent". [7 pages].
Certified English translation of JP 64-042425, published Feb. 14, 1989, entitled "Remedy for Cachexia". [6 pages].
Certified English Translation of Osaka Hospital Pharmacist Association, "Zentei Iyakuhin-youran (the directory of pharmacrutical products)," Yakugyojihosya, the fifth impression, 576-577 (1986).
Certified English translation of Skulachev, V., [Carnosine and anserine as specialized pH-buffers-hydrogen ion carriers—article in Russian] Biokhimiya 57(9):1311-1316 (1992).
Collegiate Sport Nutrition, *CarnoSyn®—Carnosine Synthesizer* [Brochure] (4 pages) (2007).
Crim et al., "Creatin Metabolism in Men: Creatine Pool Size and Turnover in Relation to Creatine Intake" J. Nutr. 106 (3):371-381 (1976).
Decision of Patent, issued Dec. 15, 2009, in connection with Japanese Patent Application No. 10-509546.
Defendant Vital Pharmaceutical's First Supplemental Response to Plaintiff's Interrogatory No. 12, served Apr. 19, 2011.
Definition of "Dietary Supplement," [online], Retrieved from the Internet: <URL: {http://dictionary.reference.com/browse/dietary%20supplement}>, [Retrieved on Aug. 17, 2012] [1 page].
Derave et al., "Beta-Alanine supplementation augments muscle carnosine content and attenuates fatigue during repeated isokinetic contraction bouts in trained sprinters," J. Appl. Physiol. 103:1736-1743 (2007).
Derave et al., "Beta-alanine supplementation augments muscle carnosine content and attenuates fatigue in trained sprinters," National Strength and Conditioning Association Annual Conference, Atlanta, Jul. 2007.
Derave et al., "Creatine supplementation augments skeletal muscle carnosine content in senescence-accelerated mice (SAMP8)," Rejuvenation Res. 11(3):641-647 (2008).
Di Pasquale, M., "Conditionally essential amino acids," pp. 127-145 in Amino Acids and Proteins for the Athlete, CRC Press:Boca Raton (1997).
Dunnett et al., "Carnosine, anserine and taurine contents in individual fibres from the middle gluteal muscle of the camel," Res. Vet. Sci., 62:213-216 (1997).
Dunnett et al., "Influence of oral beta-alanine and L-histidine supplementation on the carnosine content of the gluteus medius," Equine Vet. J. Suppl. 30:499-504 (1999).
Dunnett et al., "Plasma carnosine concentration: diurnal variation and effects of age, exercise and muscle damage," Equine Vet. J. Suppl. 34:283-287 (2002).
Dunnett, "Carnosine Metabolism and Function in the Thoroughbred Horse," Full Dissertation, See (Open University) vol. 57/04-C of dissertation abstracts 1143 (1996).
Dunnett et al., "Determination of carnosine and other biogenic imidazoles in equine plasma by isocratic reversed-phase ion-pair high-performance liquid chromatography," J. Chromatogr. 579:45-53 (1992).
Dunnett et al., "High-performance liquid chromatographic determination of imidazole dipeptides, histidine, 1-methylhistidine and 3-methylhistidine in muscle and individual muscle fibers," J. Chromatogr. B. Biomed. Appl., 688:47-55 (1997).
Dunnett, "Carnosine Metabolism and Function in the Thoroughbred Horse," Thesis submitted in Open University, 362 pages (1995).
Dunnett, "High performance liquid-chromatographic determination of N-alpha-acetyl-L-carnosine in equine plasma," J. Chromatogr. B. Biomed. Sci. Appl. 688:150-154 (1997).
Examination Report, issued Apr. 28, 2009, in connection with Japanese Patent Application No. 10-509546.
Examination Report, issued Jul. 14, 2009, in connection with Japanese Patent Application No. 2006-509880.
Gardner et al., "Intestinal Absorption of the Intact Peptide Carnosine in Man, and Comparison with Intestinal Permeability to Lactulose," J. of Physiology, 439: 411-422 (1991).
Hama et al., "Intestinal Absorption of β-Alanine, Anserine and Carnosine in Rats," J. Nutr. Sci. Vitaminol, 22: 147-157 (1976).

(56) References Cited

OTHER PUBLICATIONS

Harris et al., "Absorption of creatine supplied as a drink, in meat or in solid form," J Sports Science 20:147-151 (2002).
Harris et al., "Beta-alanine Supplementation for 10 weeks significantly increased muscle carnosine levels," IUPS 2005 Meeting Abstract 566.8 from p. A969, Experimental Biology, San Diego, Apr. 2005.
Harris et al., "Carnosine & Taurine contents in individual fibers in human vastus lateralis muscles," J Sports Sci 16: 639-643 (1998).
Harris et al., "Changes in plasma β-alanine concentration following administration of free or peptide bound forms," Experimental Biology Conference, San Diego, Apr. 2003.
Harris et al., "Effect of 14 and 28 days β-alanine (Carnosyn™) supplementation on isometric endurance of the knee extensors," 3rd Annual International Society of Sports Nutrition Conference, Las Vegas, Jun. 2006.
Harris et al., "Effect of Combined β-alanine and creatine monohydrate supplementation on exercise performance," Medicine & Science in Sports & Exercise, Journal of the American College of Sports Medicine Conference, San Francisco, 35(5) Supplement 1:s218, May 2003.
Harris et al., "Effects of 14 days of beta-alanine supplementation on isometric endurance of the knee extensors," Medicine and Science in Sports and Exercise 38(5) Supplement, pp. S125-S126, Jun. 2006.
Harris et al., "Elevation of carnosine in muscle of normal subjects by supplementation with b-alanine in free or peptide bound form," Experimental Biology Conference, San Diego, Apr. 2003.
Harris et al., "Muscle buffering capacity and dipeptide content in the thoroughbred horse, greyhound dog and man," Comp. Biochem. Physiol. 97A(2):249-251 (1990).
Harris et al., "The absorption of orally supplied beta-alanine and its effect on muscle carnosine synthesis in human vastus lateralis," Amino Acids 30:279-289 (2006).
Harris et al., "The carnosine content of V lateralis in vegetarians and omnivores," FASEB Journal 21(6):A943, Experimental Biology, Washington D.C., Apr. 2007.
Harris et al., "The distribution of carnosine and taurine in different muscle fibre types from human v lateralis and the effects of beta-alanine supplementation," 9th International Congress on Amino Acids & Proteins, Vienna, Aug. 2005.
Harris et al., "The distribution of carnosine in different muscle fibre types with beta-alanine supplementation," IUPS 2005 Meeting Abstract 665.36 from p. A1125, Experimental Biology, San Diego, Apr. 2005.
Harris et al., "The effect of a supplement containing β-alanine on muscle carnosine synthesis and exercise capacity, during 12 wk combined endurance and weight training." J. Inter. Soc. Sports Nutr. 3(1):S9 (2006).
Harris et al., "The effect of a supplement containing b-alanine on muscle carnosine synthesis and exercise capacity, during 12 wk combined endurance and weight training," 3rd Annual International Society of Sports Nutrition Conference, Las Vegas, Jun. 2006.
Harris et al., "The effect of a β-alanine supplement on the muscle carnosine content during training," Experimental Biology, San Francisco, Abstract 483.35, Apr. 2006.
Harris et al., "The effect of physical training on the carnosine content of V lateralis using a one-leg training model," Medicine and Science in Sports and Exercise 39(5) Supplement, pp. S91, Jun. 2006.
Harris et al., "The effect of very high interval training on the carnosine content and buffering capacity of V lateralis from humans," Experimental Biology, Washington D.C., Apr. 2007.
Harris et al., "The effect of whole body physical training on the carnosine content of V lateralis," Experimental Biology, Washington D.C., Apr. 2007.
Harris et al., "The influence of B-alanine supplementation and training on the muscle carnosine content in human v lateralis, and the effect of this on exercise performance," 9th International Congress on Amino Acids & Proteins, Vienna, pp. 12-13, Aug. 2005.
Harris et al., "The plasma concentration-time profile of beta-alanine using a controlled-release formulation (Carnosyn®)," Meeting Abstract, The FASEB Journal 22:701.9 (2008).
Harris, R., "Multiple roles of carnosine in muscle, fact or fiction," FASEB Presentation, 2008, [42 pages].
Hill et al., "Influence of b-alanine supplementation on skeletal muscle carnosine concentrations and high intensity cycling capacity," Amino Acids 32:225-233 (2007).
Hill et al., "The effect of combined Beta-Alanine and Creatine Monohydrate Supplementation on Muscle Composition and Exercise Performance," Medicine & Science in Sports and Exercise 37(5) Supplement, S348, Jun. 2005.
Huszti et al., "Effects of I-histidine administration on the concentrations of histindine in various tissues," Agents Actions 4(3):183 (1974).
Jeukendrup, "SSE #106 Carbohydraate Supplementation During Exercise: Does It Help? How Much is Too Much?" Sports Science Library, Gatorade Sports Science Institute (2008).
Johnson, P., "Does Beta-Alanine work?" (Jul. 9, 2007) Retrieved from: www.betaalanine.info/background-on-beta-alanine/ [Retrieved on Jan. 5, 2010] [2 pages].
Jones et al., "Comparison of the carnosine content of V Lateralis of vegetarians and omnivores," FASEB Journal 21(6):A944, Experimental Biology, Washington D.C., Apr. 2007. Presented at British Association of Sport and Exercise Science, Student Conference, University of Chichester, Apr. 2007.
Jones et al., "o-Phthaldialdehyde precolumn derivatization and reversed-phase high-performance liquid chromatography of polypeptide hydrolysates and physiological fluids," J. Chromatogr. 266:471-482 (1983).
Kendrick et al., "The effect of β-alanine (Carnosyn™) supplementation on muscle carnosine synthesis during a 10 week program of strength training," 3rd Annual International Society of Sports Nutrition Conference, Las Vegas, Jun. 2006.
Kendrick et al., "The effect of β-alanine (Carnosyn™) supplementation on muscle carnosine synthesis during 4 weeks using a one-leg training model," 3rd Annual International Society of Sports Nutrition Conference, Las Vegas, Jun. 2006.
Kendrick et al., "The effects of 10 weeks of resistance training combined with beta-alanine supplementation on while body strength, force production, muscular endurance and body composition," Amino Acids, 34:547-554 (2008).
Kim et al., "Effect on muscle fibre morphology and carnosine content after 12 days training of Korean speed skaters," Medicine & Science in Sports and Exercise, 37(5) Supplement, S192, Jun. 2005.
Kvalnes-Krick et al., "Cloning, Sequencing, and Expression of cDNA Encoding β-Alanine Synthase from Rat Liver," J. of Bio. Chem., 268(8), pp. 5686-5693 (1993).
Li et al., "Bioactivities of Chicken Essence," J. of Food Science, 77: R105-R110 (2012).
Mannion et al., "Carnosine and anserine concentrations in the quadriceps femoris muscle of healthy humans," Eur. J. Appl. Physiol. Occup. Physiol. 64:47-50 (1992).
Marlin et al., "Carnosine content of the middle gluteal muscle in thoroughbred horses with relation to age, sex and training," Comp. Biochem. Physiol. A. 93:629-632 (1989).
Nutzenadel et al., "Uptake and metabolism of beta-alanine and L-carnosine by rat tissues in vitro: role in nutrition," Am J Physiol. 230(3):643-651 (1976).
Office Action, issued Apr. 27, 2010, in connection with Japanese Patent Application No. 2006-509880.
Order Construing the Terms of U.S. Pat. No. 5,965,596; U.S. Pat. No. 6,172,098; and U.S. Pat. No. 6,426,361, dated May 31, 2011.
Osaka Hospital Pharmacist Association, "Zentei Iyakuhin-youran (the directory of pharmacrutical products)," Yalcugyojihosya, the fifth impression, 576-577 (1986).
Reaction rate tends to increase with concentration—phenomenon explained by collision theory, Chemical kinetics, Wikipedia.org. <URL: en.wikipedia.org/wiki/Chimical_kinetics> [retrieved from the internet May 23, 2012].

(56) References Cited

OTHER PUBLICATIONS

Sewell et al., "Estimation of the carnosine content of different fibre types in the middle gluteal muscle of the thoroughbred horse," J. Physiol., 455:447-453 (1992).
Shoten, I., Dictionary of Physics and Chemistry, 4th ed., 90 (1987).
Skulachev, V., [Carnosine and anserine as specialized pH-buffers—hydrogen ion carriers—article in Russian] Biokhimiya 57(9):1311-1316 (1992).
Smith, E., "The buffering of muscle in rigor: protein, phosphate and carnosine," J Physiol 92(3):336-343 (1938).
Stout et al., "Effects of β-alanine supplementation on the onset of neuromuscular fatigue and ventilatory threshold in women," Amino Acids 32:381-386 (2007).
Stout et al., The effect of beta-alanine supplementation on neuromuscular fatigue in elderly (55-92 Years): a double-blind randomized study, J Int Soc Sorts Nutr. 5:21 (2008).
Supplemental European Search Report, issued Apr. 21, 2010 in connection with European Patent Application No. 04749952.0.
Suzuki et al., "High level of skeletal muscle carnosine contributes to the latter half of exercise performance during 30-s maximal cycle ergometer sprinting," Jpn J Physiol 52:199-205 (2002).
Tallon et al., "Acute changes in plasma carnosine, creatine and markers of purine degradation following exercise," Experimental Biology, Washington D.C., Abstract 1b544, Apr. 2007.
Tallon et al., "Carnosine, taurine and enzyme activities of human skeletal muscle fibres from elderly subjects with osteoarthritis and young moderately active subjects," Biogerontology 8:129-137 (2007).
Tallon et al., "Single muscle fibre analysis of carnosine and associated metabolites in Korean breath hold divers (AMA)," Experimental Biology, Washington D.C., Abstract 1b538, Apr. 2007.
Tallon et al., "The carnosine content of vastus lateralis is elevated in resistance-trained bodybuilders," J. Strength Cond. Res. 19:725-729 (2005).
Tallon, "Research Summaries on β-Alanine/Histidine Supplementation and its Role in Hydrogen-Binding, pH-Controlling, and Carnosine Storage in Skeletal Muscle," iSatori Technologies, Product No. 17805, 8 pages. (2005).
Tamaki et al., "Biosynthesis and degradation of carsonine and turnover rate of its constituent amino acid in rats," J. Nurt. Sci. Vitaminol. 26:127-139 (1980).
Wu et al., "Proximate Composition, Free Amino Acids and Peptides Contents in Commercial Chicken and Other Meat Essences," J. of Food and Drug Analysis, 10(3): 170-177 (2002).
In the U.S. Patent and Trademark Office, Confirmation of Hearing by Appellant in re: U.S. Appl. No. 95/002,048 (Re-Examination of U.S. Pat. No. 8,129,422), dated Feb. 1, 2016.
In the U.S. Patent and Trademark Office, Miscellaneous Communication to Applicant, action stayed in re: U.S. Appl. No. 14/824,794, dated Dec. 30, 2016.
In the U.S. Patent and Trademark Office, Office Action in re: U.S. Appl. No. 14/824,794, dated Jul. 6, 2016.
In the U.S. Patent and Trademark Office, Patent Board Decision—Examiner Affirmed and Patent Board Decision: New Ground of Rejection in re: U.S. Appl. No. 95/002,048 (Re-Examination of U.S. Pat. No. 8,129,422), dated May 13, 2016.
In the U.S. Patent and Trademark Office, Patent Owner request for Rehearing and Notice of concurrent proceedings in re: U.S. Appl. No. 95/002,048 (Re-Examination of U.S. Pat. No. 8,129,422), dated Jun. 13, 2016.
"Kegg Pathway: beta-Alanine metabolism" Kanehisa Laboratories, [online], 2012, [retrieved on Oct. 30, 2013]. Retrieved from the Internet: < URL: http://www.genome.jp/kegg-bin/show_pathway?ec00410>. 1 page.

"Manual of Patent Examining Procedure §201.11," Manual of Patent Examining Procedure, Aug. 2006:5.
"Manual of Patent Examining Procedure §706.02," Manual of Patent Examining Procedure, Aug. 2012: 9, 3 pages.
"Methods and Compositions for Increasing the Anaerobic Working Capacity in Tissues," first page of Specification indicating Related Applications, filed Aug. 29, 2008, 1 page.
"Plaintiff Natural Alternatives International, Inc.'s Memorandum in Support of the Position That Patent Applications Can Have Multiple Effective Filing Dates and in Support of Its Claim to Priority," Mar. 8, 2013; 27 pages.
Balsom et al., "Creatine supplementation and dynamic high-intensity intermittent exercise," Scand J Med Sci Sports, 3:143-149 (1993).
Declaration of Stephen G. Kunin with curriculum vitae for U.S. Appl. No. 95/002,048 (Re-Examination of U.S. Pat. No. 8,129,422), submitted Aug. 23, 2013, 20 pages.
Definition of "Daily," [online], [retrieved on Oct. 30, 2013]. Retrieved from the Internet: < URL: http://dictionary.reference.com/browse/daily?s=t>. 1 page.
Di Pasquale, M., "Conditionally essential amino acids," pp. 36, 99, 121 and 153 in Amino Acids and Proteins for the Athlete, CRC Press:Boca Raton (1997).
Donner, "Patent Prosecution (2d ed. 1999)" The Bureau of National Affairs, Inc., second printing 2002, 4 pages.
Examination Report, issued Feb. 12, 2008, in connection with Japanese Patent Application No. 10-509546.
Exhibit 1 to Harris Declaration, "Material Safety Data Sheet Beta-Alanine MSDS," ScienceLab.com, 2005, pp. 1-5.
Fryburg et al., "Insulin and Insulin-like Growth Factor-I Enhance Human Skeletal Muscle Protein Anabolism during Hyperaminoacidemia by Different Mechanisms," J Clin. Invest. 96: 1722-1729 (1995).
Harris et al., "The effect of very high interval training on the carnosine content and buffering capacity of V lateralis from humans," Experimental Biology, Washington D.C., Meeting Abstract 769.19 from p. A944, Apr. 2007.
Harris, "Declaration of Dr. Roger Charles Harris," Mar. 8, 2013, pp. 1-11.
Plaintiff Natural Alternatives International, Inc.'s Statement Regarding Inventor's Research and the Declaration of Roger C. Harris, Ph.D., Mar. 8, 2013, 5 pages.
Manolagas, Stavros, "Birth and Death of Bone Cells: Basic Regulatory Mechanisms and Implications for the Pathogenesis and Treatment of Osteoporosis," Endocrine Reviews, 2000: 21(2), pp. 115-137.
Medline Plus, [online], [retrieved on Nov. 5, 2014 11 :56:17 AM]. Retrieved from the Internet: <URL: http://www.nlm.nih.gov/medlineplus/ency/article/002469.htm.
Moy, "1 Moy's Walker on Patents § 3:59 (4th ed.)", Thomson Reuters, updated Dec. 2012, 4 pages.
Preen et al., "Creatine supplementation: a comparison of loading and maintenance protocols on creatine uptake by human skeletal muscle." Int J Sport Nutr Exerc Metab. Mar. 2003;13(1):97-111.
Rawn, David. Biochemistry. New York: Harper & Row Publishers, 1983. Print. pp. 862-863.
Terminal Disclaimers to Obviate a Double Patenting Rejection Over a "Prior" Patent and Statements under 37 CFR 3.73(b), U.S. Appl. No. 12/806,356, Jun. 16, 2011, 6 pages.
Terminal Disclaimers to Obviate a Double Patenting Rejection Over a "Prior" Patent, U.S. Appl. No. 13/215,073, Sep. 7, 2011, 6 pages.
Ziv et al., "Oral Administration of Insulin in Solid Form to Nondiabetic and Diabetic Dogs," J. Pharmaceutical Sciences, 83(6): 792-794 (1994).

| TREAT-MENT | | | DOSING TIMES | | | | | | | | AVG DOSE (mg × times) | PER DAY | |
|---|---|---|---|---|---|---|---|---|---|---|---|---|---|
| | | | 9am | 10am | 11am | 12noon | 3pm | 4pm | 5pm | 6pm | | GIVEN | as β-Ala |
| 1 Beta alanine (β-Ala) n = 5 | Week | 1 | | 800mg | | 800mg | | 800mg | | 800mg | 800 × 4 | 3.2g | 3.2g |
| | | 2 | | 800mg | | 800mg | | 800mg | | 800mg | 800 × 4 | 3.2g | 3.2g |
| | | 3 | | 800mg | | 800mg | | 800mg | | 800mg | 800 × 4 | 3.2g | 3.2g |
| | | 4 | | 800mg | | 800mg | | 800mg | | 800mg | 800 × 4 | 3.2g | 3.2g |
| | | | | | | | | | | | Total 90g β=Ala in 4W | | |
| 2 Beta alanine (β-Ala) n = 5 | Week | 1 | 800mg | 400mg | 400mg | 400mg | 400mg | 400mg | 400mg | 400mg | 500 × 8 | 4.0g | 4.0g |
| | | 2 | 800mg | 400mg | 400mg | 800mg | 800mg | 400mg | 400mg | 800mg | 600 × 8 | 4.8g | 4.8g |
| | | 3 | 800mg | 400mg | 800mg | 800mg | 800mg | 800mg | 800mg | 800mg | 700 × 8 | 5.6g | 5.6g |
| | | 4 | 800mg | 800mg | 800mg | 800mg | 800mg | 800mg | 800mg | 800mg | 800 × 8 | 6.4g | 6.4g |
| | | | | | | | | | | | Total 146gβ =Ala in 4W | | |
| 3 Carnosine (C) n = 5 | Week | 1 | 1500mg | 1500mg | 1000mg | 1000mg | 1500mg | 1500mg | 1000mg | 1000mg | 1250 × 8 | 10g | 4.0g |
| | | 2 | 1500mg | 1500mg | 1500mg | 1500mg | 1500mg | 1500mg | 1500mg | 1500mg | 1500 × 8 | 12g | 4.8g |
| | | 3 | 2000mg | 1500mg | 1500mg | 2000mg | 2000mg | 1500mg | 1500mg | 2000mg | 1750 × 8 | 14g | 5.6g |
| | | 4 | 2000mg | 2000mg | 2000mg | 2000mg | 2000mg | 2000mg | 2000mg | 2000mg | 2000 × 8 | 16g | 6.4g |
| | | | | | | | | | | | Total 364g C in 4W (145g β=Ala) | | |

FIG. 17

METHODS AND COMPOSITIONS FOR INCREASING THE ANAEROBIC WORKING CAPACITY IN TISSUES

RELATED APPLICATIONS

This application is a continuation of U.S. application Ser. No. 13/900,244, filed May 22, 2013, now U.S. Pat. No. 8,993,610, issued Mar. 31, 2015, which is a continuation of U.S. application Ser. No. 13/356,182, filed Jan. 23, 2012, now U.S. Pat. No. 8,470,865, issued Jun. 25, 2013, which is a continuation of U.S. application Ser. No. 12/806,356, filed Aug. 10, 2010, now U.S. Pat. No. 8,129,422, issued Mar. 6, 2012, which is a continuation of U.S. application Ser. No. 12/231,240, filed Aug. 29, 2008, now U.S. Pat. No. 7,825,084, issued Nov. 2, 2010, which is a continuation of U.S. application Ser. No. 10/717,217, filed Nov. 18, 2003, now U.S. Pat. No. 7,504,376, issued Mar. 17, 2009, which claims the benefit of priority under 35 U.S.C. §119(e) of U.S. Provisional Application No. 60/462,238 filed Apr. 10, 2003. The aforementioned applications are incorporated by reference in their entirety.

TECHNICAL FIELD

This invention relates to the fields of pharmaceuticals and physiology. In one aspect, the invention provides methods for increasing the buffering capacity of muscles and decreasing muscle fatigue. The invention also provides methods and compositions for increasing the anaerobic working capacity of muscle and other tissues.

BACKGROUND

Natural food supplements are typically designed to compensate for reduced levels of nutrients in the modern human and animal diet. In particular, useful supplements increase the function of tissues when consumed. It can be particularly important to supplement the diets of particular classes of animals whose normal diet may be deficient in nutrients available only from meat and animal products (e.g., human vegetarians and other animals who consume an herbivorous diet).

For example, in the sporting and athletic community, natural food supplements which specifically improve athletic ability are increasingly important, such as supplements that promote or enhance physical prowess for leisure or employment purposes. In another example, anaerobic (e.g., lactate-producing) stress can cause the onset of fatigue and discomfort that can be experienced with intense exercise (e.g., continuous or intermittent sprinting in soccer or ice-hockey), where oxygen availability may be limited (e.g., peripheral vascular disease, free diving or synchronized swimming) and with aging. Anaerobic stress can also result from prolonged submaximal isometric exercise when the local circulation is partially or totally occluded by the increase in intra-muscular pressure (e.g., during rock climbing). Excessive lactate production can result in the acidification of the intracellular environment.

Creatine (i.e., N-(aminoiminomethyl)-N-glycine, N-amidinosarcosine, N-methyl-N-guanylglycine, or methylglycocyamine) is found in large amounts in skeletal muscle and other "excitable" tissues (e.g., smooth muscle, cardiac muscle, or spermatozoa) characterized by a capacity for high and variable energy demand. Creatine is converted into phosphorylcreatine in energy-generating biochemical pathways within cells. In mammalian skeletal muscle, the typical combined content of creatine (i.e., creatine and phosphorylcreatine) may vary from less than 25 to about 50 mmol per kilogram fresh muscle (i.e., 3.2 to 6.5 grams per kilogram fresh muscle).

Creatine is formed in the liver and taken up into tissues, such as muscle, by means of an active transport system. Creatine synthesis in the body may also be augmented by the ingestion of creatine present in meat (e.g., 5-10 milligrams per kilogram body weight per day in the average meat-eating human and approximately zero in a vegetarian diet).

During sustained intense exercise, or exercise sustained under conditions of local hypoxia, the accumulation of hydronium ions formed during glycolysis and the accumulation of lactate (anaerobic metabolism) can severely reduce the intracellular pH. The reduced pH can compromise the function of the creatine-phosphorylcreatine system. The decline in intracellular pH can affect other functions within the cells, such as the function of the contractile proteins in muscle fibers.

Dipeptides (also referred to herein as peptides) of beta-alanine and histidine, and their methylated analogues, which include carnosine (beta-alanyl-L-histidine), anserine (beta-alanyl-L-1-methylhistidine), or balenine (beta-alanyl-L-3-methylhistidine), are present in the muscles of humans and other vertebrates. Carnosine is found in appreciable amounts in muscles of, for example, humans and equines. Anserine and carnosine are found in muscles of, for example, canines, camelids and numerous avian species. Anserine is the predominant beta-alanylhistidine dipeptide in many fish. Balenine is the predominant beta-alanylhistidine dipeptide in some species of aquatic mammals and reptiles. In humans, equines, and camelids, the highest concentrations of the beta-alanylhistidine dipeptides are found in fast-contracting glycolytic muscle fibers (type IIA and IIB) which are used extensively during intense exercise. Lower concentrations are found in oxidative slow-contracting muscle fibers (type I). See, e.g., Dunnett, M. & Harris, R. C. Equine Vet. J., Suppl. 18, 214-217 (1995). It is known that carnosine contributes to hydronium ion buffering capacity in different muscle fiber types, and up to 50% of the total in equine type II fibers.

SUMMARY

The invention provides methods of increasing anaerobic working capacity in a tissue, comprising the following steps: (a) providing a beta-alanylhistidine dipeptide and a glycine, an insulin, an insulin mimic, or an insulin-action modifier; and (b) administering the beta-alanine and at least one of the glycine, insulin mimic, or insulin-action modifier to the tissue in an amount effective to increase beta-alanylhistidine dipeptide synthesis in the tissue, thereby increasing the anaerobic working capacity in the tissue. The invention provides methods of regulating hydronium ion concentrations in a tissue comprising the following steps: (a) providing a beta-alanylhistidine dipeptide and a glycine, an insulin an insulin mimic, or an insulin-action modifier; and (b) administering the beta-alanine and at least one of the glycine, insulin mimic, or insulin-action modifier to the tissue in an amount effective to increase the hydronium ion concentration in the tissue.

In one aspect of the methods, the step of administering the beta-alanine and at least one of the glycine, insulin mimic, or insulin-action modifier to the tissue comprises oral administration, administration to a blood or blood plasma or a combination thereof. The beta-alanylhistidine dipeptide can comprise a carnosine, an anserine, or a balenine, or analogs or mimetics thereof.

The invention provides compositions comprising a mixture of a glycine, an insulin, an insulin mimic or an insulin-action modifier, and a composition comprising an amino acid or an active derivative thereof selected from the group consisting of a beta-alanine, a chemical derivative of beta-alanine and a peptide comprising a beta-alanine or analogs thereof. In one aspect, the beta-alanine comprises a beta-alanylhistidine dipeptide, such as a carnosine, an anserine or a balenine or analogs thereof. The compositions can further comprise at least a creatine or a carbohydrate.

In one aspect, the insulin mimic comprises a D-pinitol (3-O-methyl-chiroinositol), a 4-hydroxy isoleucine, a demethyl-asterriquinone B-1 compound, an alpha lipoic acid, an R-alpha lipoic acid, a guanidiniopropionic acid, a vanadium compound, a vanadium complex or a synthetic phosphoinositolglycan peptide. The insulin-action modifier can be a sulphonylurea, a thiazolidinedione or a biguanide.

In alternative aspects, the composition is a pharmaceutical composition, a dietary supplement or a sports drink. The dietary supplement or sports drink can be a supplement for humans. The pharmaceutical composition can be formulated for humans.

The invention provides compositions comprising at least 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, 4.0, 4.5, 5.0, 5.5, 6.0, 6.5 or more grams of a peptide or an ester comprising a beta-alanine or analogs or mimetics thereof. The invention provides compositions comprising at least about 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, 4.0, 4.5, 5.0, 5.5, 6.0, 6.1, 6.2, 6.3, 6.4, 6.5 or more grams of a peptide or an ester comprising a beta-alanine (or analogs or mimetics thereof) in an injectable form. In one aspect, the peptide comprises a beta-alanylhistidine dipeptide, such as a carnosine, an anserine or a balenine, or analogs or mimetics thereof.

The invention provides compositions formulated for humans comprising at least 200, 225, 250, 275, 300, 325, 350, 400, 425, 450, 475, 500, 525, 550, 575, 600, 625, 650, 675, 700, 750, 775, 800, 825, 850, 875, 900, 925, 950, 975 or 1000 or more mg of a beta-alanine or beta-alanine analogs or mimetics. In one aspect, the composition is formulated in an ingestible or an injectable formulation. The ingestible formulation can be a drink, a gel, a food or a tablet. The peptide can comprise a beta-alanylhistidine dipeptide, such as a carnosine, an anserine or a balenine, or analogs or mimetics thereof.

The invention provides methods of increasing the anaerobic working capacity of a tissue in a subject comprising the following steps: (a) providing a composition comprising (i) a mixture of a glycine, an insulin, an insulin mimic or an insulin-action modifier, and a composition comprising an amino acid or an active derivative thereof selected from the group consisting of a beta-alanine, a chemical derivative of beta-alanine and a peptide comprising a beta-alanine, or analogs or mimetics thereof; (ii) at least 0.5 gram of a peptide or an ester comprising a beta-alanine in an injectable form; or, (iii) at least 200 mg of a beta-alanine; and (b) administering the composition to the subject in an amount effective to increase the anaerobic working capacity of the tissue. In one aspect, the total dosage of the beta-alanine for a 24-hour period is at least about 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, 4.0, 4.5, 5.0, 5.5, 6.0, 6.1, 6.2, 6.3, 6.4, 6.5 or more grams. The total dosage of the beta-alanine for a 24-hour period can be between about 0.2 gram and about 6.4, 6.5, 6.6, 6.7, 6.8, 6.9, 7.0 or more grams. The composition can be given over a period of at least 3, 4, 5, 6, 7, 8, 9, 10, 11, 12, 13, 14 or 15 or more days. The composition can be given over a period of at least about 3 days to about two, three, four or more weeks. The beta-alanine can comprise a beta-alanylhistidine dipeptide, such as a carnosine, an anserine or a balenine, or analogs or mimetics thereof. The total dosage of the beta-alanylhistidine dipeptide over a 24 hour period can be at least about 0.5 gram, 0.6, 0.7, 0.8, 0.9, 1.0, 1.1, 1.2, 1.3, 1.4, 1.5, 2.0, 2.5, 3.0, 3.5, 4.0, 4.5, 5.0, 5.5, 6.0, 6.1, 6.2, 6.3, 6.4, 6.5 or more grams. The total dosage of the beta-alanylhistidine dipeptide over a 24 hour period can be greater than about 5, 6, 7, 8, 9, 10, 11, 12, 13, 14, 15, 16, 17, 18, 19 or 20 or more grams. The total dosage of the beta-alanylhistidine dipeptide over a 24 hour period can be more than about 5 gram to about 16 gram. The composition can be administered in multiple doses. The composition can be administered at least two times to eight times in a 24-hour period. In one aspect, about 200 mg, 225, 250, 275, 300, 325, 350, 400, 425, 450, 475, 500, 525, 550, 575, 600, 625, 650, 675, 700, 750, 775, 800, 825, 850, 875, 900, 925, 950, 975 or 1000 mg of a beta-alanine (or analogs or mimetics thereof) and/or about 500 mg (or, about 200 mg, 225, 250, 275, 300, 325, 350, 400, 425, 450, 475, 500, 525, 550, 575, 600, 625, 650, 675, 700, 750, 775, 800, 825, 850, 875, 900, 925, 950, 975 or 1000 mg) of carnosine (or analogs or mimetics thereof) is administered about two to eight, or more, times a day (e.g., 2, 3, 4, 5, 6, 7, 8 or more times a day) over a period of several weeks. In one aspect, at least about 2 g of a beta-alanine or at least about 5 g of carnosine is administered about two to eight times a day over a period of about two, three or four days.

In one aspect, the amount of a composition of the invention administered is increased daily. The amount of the composition of the invention administered can be increased weekly. The composition can be administered in treatment periods that last for at least about four weeks.

While the invention is not limited by any particular mechanism of action, the invention provides methods of regulating hydronium ion concentration in tissue in a subject comprising the following steps: (a) providing a composition comprising (i) a mixture of a glycine, an insulin, an insulin mimic or an insulin-action modifier, and a composition comprising an amino acid or an active derivative thereof selected from the group consisting of a beta-alanine, a chemical derivative of beta-alanine and a peptide comprising a beta-alanine or analogs or mimetics thereof; (ii) at least 0.5 gram of a peptide or an ester comprising a beta-alanine in an injectable form; or, (iii) at least 200 mg of a beta-alanine; and (b) administering the composition to the subject in an amount effective to regulate the hydronium ion concentration in the tissue.

In one aspect, the invention features methods and compositions for increasing the anaerobic working capacity of muscle and other tissues. The methods and compositions of the invention provide for the simultaneous accumulation of creatine and/or beta-alanylhistidine dipeptides, or beta-alanine and L-histidine analogues, within a tissue in the body. The methods include ingesting or infusing compositions into the body. In one aspect, the compositions are mixtures of compounds capable of increasing the availability and uptake of creatine and of precursors for the synthesis and accumulation of beta-alanylhistidine dipeptides in human and animal tissue. The compositions of the invention can induce the synthesis and accumulation of beta-alanylhistidine dipeptides in a human or animal body when introduced into the body.

The compositions can include beta-alanine, chemical derivatives and analogs of beta-alanine such as esters of beta-alanine, peptides of beta-alanine, such as carnosine, anserine, and balenine, as well as analogues thereof. The compositions may also include L-histidine and mixtures thereof. Each of the beta-alanine and/or L-histidine can be formulated or administered as individual amino acids, or, as components of dipeptides (e.g., carnosine, anserine, and/or balenine), oligopeptides, or polypeptides. The beta-alanine, L-histidine, carnosine, anserine, and/or balenine, or peptides of beta-alanine can be active derivatives. An active derivative is a compound derived from, or is a precursor of, a substance and performs in the same or similar way in the body as the substance, or which is processed into the substance when placed into the body. Examples include, for example, esters and amides. Compositions can also include any one or more of a creatine, a carbohydrate, insulin, an insulin mimic, an insulin-action modifier or a glycine. The compositions of the invention can be used for the preparation of a dietary supplement (including, e.g., drinks, gels, foods) or pharmaceutical composition for humans or animals. The compositions of the invention can be used in any of the methods of the invention.

In one aspect, the invention features compositions for and a method of regulating hydronium ion concentrations in a tissue. The method includes the steps of providing an amount of beta-alanine to blood or blood plasma effective to increase beta-alanylhistidine dipeptide synthesis in a tissue and exposing the tissue to the blood or blood plasma, whereby the concentration of beta-alanylhistidine is increased in the tissue. The beta-alanylhistidine may be a carnosine, anserine, or a balenine. The method can include the step of providing an amount of L-histidine to the blood or blood plasma effective to increase beta-alanylhistidine dipeptide synthesis.

In another aspect, the invention features a method of increasing the anaerobic working capacity of a tissue. The method includes the steps of providing an amount of beta-alanine to blood or blood plasma effective to increase beta-alanylhistidine dipeptide synthesis in a tissue, providing an amount of L-histidine to the blood or blood plasma effective to increase beta-alanylhistidine dipeptide synthesis in a tissue, and exposing the tissue to the blood or blood plasma. The concentration of beta-alanylhistidine is increased in the tissue.

In alternative aspects, the methods can include the step of increasing a concentration of creatine in the tissue. The increasing step can include providing an amount of creatine to the blood or blood plasma effective to increase the concentration of creatine in the tissue (e.g., by providing creatine to the blood or blood plasma).

The providing steps of the methods can include ingestion, infusion (e.g., injection) or a combination of ingestion and infusion, of a composition including an amount of beta-alanine, a peptide of beta-alanine such as carnosine, anserine and balenine which are hydrolyzed to their constituent amino acids on ingestion and are a source of beta-alanine for the body. Methods of the invention also include providing L-histidine, creatine, carbohydrate, insulin, insulin mimics, insulin-action modifiers and/or glycine.

In yet another aspect, the methods can include increasing a concentration of insulin in the blood or blood plasma. The concentration of insulin can be increased, for example, by injection of insulin. Methods of the invention can also include injection ingestion, or other modes of delivery, known to those of skill in the art, to a body (also referred to as a subject) of insulin mimics. Examples of insulin mimics include, but are not limited to, D-pinitol (3-O-methyl-chiroinositol), 4-hydroxy isoleucine, L783,281 (a demethylasterriquinone B-1 compound), alpha lipoic acid, R-alpha lipoic acid, guanidiniopropionic acid, vanadium compounds such as vanadyl sulfate or vanadium complexes such as peroxovanadium, and synthetic phosphoinositolglycans (PIG peptides). Additionally or alternatively, methods of the invention can include the use of insulin-action modifiers to enhance or inhibit the action of insulin in the body. Examples of insulin-action modifiers can include, but are not limited to, sulphonylureas, thiazolidinediones, and biguanides.

In still another aspect, the methods include providing glycine to a body. It is thought that glycine may suppress blood glucose release in the blood after ingestion of a meal. It may be that glycine enhances insulin sensitivity by promoting greater glucose uptake. Accordingly, the methods include providing glycine alone or in conjunction with insulin, insulin mimics or insulin-action modifiers in the compositions and methods of the invention. Glycine may be provided in various forms, for example, alone or in combination with other substances, such as in dietary supplements. Alternatively, glycine can be derived from other sources, such as gelatin.

The tissue referred to in the invention can be a skeletal muscle.

In one aspect, the invention provides compositions for practicing the methods of the invention. Accordingly, one aspect of the invention contemplates a composition having one or more active ingredient, including beta-alanine, beta-alanylhistidine peptides (or analogues or derivatives thereof), creatine, insulin, insulin mimics or insulin-action modifiers, glycine, and carbohydrate, to carry out the methods of the invention. The invention further contemplates the use of multiple compositions formulated to provide one or more active ingredient to the body for carrying out the methods of the invention.

Therefore, in an exemplary aspect, the invention features a composition consisting essentially of beta-alanine or a peptide source of beta-alanine, between about 39 and about 99 percent by weight of a carbohydrate, and up to about 60 percent by weight of water. The composition can include between about 0.1 and about 20 percent by weight of the beta-alanine (in the free or a bound form). The composition can include between about 0.1 and about 20 percent by weight of L-histidine.

The carbohydrate can be a simple carbohydrate (e.g., glucose).

In another aspect, the invention features a composition consisting essentially of beta-alanine or a peptide source of beta-alanine, between about 1 and about 98 percent by weight of a creatine source, and up to about 97 percent by weight of water. The composition includes between about 0.1 and about 98 percent by weight of the beta-alanine. The peptide source can include L-histidine and the composition can include between about 0.1 and about 98 percent by weight of L-histidine from this source.

The peptide source can be a mixture of amino acids, dipeptides, oligopeptides, polypeptides, or active derivatives thereof.

The composition can be a dietary supplement. The creatine source can be creatine monohydrate.

The concentrations of components in blood or blood plasma, including beta-alanine, can be increased by infusion (i.e., injection) or ingestion of an agent operable to cause an increase in the blood plasma concentration. The composition can be ingested in doses of between about 100 milligrams and about 800 grams or more per day. The doses can be administered in one part or multiple parts each day.

An increase of creatine and beta-alanylhistidine dipeptides in the muscles can increase the tolerance of the cells to an increase in hydronium ion production with anaerobic work and lead to an increase in endurance during exercise before the onset of fatigue. The compositions and methods can contribute to correcting the loss of beta-alanine, L-histidine, or creatine due to degradation or leaching of these constituents during the cooking or processing of food. The compositions and methods can also contribute to correcting the absence of these components from a vegetarian diet.

The methods and compositions can be used to increase beta-alanylhistidine dipeptides in sportsmen, athletes, bodybuilders, synchronized swimmers, soldiers, elderly people, horses in competition, working and racing dogs, and game birds, to avoid or delay the onset of muscular fatigue.

The details of one or more embodiments of the invention are set forth in the accompanying drawings and the description below. Other advantages and features of the invention will be apparent to the skilled artisan from the detailed description, drawings, and claims.

All publications, patents, patent applications cited herein are hereby expressly incorporated by reference for all purposes.

DESCRIPTION OF DRAWINGS

FIG. 17 illustrates a table of data, described in detail as Table 9, below.

Like reference symbols in the various drawings indicate like elements.

DETAILED DESCRIPTION

Figure 1:
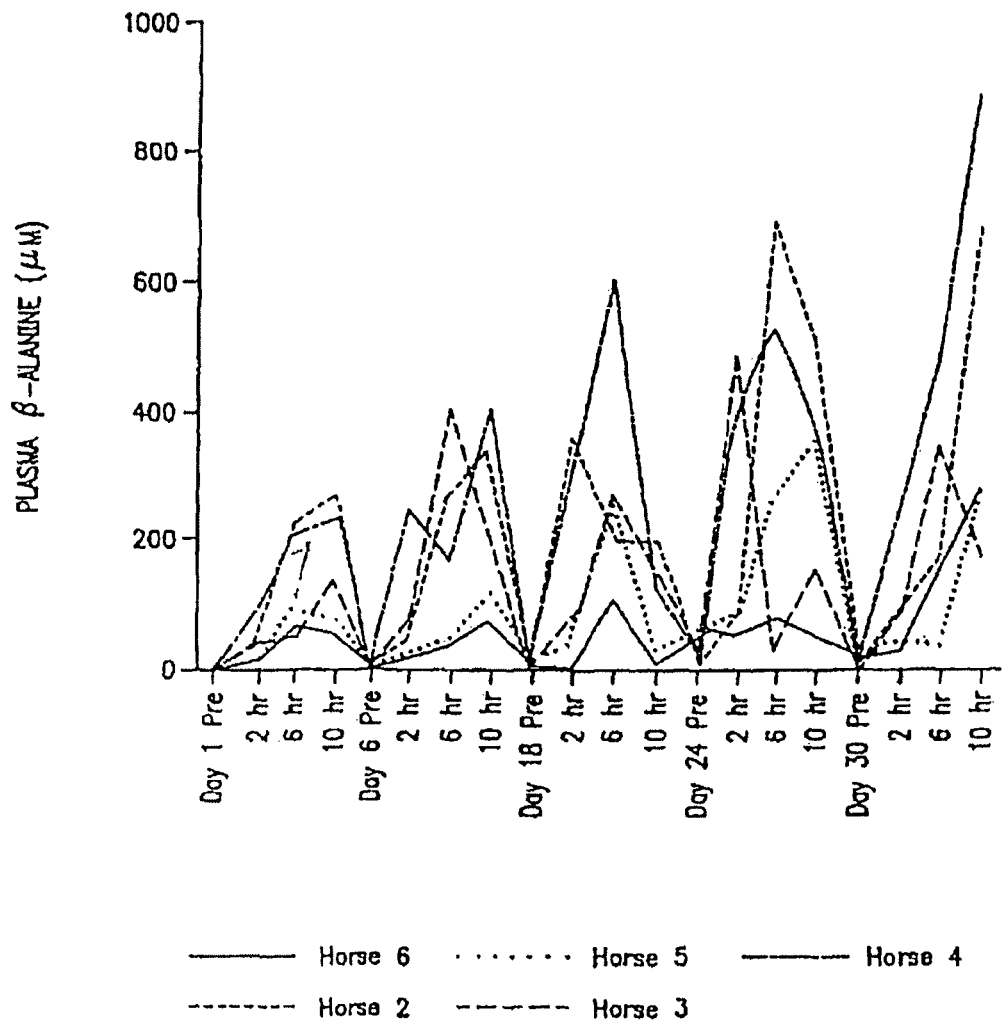
FIG. 1 is a graph depicting changes in the concentrations of beta-alanine in blood plasma of five horses, before and at 2 hour intervals following the feeding of beta-alanine and L-histidine (100 milligrams per kilogram body weight and 12.5 milligrams per kilogram body weight, respectively, three times per day) over a period of 30 days.

The invention provides compositions comprising beta-alanine, peptides of beta-alanine, analogues and derivatives thereof, beta-alanylhistidine dipeptides (e.g., carnosine, anserine, and balenine) and methods using these compositions for increasing the anaerobic working capacity of a tissue comprising providing an amount of beta-alanine to blood or blood plasma effective to increase beta-alanylhistidine dipeptide synthesis in a tissue. Beta-alanylhistidine dipeptides can include peptides of beta-alanine, such as carnosine, anserine, and balenine. In one aspect, they can have pKa values between approximately 6.8 and 7.1. In one aspect, they can be involved in the regulation of intracellular pH homeostasis during muscle contraction and the development of fatigue. The content of other substances involved in hydronium ion buffering, such as amino acid residues in proteins, inorganic and organic phosphates and bicarbonate, can be constrained by their involvement in other cell functions. In one aspect, the beta-alanylhistidine dipeptides provide an effective way of accumulating pH-sensitive histidine residues into a cell. Variations in the muscle beta-alanylhistidine dipeptide concentrations affect the anaerobic work capacity of individual athletes.

The beta-alanylhistidine dipeptides are synthesized within the body from beta-alanine and L-histidine. These precursors can be generated within the body or are made available via the diet, including from the breakdown of an ingested beta-alanylhistidine dipeptide. Within the body, beta-alanine is transported to tissues such as muscle. In a typical fed state, the concentration of beta-alanine is low in comparison with the concentration of L-histidine in human and equine blood plasma. These concentrations should be viewed in relation to the affinity of the carnosine synthesizing enzyme, carnosine synthetase, for its substrates as determined by the Michaelis-Menten constant (Km). The Km for histidine is about 16.8 µM. The Km for beta-alanine is between about 1000 and 2300 µM. The low affinity of carnosine synthetase for beta-alanine, and the low concentration of beta-alanine in muscle, demonstrate that the concentration of beta-alanine in muscle is limiting to the synthesis of the beta-alanylhistidine dipeptides.

Increasing the amount of beta-alanylhistidine dipeptides within a muscle favorably affects muscular performance and the amount of work that can be performed by the muscle. Accordingly, it is desirable to increase the synthesis and accumulation of beta-alanylhistidine dipeptides in a tissue in a human or animal body.

The synthesis and accumulation of beta-alanylhistidine dipeptides in a human or animal body can be increased by increasing creatine within the body, increasing the blood or blood plasma concentrations of beta-alanine, increasing the blood or blood plasma concentrations of beta-alanine and creatine, or increasing the blood or blood plasma concentrations of beta-alanine, L-histidine, and creatine. The increase in dipeptides can be simultaneous with the increase in beta-alanine concentrations.

In one aspect, the compositions and methods of the invention can be used to increase blood plasma concentrations of beta-alanine, L-histidine and/or creatine by ingestion or infusion of beta-alanine, peptides of beta-alanine, L-histidine, creatine, carnosine, anserine, and/or balenine and/or active derivatives or analogs thereof alone or in various combinations. The compositions of the invention can be administered orally, enterally, or parenterally. For example, compositions of the invention can be orally ingested or infused through the skin through a topical cream or a patch.

The composition can include carbohydrates (e.g., simple carbohydrates), insulin, or agents that stimulate the production of insulin. Compositions can also include glycine, insulin, insulin mimics, and/or insulin-action modifies.

The compositions can be a dietary supplement that can be ingested, injected, or absorbed through the skin. Preferably, the compositions can be administered in one or more doses per day. The beta-alanine dosage can be between about 1 milligram and about 200 milligrams per kilogram body weight or the dose of a peptide of beta-alanine (e.g. carnosine) from 2.5 milligrams to 500 milligrams per kilogram body weight. In one aspect, the total amount of beta-alanine (or other composition of the invention) administered can be at least 200 mg, from 200 mg to 5 g, or from 5 g or more per day for a human. A single dose of active ingredient, e.g., beta-alanine, carnosine, anserine, or balenine, or mixtures thereof, may be formulated to be in the amount about 200, 400, 800 mg or more. The creatine (e.g., creatine monohydrate) dosage, or dosage of other compositions of the invention, can be between about 5 milligrams to 200 milligrams per kilogram body weight. The L-histidine dosage, or dosage of other compositions of the invention, can be between about 1 milligram to 100 milligrams per kilogram body weight. The simple carbohydrate (e.g., glucose) dosage, or dosage of compositions of the invention, can be between about 0.5 and 2.0 grams per kilogram body weight.

In an 80 kilogram person, suitable dosages per day can be between 0.08 grams to 16.0 grams of beta-alanine or 200 milligrams to 40 grams of a peptide of beta-alanine, 0.4 grams to 16.0 grams of creatine monohydrate, 0.08 grams to 8.0 grams of L-histidine, or 40 grams to 160 grams of glucose or other simple carbohydrate. The composition can be in a solid form or a liquid form or in a suspension which can be ingested or infused into the body. The composition can be ingested by humans in an amount of between 0.08 grams and 1000 grams or more per day, which may be taken in one or more parts throughout the day. In animals, the daily intake will be adjusted by body weight.

In one aspect, the total amount of a peptide of beta-alanine, for example, carnosine, anserine or balenine that can be administered per day may be at least 500 mg, between about 500 mg to about 5 g, between about 5 g to about 16 g, or greater than 16 g. A single dose of a peptide of beta-alanine creatine, anserine or balenine, or mixtures thereof, may be formulated to be in the amount of 0.5, 1, 1.5, or 2 g (for each, or all, or the peptides in a formulation comprising a mixture).

For humans and animals, the compositions can be:
(a) 1% to 99% by weight of beta-alanine or 1% to 99% by weight of a peptide of beta-alanine;
    1% to 99% by weight of creatine monohydrate; and
    0% to 98% by weight of water;
(b) 1% to 98% by weight of beta-alanine or 1% to 98% by weight of a peptide of beta-alanine;
    1% to 98% by weight of L-histidine;
    1% to 98% by weight of creatine monohydrate; and
    0% to 97% by weight of water;
(c) 1% to 20% by weight of beta-alanine or 1% to 20% by weight of a peptide of beta-alanine;
    39% to 99% by weight of glucose or other simple carbohydrate; and
    0% to 60% by weight of water; or
(d) 1% to 20% by weight of beta-alanine or 1% to 20% by weight of a peptide of beta-alanine;
    1% to 20% by weight of L-histidine;
    39% to 99% by weight of glucose or other simple carbohydrate; and
    0% to 60% by weight of water.

In one aspect, compositions are applied to a body for at least three days, from 3 days to 2 weeks, from 2 weeks to 4 weeks, or longer. In certain regimens, the daily dosages are gradually increased or decreased. This can be done daily, every couple of days, or weekly.

EXAMPLES

The following are specific examples of the methods and compositions for increasing the anaerobic working capacity of muscle and other tissues.

Example 1

The effect of supplementation of a normal diet with multiple daily doses of beta-alanine and L-histidine on the carnosine concentration in type I, IIA, and IIB skeletal muscle fibers of thoroughbred horses was assessed. Six experimental thoroughbred horses of normal health (three fillies and three geldings), aged 4 to 9 years, underwent one month (30 days) of dietary conditioning (pre-supplementation period) prior to the commencement of the supplementation period. During the dietary conditioning period each horse was fed a diet comprising 1 kilogram of pelleted feed (Spillers racehorse cubes) and 1 kilogram of soaked sugar beet pulp as a source of complex and simple carbohydrates, three times per day (at 08:30, 12:30, and 16:30, respectively). Soaked hay (3 kilograms dry weight) was also provided twice daily (at 09:00 and 17:00). Water was provided ad libitum.

During the supplementation period, an identical feeding regime was implemented. However, each hard feed meal was supplemented with beta-alanine and L-histidine (free base). Beta-alanine and L-histidine were mixed directly into the normal feed. Individual doses of beta-alanine and L-histidine were calculated according to body weight. Beta-alanine was administered at 100 milligrams per kilogram body weight and L-histidine at 12.5 milligrams per kilogram body weight. Dietary supplementation was begun on day 1 of the protocol and discontinued at the end of day 30. Heparinized blood samples (5 milliliters) were collected on days 1, 6, 18, 24, and 30. On day 1 and day 30, blood samples were collected prior to the first feed and at hourly intervals for a total of 12 hours each day. On the three intervening sampling days, blood was collected prior to the first feed and 2 hours after each subsequent feed. On the day before the start of supplementation (day 0) a muscle biopsy was taken, following application of local anesthesia of the skin, from the right middle gluteal muscle (m. gluteus medius) of each horse using a Bergstrom-Stille percutaneous biopsy needle. Subsequent muscle biopsies were collected immediately after the end of the supplementation period (day 31) as close as possible to the original sampling site. Clinical monitoring of the horses was performed daily. This comprised a visual examination and measurement of body weight, twice-daily measurement of rectal temperature, and weekly blood sampling for clinical biochemistry and hematology. During the course of the study, the horses received no formal training or exercise, although they were allowed one hour of free exercise each day.

Fragments of individual muscle fibers dissected from freeze-dried muscle biopsies were characterized as either type I, IIA or IIB by histochemical staining for myosin ATPase activity at pH 9.6 following pre-incubation at pH 4.5 by a modification of the method described in, Kaiser and Brook, *Arch. Neural.*, 23:369-379 (1970).

Heparinized blood plasma samples were extracted and analyzed for beta-alanine and L-histidine concentrations by high-performance liquid chromatography (HPLC). Individual weighed muscle fibers were extracted and analyzed for carnosine by HPLC according to the method described in, Dunnett and Harris, "High-performance liquid chromatographic determination of imidazole dipeptides, histidine, 1-methylhistidine and 3-methylhistidine in muscle and individual muscle fibers,"*J. Chromatogr. B. Biomed. Appl.*, 688:47-55 (1997).

Differences in carnosine concentrations within fiber types before and after supplementation were established within horses using one-way analysis of variance (ANOVA). In instances where differences were detected, significance was determined using a multiple comparison test (Fisher's PLSD).

No palatability problems were encountered with the addition of beta-alanine and L-histidine to the feed. No adverse physiological or behavioral effects of the supplemented diet were observed in any of the horses during the thirty days of supplementation. No significant changes in body weight were recorded, and rectal temperatures remained within the normal range. No acute or chronic changes in clinical biochemistry or hematology were observed. Beta-alanine was not detected in the plasma of any of the horses prior to the start of supplementation. The lower limit of quantitation for beta-alanine in plasma by the assay used was 3 micromolar ($\mu$M). Plasma L-histidine concentrations in the six horses prior to the start of supplementation were between 36.6 and 54.4 $\mu$M.

Figure 2:
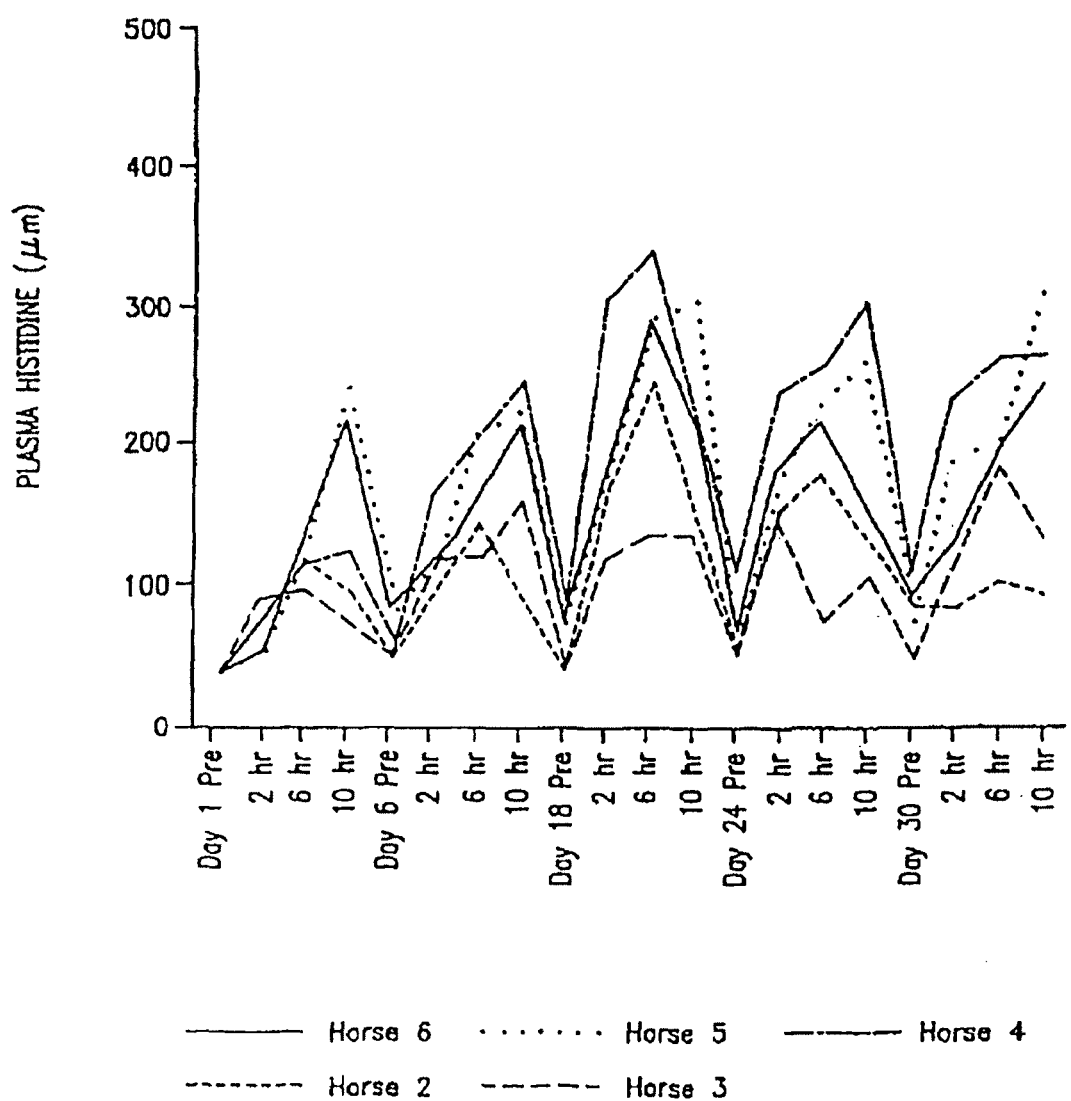
FIG. 2 is a graph depicting changes in the concentrations of L-histidine in blood plasma of five horses, before and at 2 hour intervals following the feeding of beta-alanine and L-histidine (100 milligrams per kilogram body weight and 12.5 milligrams per kilogram body weight, respectively, three times per day) over a period of 30 days.
Figure 3A:
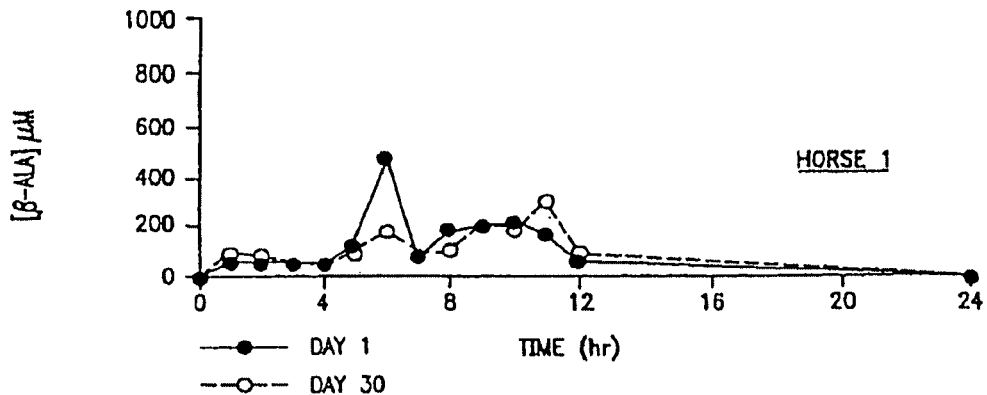
FIGS. 3a, 3b, 3c, 3d, 3e and 3f are graphs depicting the contrast in the changes in the concentrations of beta-alanine in blood plasma of six horses, before and at hourly intervals following the feeding of beta-alanine and L-histidine, as described in detail, below.
Figure 3B:
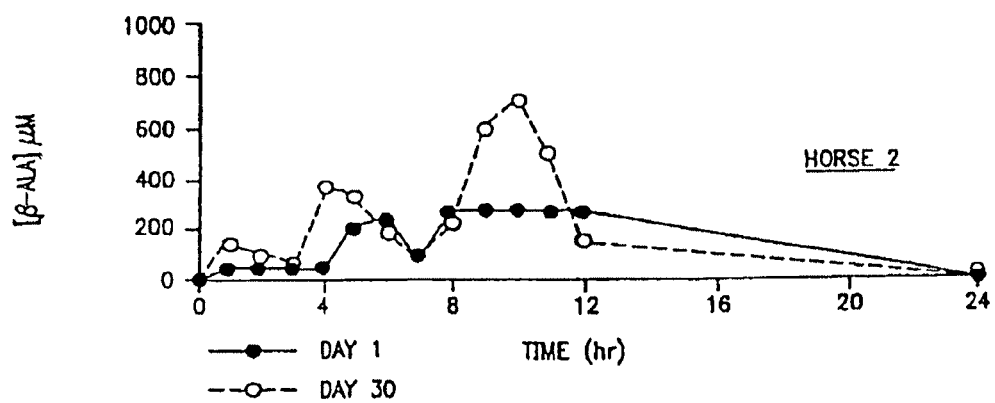
Figure 3C:
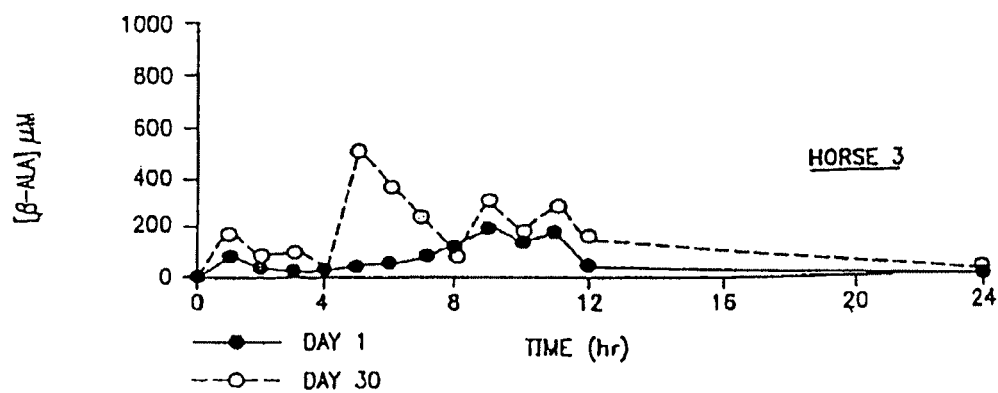
Figure 3D:
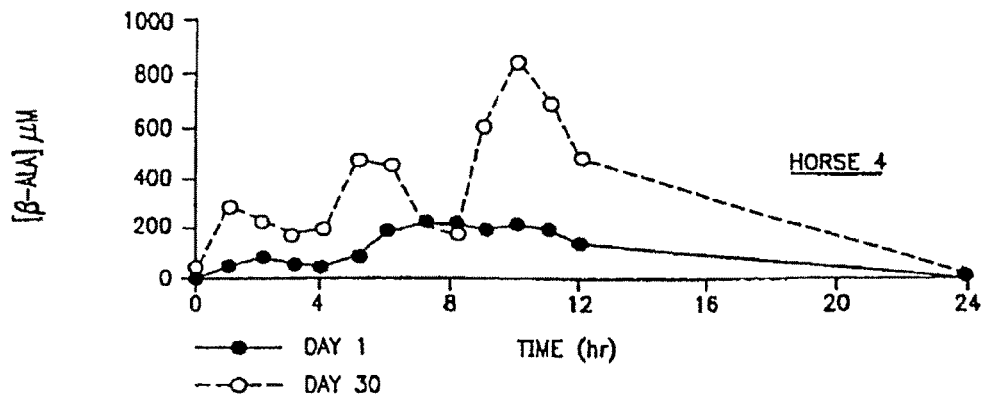
Figure 3E:
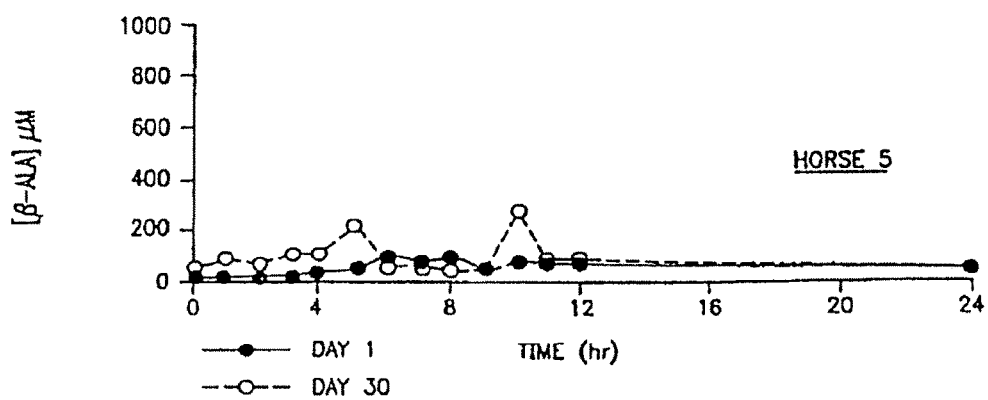
Figure 3F:
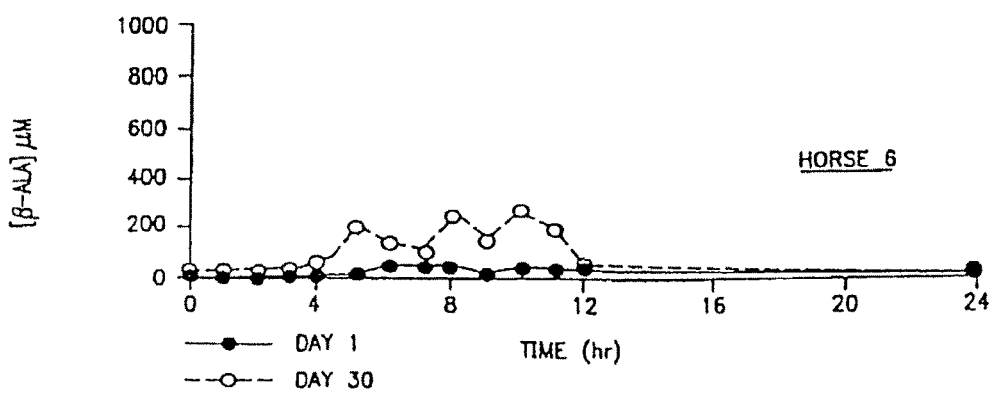
Figure 4A:
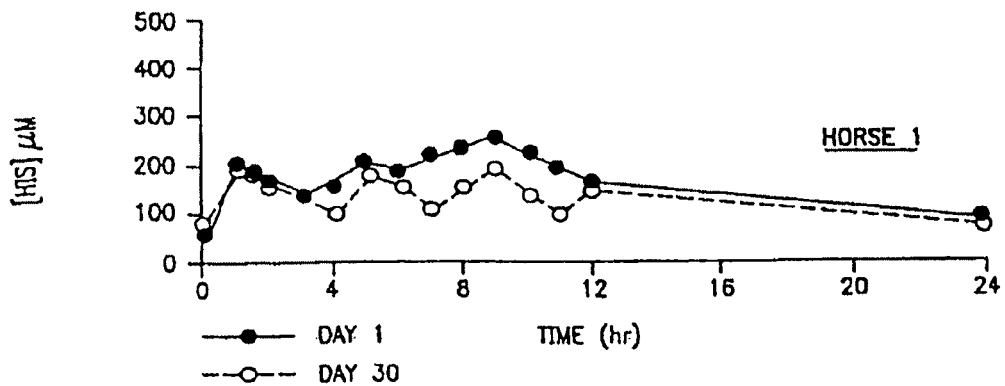
FIGS. 4a, 4b, 4c, 4d, 4e and 4f are graphs depicting the contrast in the changes in the concentrations of L-histidine in blood plasma of six horses, before and at hourly intervals following the feeding of beta-alanine and L-histidine, as described in detail, below.
Figure 4B:
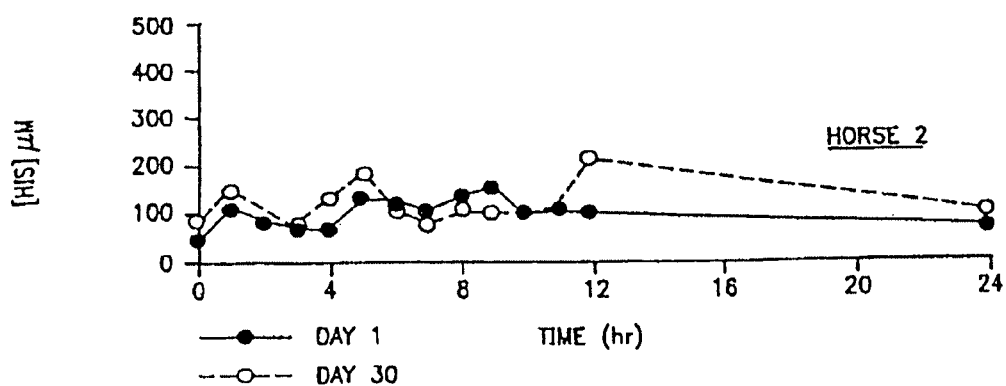
Figure 4C:
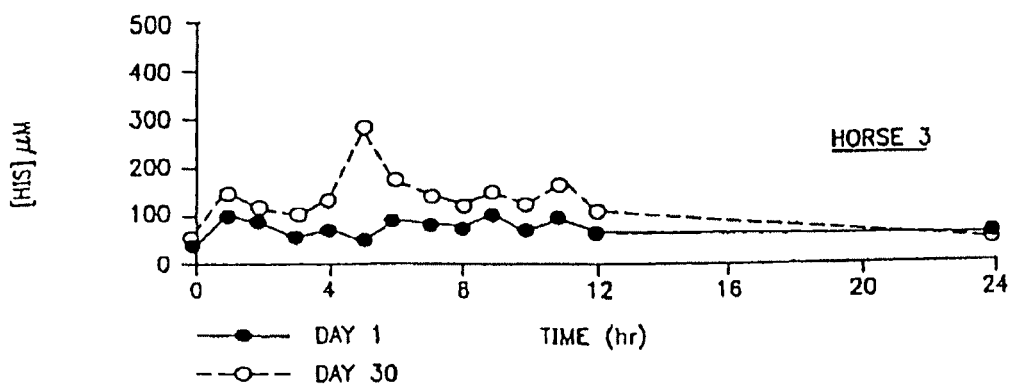
Figure 4D:
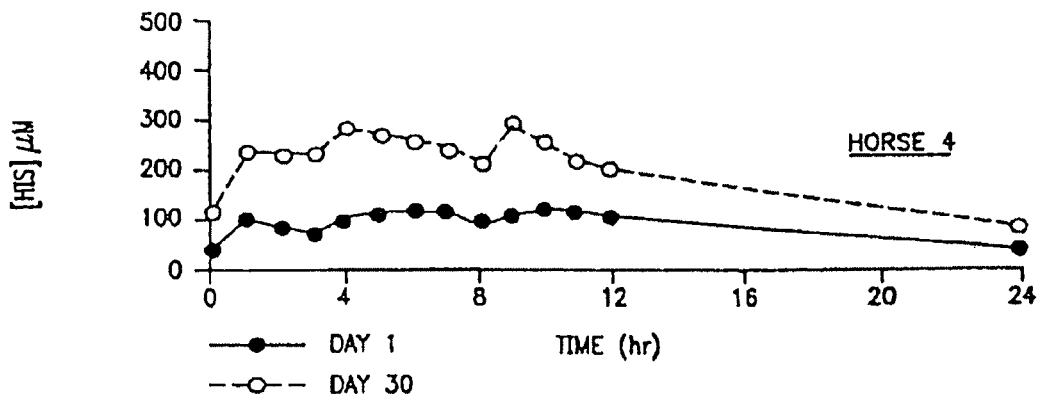
Figure 4E:
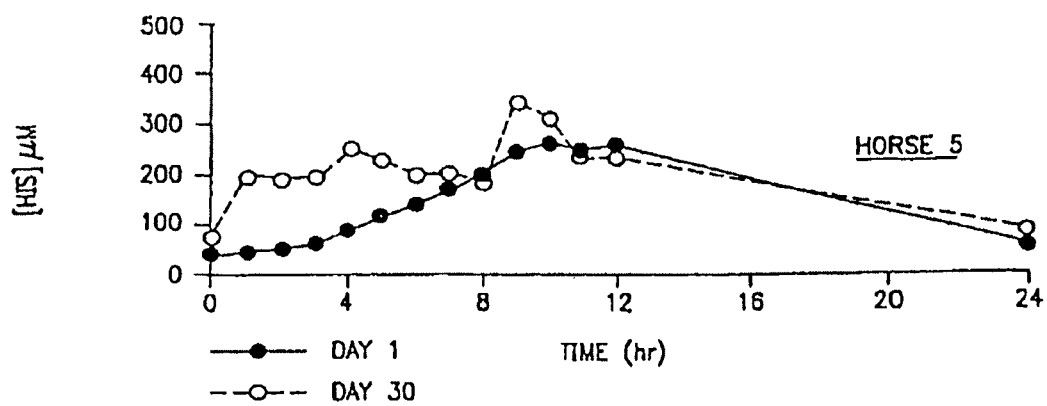
Figure 4F:
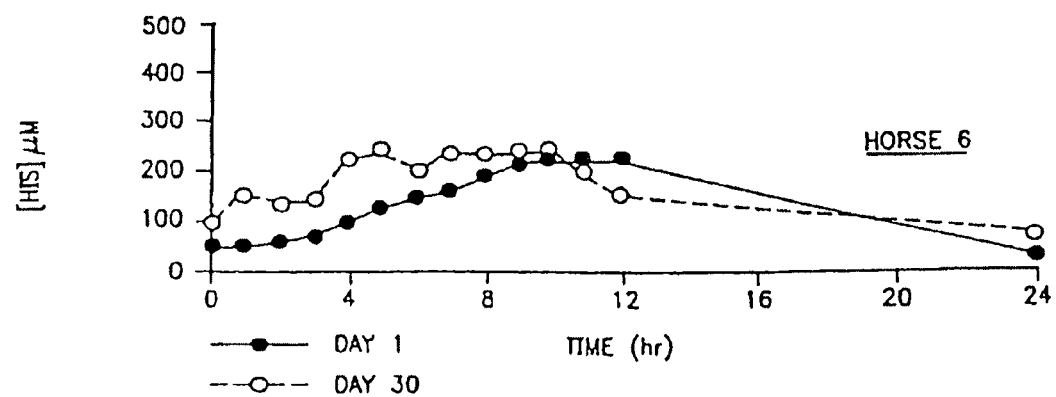

Individual changes in blood plasma beta-alanine and L-histidine concentrations for five of the six horses over all the sampling days are shown in FIGS. 1 and 2, respectively. There was a trend towards an increase in the pre-feeding concentrations of blood plasma beta-alanine and L-histidine with increasing time of supplementation. Furthermore, over the thirty day supplementation period, the blood plasma concentration response to supplementation was also increased. The response was greater for beta-alanine.

Figure 5:
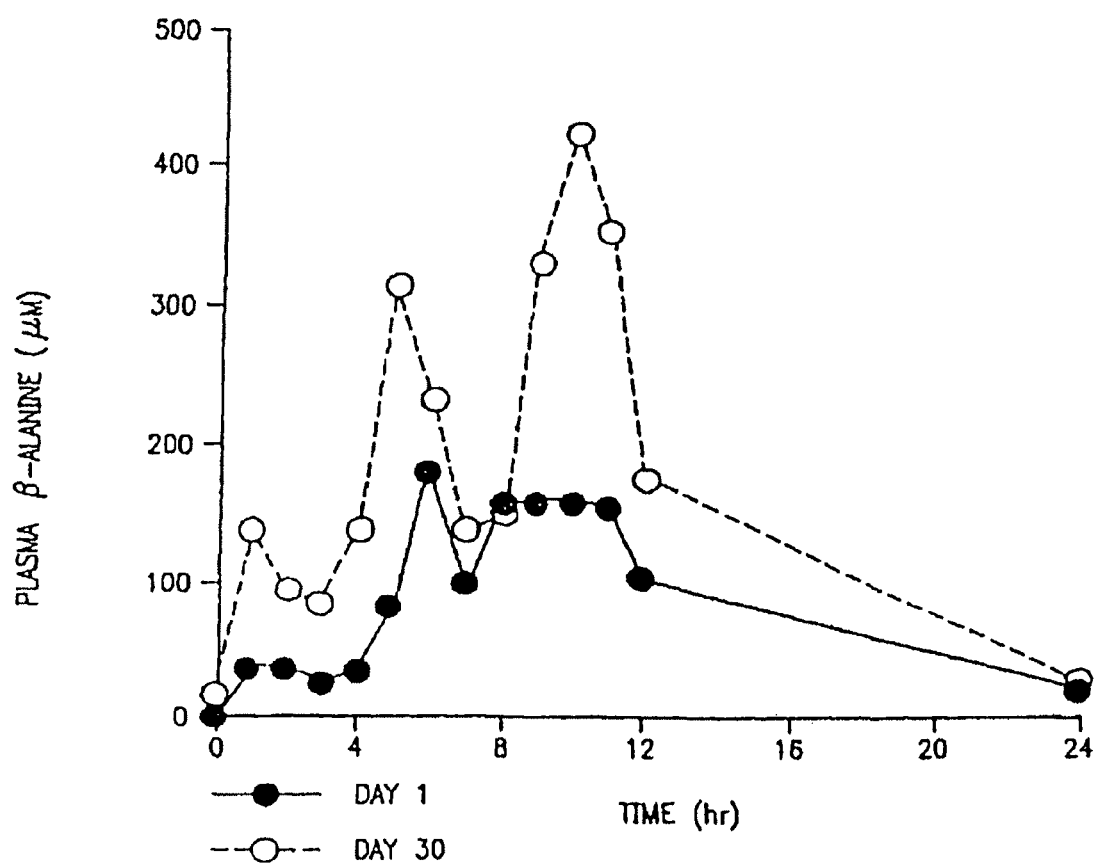
FIG. 5 is a graph depicting the contrast in the changes in the mean concentrations of beta-alanine in equine blood plasma (n=6), before and at hourly intervals following the feeding of beta-alanine and L-histidine, as described in detail, below.

Comparisons of the changes in blood plasma beta-alanine and L-histidine concentrations prior to the first feed of the day, and hourly thereafter between the first and last days of the supplementation period, for the six individual horses, are shown in FIGS. 3a and 3b, and FIGS. 4a and 4b, respectively. FIGS. 3a, 3b, 3c, 3d, 3e and 3f are graphs depicting the contrast in the changes in the concentrations of beta-alanine in blood plasma of six horses, before and at hourly intervals following the feeding of beta-alanine and L-histidine (100 milligrams per kilogram body weight and 12.5 milligrams per kilogram body weight, respectively, three times per day) on the first and last day of a 30 day period of dietary supplementation. FIGS. 4a, 4b, 4c, 4d, 4e and 4f are graphs depicting the contrast in the changes in the concentrations of L-histidine in blood plasma of six horses, before and at hourly intervals following the feeding of beta-alanine and L-histidine (100 milligrams per kilogram body weight and 12.5 milligrams per kilogram body weight, respectively, three times per day) on the first and last day of a 30 day period of dietary supplementation. FIG. 5 is a graph depicting the contrast in the changes in the mean concentrations of beta-alanine in equine blood plasma (n=6), before and at hourly intervals following the feeding of beta-alanine and L-histidine (100 milligrams per kilogram body weight and 12.5 milligrams per kilogram body weight, respectively, three times per day) on the first and last day of a 30 day period of dietary supplementation. The mean (SD) changes (n=6) in blood plasma beta-alanine concentration over time during the 24 hours of the first (day 1) and last (day 30) days of the supplementation period are contrasted in FIG. 5. The area under the mean blood plasma beta-alanine concentration versus time curve over 24 hours ($AUC_{(0-24hr)}$) was much greater on day 30 of the supplementation.

Figure 6:
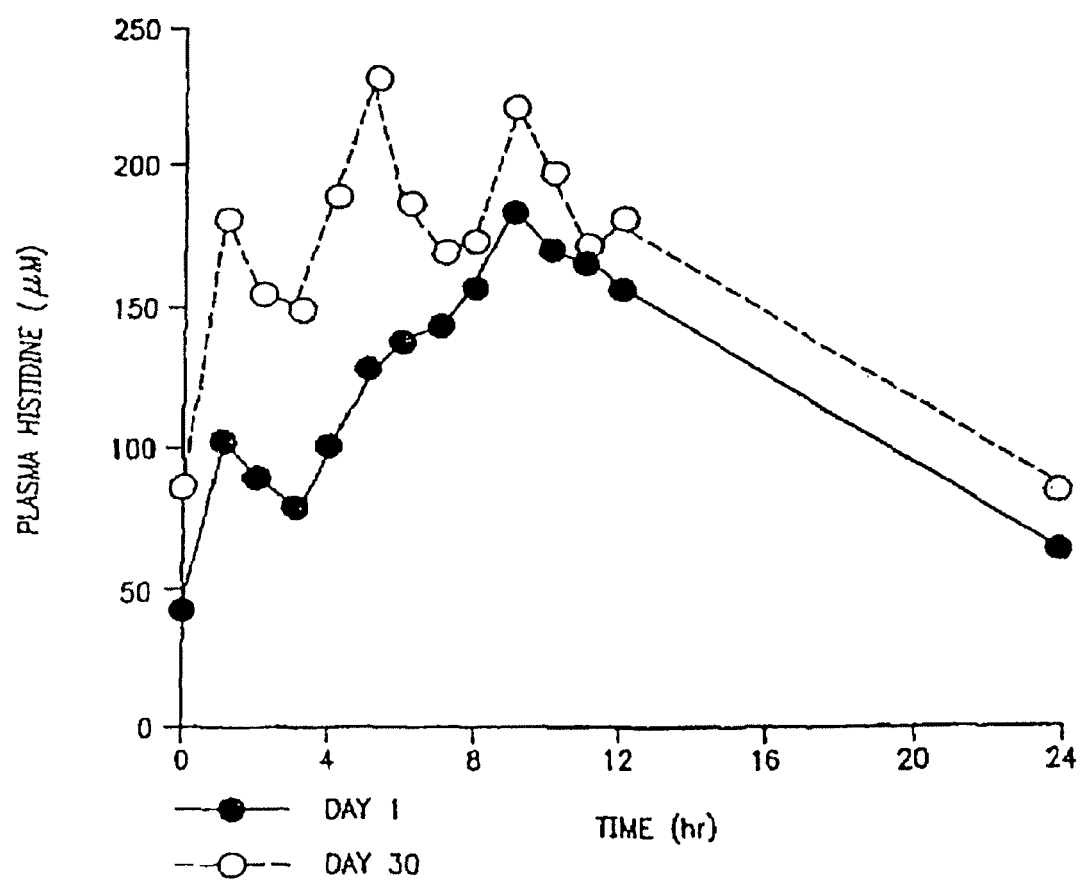
FIG. 6 is a graph depicting the contrast in the changes in the mean concentrations of L-histidine in equine blood plasma (n=6), before and at hourly intervals following the feeding of beta-alanine and L-histidine (100 milligrams per kilogram body weight and 12.5 milligrams per kilogram body weight, respectively, three times per day) on the first and last day of a 30 day period of dietary supplementation.

The mean (SD) changes (n=6) in blood plasma L-histidine concentration over time during the 24 hours of the first (day 1) and last (day 30) days of the supplementation period are contrasted in FIG. 6. The area under the mean blood plasma beta-alanine concentration vs. time curve over 24 hours ($AUC_{(0-24hr)}$) was greater on day 30 of the supplementation. The greater AUC for blood plasma beta-alanine on the last day of supplementation (day 30) in contrast to the first day of supplementation (day 1) suggests the increased uptake of beta-alanine from the equine gastro-intestinal tract with progressive supplementation. A similar effect was observed for changes in blood plasma L-histidine concentration during the supplementation period. Peak blood plasma concentrations of beta-alanine and L-histidine occurred approximately one to two hours post-feeding in each case.

A total of 397 individual skeletal muscle fibers (192 pre-supplementation; 205 post-supplementation) from the six horses were dissected and analyzed for carnosine. Mean (SD) carnosine concentration, expressed as millimoles per kilogram dry weight (mmol $kg^{-1}$ dw), in pre- and post-supplementation type I, IIA, and IIB skeletal muscle fibers from the six individual horses are given in Table 1 where n is the number of individual muscle fibers analyzed. Following thirty days of beta-alanine and L-histidine supplementation the mean carnosine concentration was increased in type IIA and IIB fibers in all six horses. These increases were statistically significant in seven instances. The increase in mean carnosine concentration in type IIB skeletal muscle fibers was statistically significant in five out of six horses. The increase in mean carnosine concentration in type IIA skeletal muscle fibers was statistically significant in two out of six horses.

TABLE 1

| Horse | Day | Type 1 | n | Type IIA | n | TypeIIB | n |
|---|---|---|---|---|---|---|---|
| 6 | 0 | 32.3 (14.5) | 3 | 72.1 (47.7) | 11 | 111.8 (22.8) | 14 |
|   | 31 |  |  | 16.2 (20.9) | 17 | 117.7 (38.7) | 12 |
| 5 | 0 | 59.5 (3.9) | 2 | 102.6 (12.7) | 12 | 131.2 (26.6) | 26 |
|   | 31 | 55.5 | 1 | 112.2 (17.1) | 18 | 153.3 (28.0)** | 22 |
| 4 | 0 | 44.8 (6.6) | 4 | 59.9 (19.5) | 13 | 108.6 (41.5) | 19 |
|   | 31 | 37.0 (9.3) | 2 | 88.0 (34.2)* | 17 | 152.4 (65.0)* | 19 |
| 1 | 0 | 56.7 (5.3) | 2 | 88.5 (20.9) | 15 | 101.3 (15.2) | 13 |
|   | 31 | 57.8 | 1 | 96.1 (17.3) | 19 | 14.3 (13.3)* | 11 |
| 2 | 0 | — | 4 | 89.6 (16.2) | 13 | 104.2 (22.2) | 14 |
|   | 31 | 65.9 (13.2) |  | 102.2 (22.1) | 18 | 142.0 (35.4)*** | 12 |
| 3 | 0 | 30.9 (4.0) | 2 | 85.1 (20.3) | 6 | 113.5 (20.4) | 23 |
|   | 31 | — |  | 105.0 (17.6)* | 23 | 135.4 (24.9)* | 9 |
| Mean | 0 | 44.8 | 13 | 83.0 | 70 | 111.8 | 109 |
|   | 31 | 54.1 | 8 | 96.6* | 112 | 135.9** | 85 |

*significantly different to pre-supplementation, p < 0.05
**significantly different to pre-supplementation, p < 0.01
***significantly different to pre-supplementation, p < 0.005

The absolute (e.g. mmol kg$^{-1}$ dw) and percentage increases in the mean carnosine concentrations in type IIA and IIB skeletal muscle fibers from the six horses are listed in Table 2.

TABLE 2

| Horse | Type IIA Absolute increase | Type IIA % increase | Type IIB Absolute increase | Type IIB % increase |
|---|---|---|---|---|
| 6 | 4.1 | 5.7 | 5.6 | 5.3 |
| 5 | 9.6 | 9.4 | 22.1 | 16.8 |
| 4 | 28.1 | 46.9 | 43.8 | 40.3 |
| 1 | 7.6 | 8.6 | 13.0 | 12.8 |
| 2 | 12.6 | 14.1 | 37.8 | 36.3 |
| 3 | 19.9 | 23.4 | 21.9 | 19.3 |
| Mean | 13.6 | 18.0 | 24.1 | 21.8 |

Figure 7:
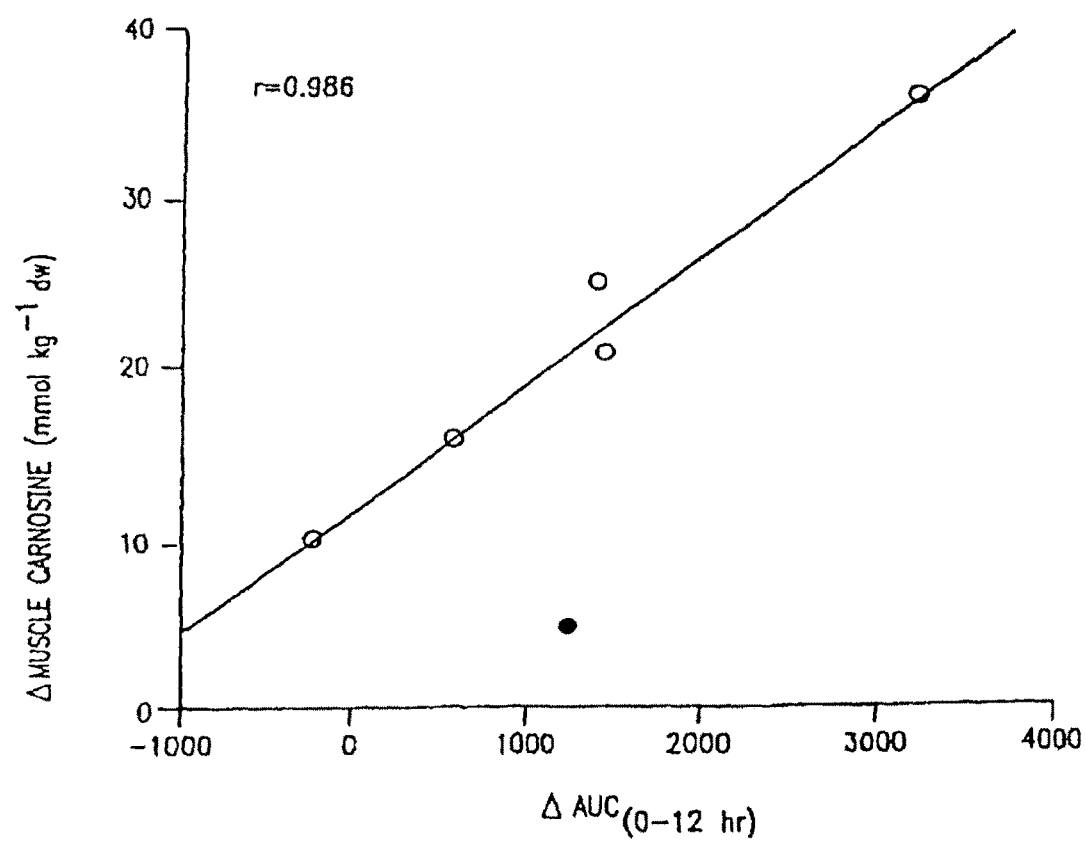
FIG. 7 is a graph depicting the correlation between the increase in 6 thoroughbred horses in the carnosine concentration in type II skeletal muscle fibers (the average of the sum of type IIA and IIB fibers) and the increase, between the 1st and 30th day of supplementation, in the area under the blood plasma beta-alanine concentration-time curve over the first 12 hours of the day ($AUC_{(0-12\ hr)}$).

It was observed that the individual horses which showed the greater increase in muscle carnosine concentration following thirty days of supplementation also demonstrated the greater increase in blood plasma beta-alanine AUC between day 1 and day 30 of the supplementation period. Referring to FIG. 7, a significant correlation (r=0.986, p<0.005) for five of the six horses was observed between the increase in mean carnosine concentration, averaged between type IIA and IIB skeletal muscle fibers and the increase, between the 1st and 30th day of supplementation, in blood plasma beta-alanine AUC, over the first 12 hours ($AUC_{(0-12hr)}$). Only five horses were used to calculate the regression line. Horse 6 (filled circle) showed no appreciable increase in blood plasma beta-alanine concentration greater than that observed on day 1 until the last day of supplementation. This was unlike the other five horses, which showed a progressive increase with each sampling day. For this reason horse 6 was excluded from the calculation of the regression equation.

Increases in muscle carnosine concentration following thirty days of supplementation with beta-alanine and L-histidine will cause a direct increase in total muscle buffering capacity. This increase can be calculated by using the Henderson-Hasselbach Equation. Calculated values for the increases in muscle buffering capacity in type IIA and IIB skeletal muscle fibers in the six thoroughbred horses are shown in Table 3.

TABLE 3

| Horse | Day | Type IIA βmcar | Type IIA βmtotal | Type IIA Δβmtotal (%) | Type IIB βmcar | Type IIB βmtotal | Type IIB Δβmtotal (%) |
|---|---|---|---|---|---|---|---|
| 6 | 0 | 23.9 | 93.9 | +1.5 | 37.1 | 107.1 | +1.8 |
|   | 31 | 25.3 | 95.3 |  | 39.0 | 109.0 |  |
| 5 | 0 | 34.0 | 104.0 | +3.1 | 43.5 | 113.5 | +6.4 |
|   | 31 | 37.2 | 107.2 |  | 50.8 | 120.8 |  |
| 4 | 0 | 19.9 | 89.9 | +10.3 | 36.0 | 106.0 | +13.7 |
|   | 31 | 29.2 | 99.2 |  | 50.5 | 120.5 |  |
| 1 | 0 | 29.3 | 99.3 | +2.6 | 33.6 | 103.6 | +4.2 |
|   | 31 | 31.9 | 101.9 |  | 37.9 | 107.9 | +12.1 |
| 2 | 0 | 29.7 | 99.7 | +4.2 | 34.5 | 104.5 |  |
|   | 31 | 33.9 | 103.9 |  | 47.1 | 117.1 |  |
| 3 | 0 | 28.2 | 98.2 | +6.7 | 37.6 | 107.6 | +6.8 |
|   | 31 | 34.8 | 104.8 |  | 44.9 | 114.9 |  |
| Mean | 0 | 27.5 | 97.5 | +4.7 | 37.1 | 107.1 | +7.5 |
|   | 31 | 32.1 | 102.1 |  | 45.0 | 115.0 |  |

Example 2

The effect of supplementation of a normal diet with single and multiple daily doses of beta-alanine in free or peptide bound form on the beta-alanine and beta-alanyl dipeptide concentrations of plasma of humans was assessed. The plasma concentration of beta-alanine in six normal subjects following the consumption of a broth delivering approximately 40 milligrams per kilogram body weight of beta-alanine was monitored. Doses of 10 and 20 milligrams per kilogram body weight of beta-alanine were also given.

The broth was prepared as follows. Fresh chicken breast (skinned and boned) was finely chopped and boiled for fifteen minutes with water (1 liter for every 1.5 kg of chicken). Residual chicken meat was removed by course filtration. The filtrate was flavored by the addition of carrot, onion, celery, salt, pepper, basil, parsley and tomato puree, and reboiled for a further fifteen minutes and then cooled before final filtration through fine muslin at 4° C. The yield from 1.5 kilograms of chicken and one liter of water was 870 mL of broth. A portion of the stock was assayed for the total beta-alanyl-dipeptide content (e.g., carnosine and anserine) and beta-alanine. Typical analyses were:

| total beta-alanyl-dipeptides | 74.5 mM |
|---|---|
| free beta-alanine | 5.7 mM |

The six male test subjects were of normal health and between 25-53 years of age, as shown in Table 4. The study commenced after an overnight fast (e.g., a minimum of 12 hours after the ingestion of the last meat containing meal). Subjects were given the option to consume a small quantity of warm water prior to the start of the study. Catheterization was begun at 08:30 and the study started at 09:00.

As a control, 8 milliliters per kilogram body weight of water was ingested (e.g., 600 mL in a subject weighing 75 kilograms).

In one session, 8 milliliters per kilogram body weight of broth containing approximately 40 milligrams per kilogram body weight of beta-alanine (e.g., in the form of anserine and carnosine) was ingested. For a subject weighing 75 kilograms, this amounted to the ingestion of 600 milliliters of broth containing 3 grams of beta-alanine. In another session, 3 milliliters per kilogram body weight of a liquid containing the test amount of beta-alanine with an additional 5 milliliters per kilogram body weight of water was ingested. In all sessions, subjects additionally consumed a further 8 milliliters per kilogram body weight of water (in 50 mL portions) during the period of 1 to 2 h after ingestion. A vegetarian pizza was provided after 6 hours. An ordinary diet was followed after 8 hours.

2.5 milliliter venous blood samples were drawn through an indwelling catheter at 10 minute intervals for the first 90 minutes and then after 120, 180, 240 and 360 minutes. The blood samples were dispensed into tubes containing lithium-heparin as an anti-coagulant. The catheter was maintained by flushing with saline. Plasma samples were analyzed by HPLC according to the method described in Jones & Gilligan (1983) *J. Chromatogr.* 266:471-482 (1983).

Table 4 summarizes the allocation of treatments during the beta-alanine absorption study. The estimated equivalent doses of beta-alanine are presented in Table 4.

TABLE 4

| Subject | Age yrs | Weight kg | Broth 40 mg/kg bwt | β-ala 0 mg/kg bwt | β-ala 10 mg/kg bwt | β-ala 20 mg/kg bwt | β-ala 40 mg/kg bwt | Carnosine 20 mg/kg bwt |
|---|---|---|---|---|---|---|---|---|
| 1 | 53 | 76 | + |   |   | + | + | + |
| 2 | 33 | 60 | + |   |   | + | + |   |
| 3 | 29 | 105 | + | + | + | + |   |   |
| 4 | 31 | 81 | + | + | + |   | + |   |
| 5 | 30 | 94 | + | + | + |   | + |   |
| 6 | 25 | 65 | + | + | + | + |   |   |

Figure 8:
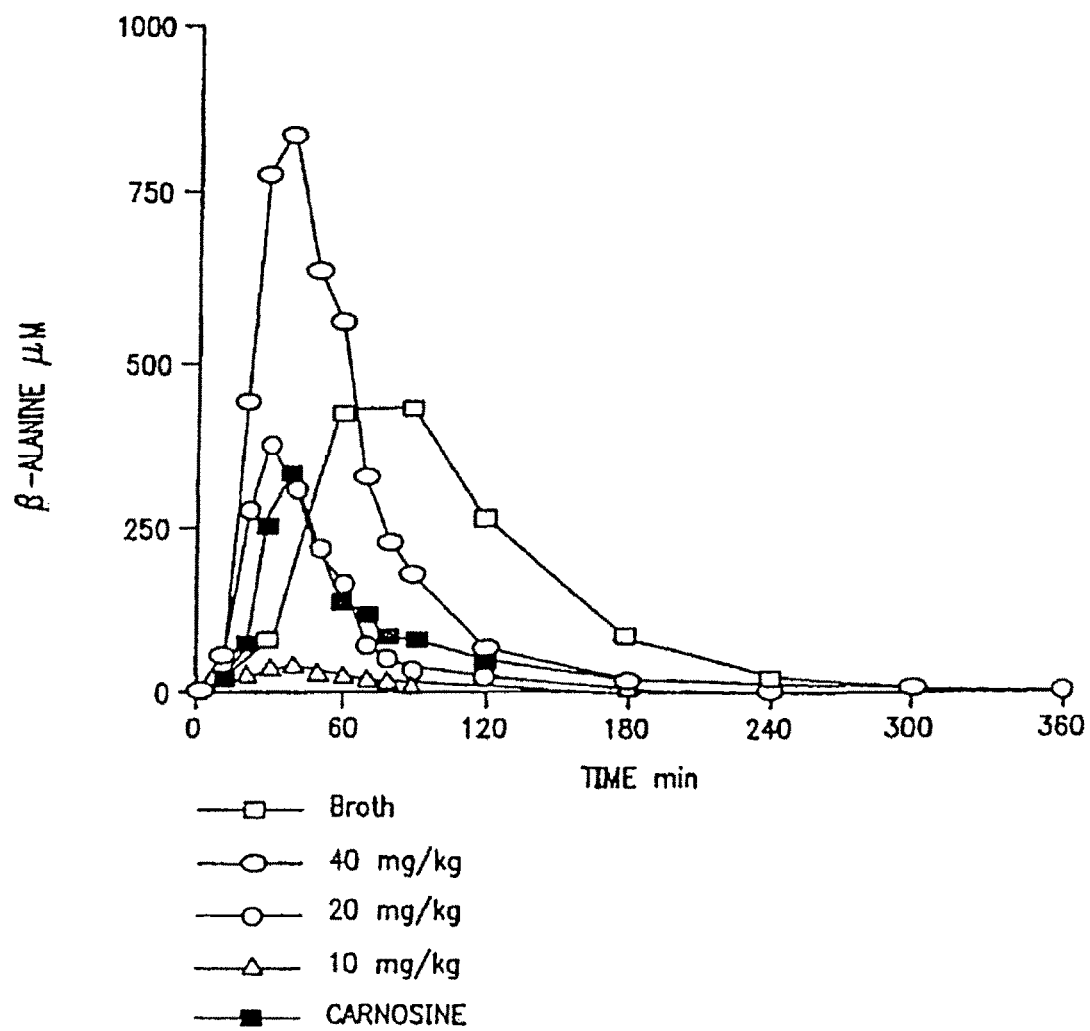
FIG. 8 is graph depicting the mean results of the administration of beta-alanine, broth, or carnosine to test subjects.

Plasma concentration curves following each treatment are depicted graphically in FIG. 8. Mean results of the administration of beta-alanine, broth, or carnosine according to the treatments schedule in Table 4. Plasma beta-alanine was below the limit of detection in all subjects on the control treatment. Neither carnosine or anserine were detected in plasma following ingestion of the chicken broth or any of the other treatments. Ingestion of the broth resulted in a peak concentration in plasma of 427.9 (SD 161.8) μM. Administration of carnosine equivalent to 20 milligrams per kilogram body weight of beta-alanine in one test subject resulted in an equivalent increase in the plasma beta-alanine concentration.

Administration of all treatments except control resulted in an increase in the plasma taurine concentration. The changes in taurine concentration mirrored closely those of beta-alanine. Administration of broth, a natural food, caused an equivalent increase in plasma taurine, indicating that the response occurs normally following the ingestion of most meals.

Example 3

The effect of administration of three doses of 10 milligrams per kilogram body weight of beta-alanine per day (i.e., administered in the morning, noon, and at night) for seven days on the plasma concentration profiles of beta-alanine and taurine were investigated. The plasma concentration profiles following administration of 10 milligrams per kilogram body weight of beta-alanine were studied in three subjects at the start and end of a seven-day period during which they were given three doses of the beta-alanine per day.

Three male subjects of normal health, aged between 33-53 years were studied. Test subjects received three doses per day of 10 milligrams per kilogram body weight of beta-alanine for eight days. In two subjects, this was followed by a further 7 days (days 9-15) when three doses of 20 milligrams per kilogram body weight per day were given. Subjects reported at 8 am to the blood collection laboratory on days 1 (prior to any treatment given), 8 and 15 following an overnight fast. Subjects were asked not to consume any meat containing meal during the 12 hours preceding the study. On each of these three test days subjects were catheterized and an initial blood sample taken when the beta-alanine was administered at or close to 9 am, 12 noon, and 3 pm. Blood samples were drawn after 30, 60, 120 and 180 minutes, and analyzed for changes in the plasma concentration of beta-alanine and taurine. 24-hour urine samples were collected over each day of the study and analyzed by HPLC to determine the excretion of beta-alanine and taurine. The treatments are summarized in Table 5.

TABLE 5

| Treatment Day beta-alanine | Day 1 10 mg/kg bwt | Day 8 10 mg/kg bwt | Day 15 20 mg/kg bwt |
|---|---|---|---|
| 1 | + | + | + |
| 2 | + | + | + |
| 3 | + | + |   |

Figure 9:
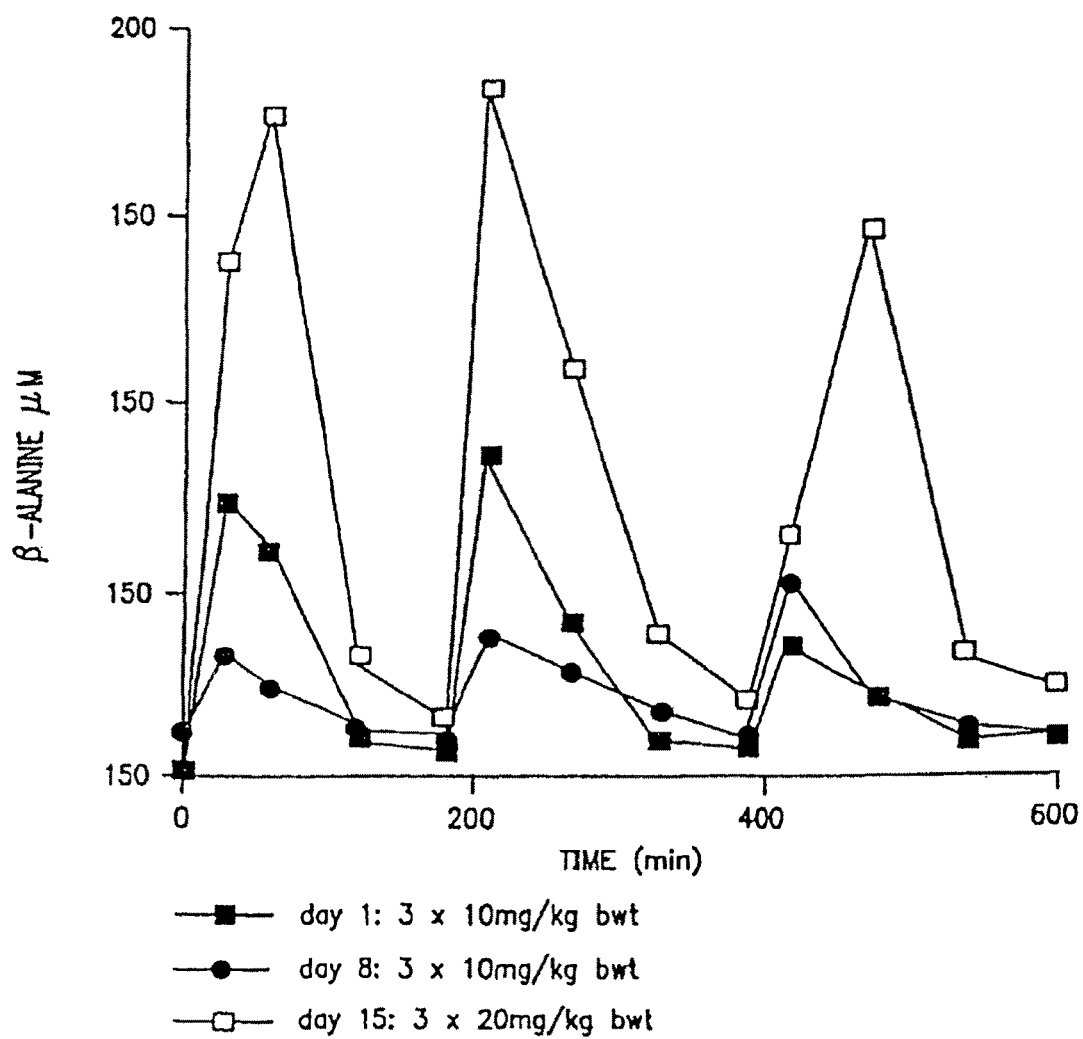
FIG. 9 is a graph depicting mean changes in plasma beta-alanine over nine hours of treatment.

The plasma beta-alanine concentrations are summarized in FIG. 9. Each dose resulted in a peak beta-alanine concentration at one-half hour or one hour after ingestion followed by a decline to a 0-10 micromolar basal level at three hours, just prior to administration of the next dose. The response on day 8 of the treatment tended to be less than on day 1, as indicated by the area under the plasma concentration curve.

Example 4

The effect of administration of three doses of 40 milligrams per kilogram body weight of beta-alanine per day (i.e., administered in the morning, noon, and at night) for 2 weeks on the carnosine content of muscle and isometric endurance at 66% of maximal voluntary contraction force was investigated.

Six normal male subjects, aged 25 to 32 years, that did not have evidence of metabolic or muscle disease were recruited into the study. The subjects were questioned regarding their recent dietary and supplementary habits. None of subjects was currently taking supplements containing creatine, or had done so in recent testing supplementation procedures. The physical characteristics of the test subjects are summarized in Table 6.

TABLE 6

| Subject | Age (years) | Weight (kg) |
|---|---|---|
| 1 | 29 | 78 |
| 2 | 31 | 94 |
| 3 | 29 | 105 |
| 4 | 25 | 65 |
| 5 | 31 | 81 |

TABLE 6-continued

| Subject | Age (years) | Weight (kg) |
|---|---|---|
| 6 | 25 | 75 |
| 7 | 53 | 76 |

Two days before treatment, a preliminary determination of maximal voluntary (isometric) contraction force (MVC) of knee extensors with the subject in the sitting position was carried out. MVC was determined using a Macflex system with subjects motivated by an instantaneous visual display of the force output. For each subject, two trials were carried out to determine endurance at 66% MVC sustained until the target force could no longer be maintained despite vocal encouragement. This first contraction was subsequently followed by a rest period of 60 seconds, with the subject remaining in the isometric chair. After the rest period, a second contraction was sustained to fatigue. Following a second rest of 60 seconds, a third contraction to fatigue was undertaken.

One day before treatment, the subjects reported to the isometric test laboratory between 8 and 10 am. MVC was determined and endurance at 66% MVC over three contractions with 60 second rest intervals, as described above, was determined. Measurements were determined using the subject's dominant leg. A biopsy of the lateral portion of the vastus lateralis was taken again from the dominant leg.

On day 1 of the treatment study, subjects reported to the blood sampling laboratory at 8 am following an overnight fast and a minimum of 12 hours since the last meat containing meal. Following catheterization and a basal blood sample, each subject followed the supplementation and blood sampling protocol described in Example 3. A dose of 10 milligrams per kilogram body weight of beta-alanine was administered at time 0 (9 am), 3 hours, and 6 hours.

On days 2-15, subjects continued to take three doses of 10 milligrams per kilogram body weight of beta-alanine.

In the morning of day 14, post-treatment isometric exercise tests were conducted on the dominant leg to determine MVC and endurance at 66% MVC relative to the 66% MVC measured on the day prior to treatment. In the afternoon, a muscle biopsy was taken of the vastus lateralis from close to the site of the biopsy taken on the day before treatment.

Figure 10:
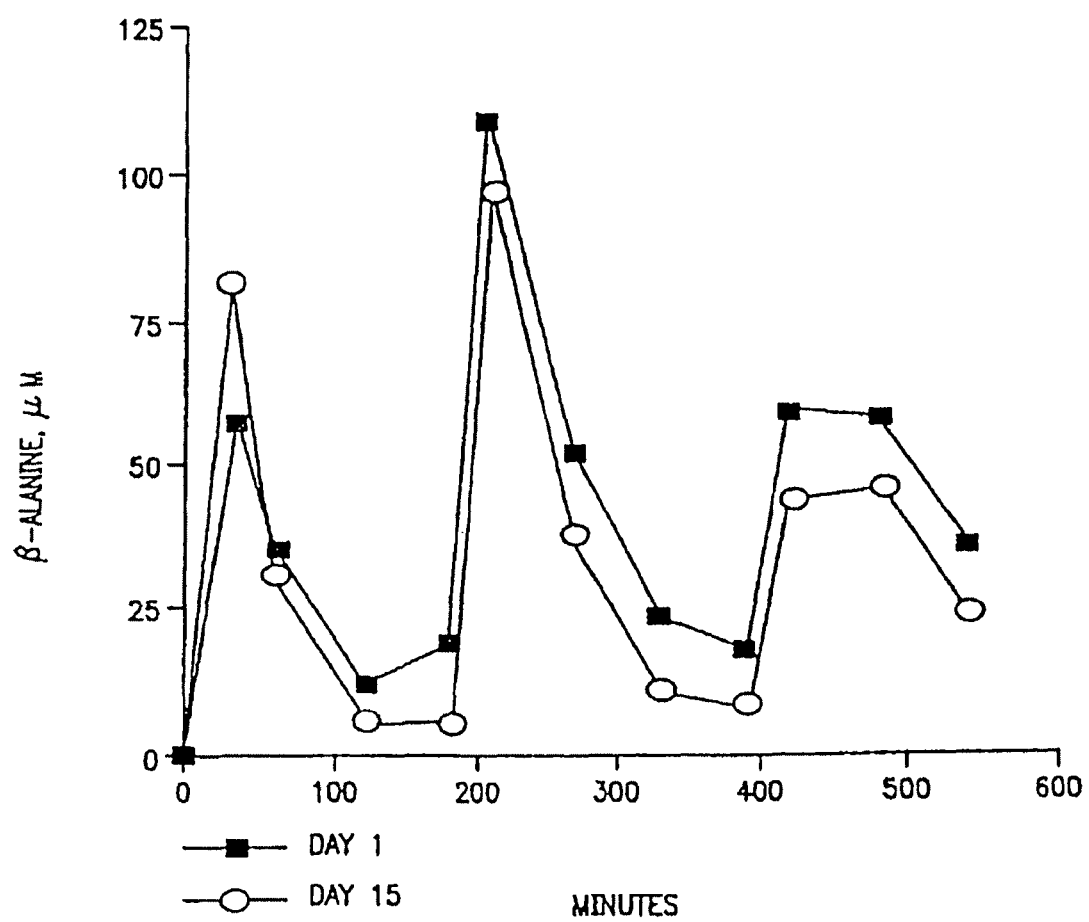
FIG. 10 is a graph depicting the mean changes in plasma beta-alanine over 9 hours following the oral ingestion of 10 milligrams per kilogram body weight of beta-alanine.
Figure 11:
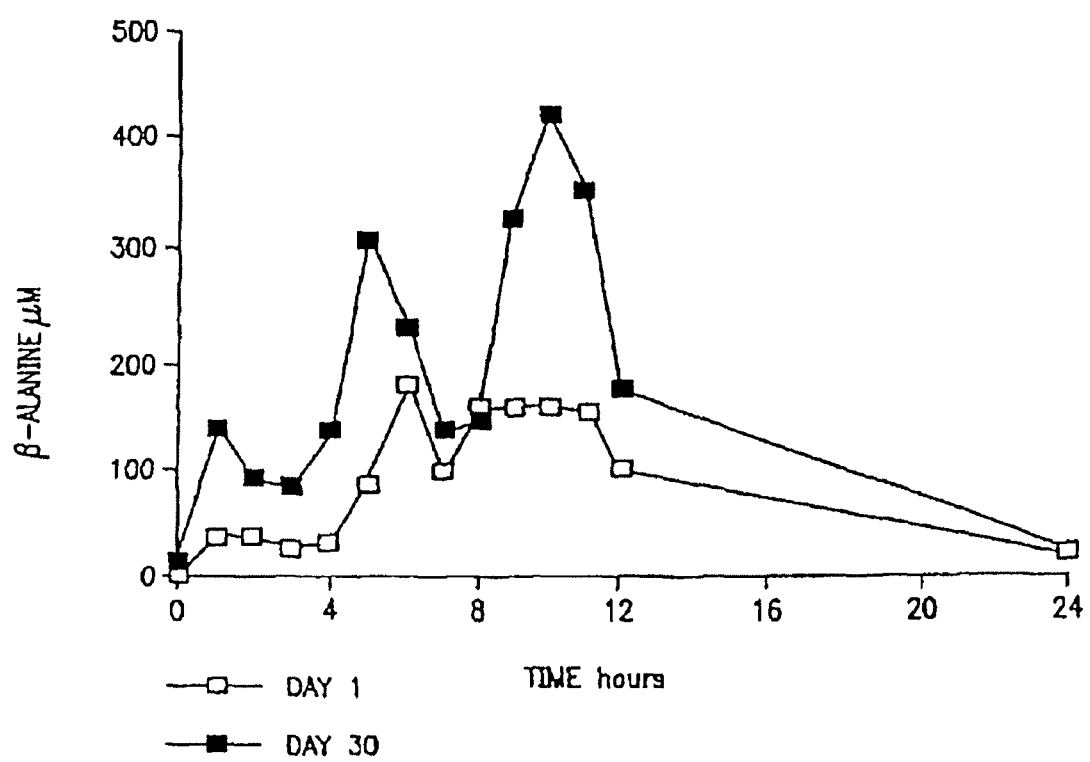
FIG. 11 is a graph depicting the mean (n=6) plasma beta-alanine concentration over the 24 hours of Day 1 and Day 30 of the treatment period.

On day 15, the procedures followed on day 1 were repeated to determine any overall shift in the plasma concentration profile of beta-alanine and taurine over the 15 days of supplementation. Mean changes in plasma beta-alanine over 9 hours following the oral ingestion of 10 milligrams per kilogram body weight of beta-alanine at 0, 3 and 6 hours on days 1 and 15 when dosing at 3×10 milligrams per kilogram body weight per day are shown in FIG. 10.

One additional test subject (number 7) followed the study, taking three doses 10 milligrams per kilogram body weight for 7 days followed by three doses of 20 milligrams per kilogram body weight for 7 days. No muscle biopsies were taken from this test subject.

There was no apparent change in the muscle carnosine content in the muscle of the six subjects biopsied. Changes in plasma taurine concentrations in the six subjects mirrored those of beta-alanine, as noted in Example 2.

Values from the MVC and endurance at 66% MVC measurements one day before treatment and after 14 days after treatment with three doses of 10 milligrams per kilogram body weight of beta-alanine are listed in Table 7. The mean endurance time at 66% MVC increased in 5 of the 6 subjects. An increase was also seen in subject 7 who had taken the higher dose.

TABLE 7

| Subject | MVC 1st try N | MVC 2nd try N | time @ 66% MVC 1st seconds | time @ 66% MVC 2nd seconds | time @ 66% MVC 3rd seconds | Total Contraction Time seconds |
|---|---|---|---|---|---|---|
| Pre | | | | | | |
| 1 | 784.5 | 821.9 | 48.53 | 29.03 | 23.78 | 100.83 |
| 2 | 814.4 | 886.2 | 48.40 | 26.03 | 16.90 | 91.33 |
| 3 | 984.9 | 970.4 | 38.15 | 26.03 | 16.78 | 80.95 |
| 4 | 714.6 | 740.4 | 89.03 | 56.15 | 45.65 | 190.83 |
| 5 | 1204.8 | 1217.2 | 37.65 | 27.64 | 21.53 | 86.83 |
| 6 | 722.4 | 716.8 | 46.78 | 29.40 | 21.90 | 98.08 |
| Pre mean | 870.9 | 892.1 | 51.4 | 32.4 | 24.3 | 108.1 |
| Pre SD | 190.6 | 184.6 | 19.1 | 11.7 | 10.8 | 41.2 |
| Post | | | | | | |
| 1 | 895.6 | 908.0 | 47.08 | 30.38 | 24.03 | 101.48 |
| 2 | 832.2 | 908.0 | 46.65 | 31.28 | 18.40 | 96.33 |
| 3 | 973.7 | 952.2 | 42.65 | 25.03 | 16.03 | 83.70 |
| 4 | 814.1 | 863.9 | 114.40 | 64.28 | 48.53 | 227.20 |
| 5 | 1246.6 | 1233.0 | 42.03 | 22.78 | 19.40 | 84.20 |
| 6 | 760.8 | 773.3 | 52.28 | 31.53 | 25.95 | 109.73 |
| Post mean | 920.5 | 939.7 | 57.5 | 34.2 | 25.4 | 117.1 |
| Post SD | 175.7 | 156.0 | 28.1 | 15.2 | 11.9 | 54.9 |
| Subject 7 | | | | | | |
| Pre | 858.18 | 861.54 | 54.0 | | | |
| Post | 792.54 | 851.41 | 62.0 | | | |

Example 5

The effect of 4 weeks of beta-alanine supplementation using two dosing regimens and an isomolar dose of L-carnosine (beta-alanylhistidine) administered over 4 weeks on the muscle carnosine content were investigated.

Fifteen male subjects, aged 20 to 29 years with no obvious signs of clinical disease and with heights and weights within the normal range, were recruited into the study (Table 8). All subjects participated in one or more sports and all ate a mixed diet containing variable amounts of meat. A record of each subject's approximate intake of meat during the course of the investigation was made.

TABLE 8

Summary of subjects' physical characteristics for each of the three treatment groups:

| Treatment | AGE Mean ± SD | HEIGHT Mean ± SD | MASS Mean ± SD |
|---|---|---|---|
| 1 | 24.4 ± 2.7 | 182.3 ± 7.5 | 80.0 ± 15.9 |
| 2 | 23.8 ± 1.9 | 180.9 ± 5.4 | 80.6 ± 8.6 |
| 3 | 24.0 ± 3.8 | 180.1 ± 3.8 | 80.4 ± 12.1 |

Five subjects were allocated to one of three treatment groups (1, 2, and 3). During the study, their diet was supplemented with either beta-alanine or carnosine as described in Table 9 (FIG. 17). The supplements were provided in soft gelatine capsules containing either 400 mg beta alanine or 500 mg carnosine.

In Group 1, beta-alanine was administered in 4 separate doses throughout the day (qid) at a steady rate for four weeks.

In Group 2, beta-alanine was administered as 8 separate doses throughout the day, rather than as 4 doses, in an attempt to maintain a more even increase in the blood-plasma concentration. In addition, the dose was increased progressively each week by 800 mg per day.

In Group 3, carnosine was administered at approximately the same isomolar dose as in Group 2, again divided into 8 doses. This treatment, therefore, contained approximately the same amount of beta-alanine as in Group 2, when hydrolyzed to its constituent amino acids.

The subjects took the supplements at the times indicated in Table 9 (FIG. 17). A single muscle biopsy of the vastus lateralis was taken before and at the end of the supplementation using the percutaneous needle biopsy procedure of Bergström (1962). In brief, the procedure involves the insertion of a hollow bored needle under local anesthetic and sterile conditions to obtain specimens around 20-40 mg containing approximately 100-700 muscle fibers. The skin and subcutaneous tissue is anesthetized with 1% lignocaine (avoiding contact with the muscle). An incision is made to the skin and deep fascia with a scalpel blade. The needle minus central rod is inserted into the muscle. The muscle bulk is pressed into a needle side-window. A sample is cut by ramming an inner, sharpened cylinder along the needle. The needle is removed and the central rod is used to evacuate the specimen. The wound is then closed.

Muscle samples from the subjects were frozen in liquid nitrogen, freeze-dried and analyzed for muscle carnosine and taurine contents by HPLC. Table 9 (FIG. 17) shows a breakdown of the dosing strategies employed in each of the three treatment groups. Results: There was no change in body mass in either beta-alanine or carnosine supplemented subjects.

Figure 12:
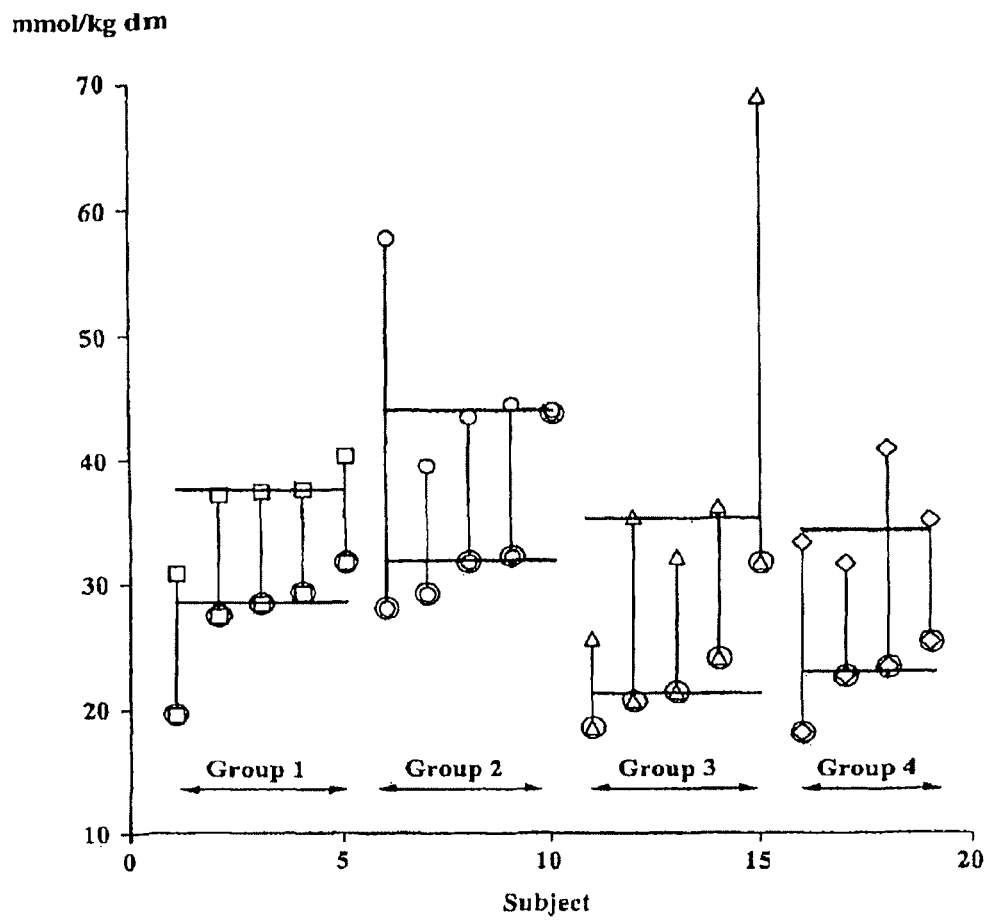
FIG. 12 is a graph depicting changes in muscle carnosine concentration pre and post treatment in different subjects. The red circles indicate the muscle concentrations prior to supplementation.
Figure 13:
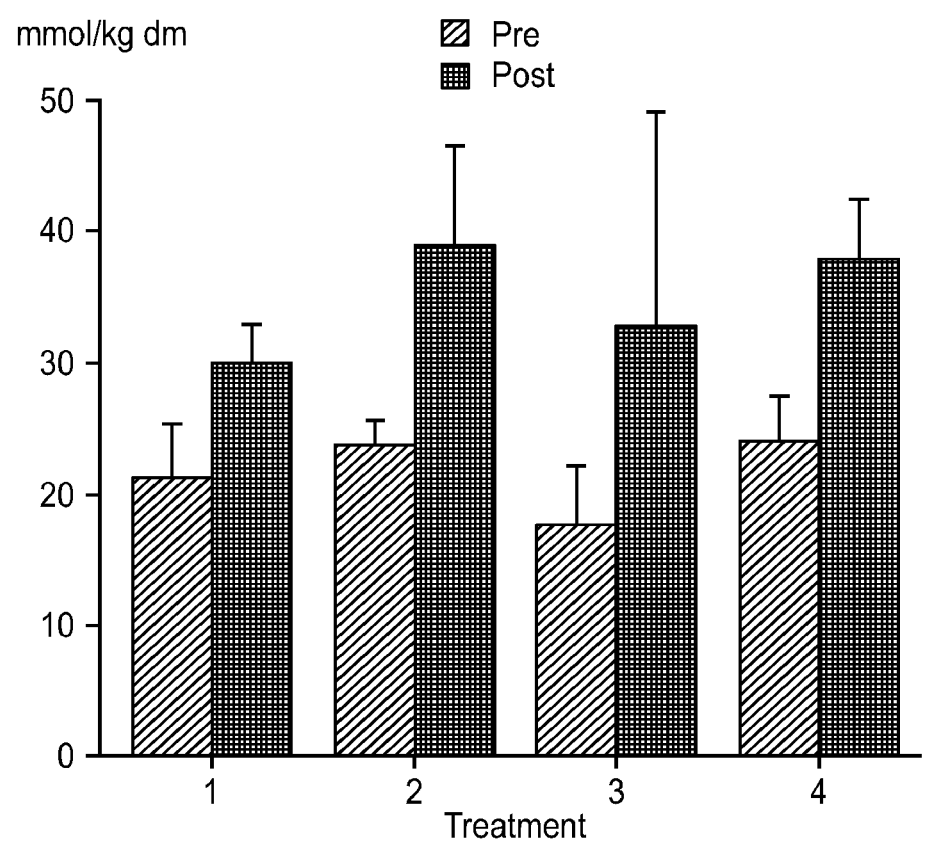
FIG. 13 is a graph depicting muscle concentration (mean+SD) of carnosine before and post supplementation in three different treatment groups.

Changes in Muscle Carnosine (Table 10 and FIGS. 12 and 13).

A significant increase in muscle carnosine content was recorded for the subjects in Groups 1 and 3. In Group 2, one subject (no. 10) with the highest initial carnosine content (initial carnosine content: 33.3 mmol/kg dry muscle) showed no change in his muscle carnosine content (post content: 33.7 mmol/kg dm). When this subject was deleted from Group 2, this group showed a significant increase of the same order as seen in the other Groups. Subject 10 was a medium to high consumer of meat and otherwise unremarkable.

Supplementation with either beta-alanine or carnosine at the same dose (Groups 2 and 3) appeared to be equally effective in increasing the muscle carnosine content.

The pattern of change is reminiscent of the changes observed with creatine loading and may suggest that there is a threshold which is quickly reached, with further supplementation having no further effect. In the case of subject 10, while not wishing to be bound by this theory, a threshold appears to have been reached even before the start of supplementation. However, there are exceptions to the notion of an upper threshold, notably subjects 6 (post supplementation carnosine: 45.9 mmol/kg dry muscle) and 15 (post supplementation carnosine: 68.9 mmol/kg dm). Subjects 6 and 15 were unremarkable in either their dietary patterns or participation in physical exercise.

Table 10 is a summary of data for carnosine muscle concentrations for treatment Groups 1 to 3. Treatment Group 2, in italics, is without subject 10 who did not exhibit an increase in muscle carnosine concentration. The initial carnosine concentration in subject 10 was the highest of all subjects and may have already been at an "upper threshold" level prior to supplementation.

TABLE 10

| | Treatment | | | |
|---|---|---|---|---|
| | 1<br>n = 5 | 2<br>n = 5 | *2*<br>*n = 4* | 3<br>n = 5 |
| Mean pre | 19.58 | 24.23 | *21.96* | 23.15 |
| SD pre | 3.71 | 5.27 | *1.64* | 5.07 |
| Mean post | 27.38 | 35.27 | *35.67* | 39.52 |
| SD post | 2.96 | 6.18 | *7.08* | 16.95 |
| Mean difference | 7.80 | 11.04 | *13.72* | 16.37 |
| SD difference | 0.81 | 9.20 | *8.08* | 12.06 |
| Sign | *** | ns | * | * |
| Min difference | 6.99 | 0.35 | *8.62* | 7.05 |
| Max difference | 9.08 | 25.77 | *25.77* | 37.39 |
| Mean % change | 42.1 | 51.6 | *64.2* | 65.8 |
| SD % change | 14.9 | 46.5 | *42.7* | 31.8 |
| Min % change | 31.5 | 1.1 | *41.0* | 38.2 |
| Max % change | 68.0 | 128.2 | *128.2* | 118.7 |

Figure 14:
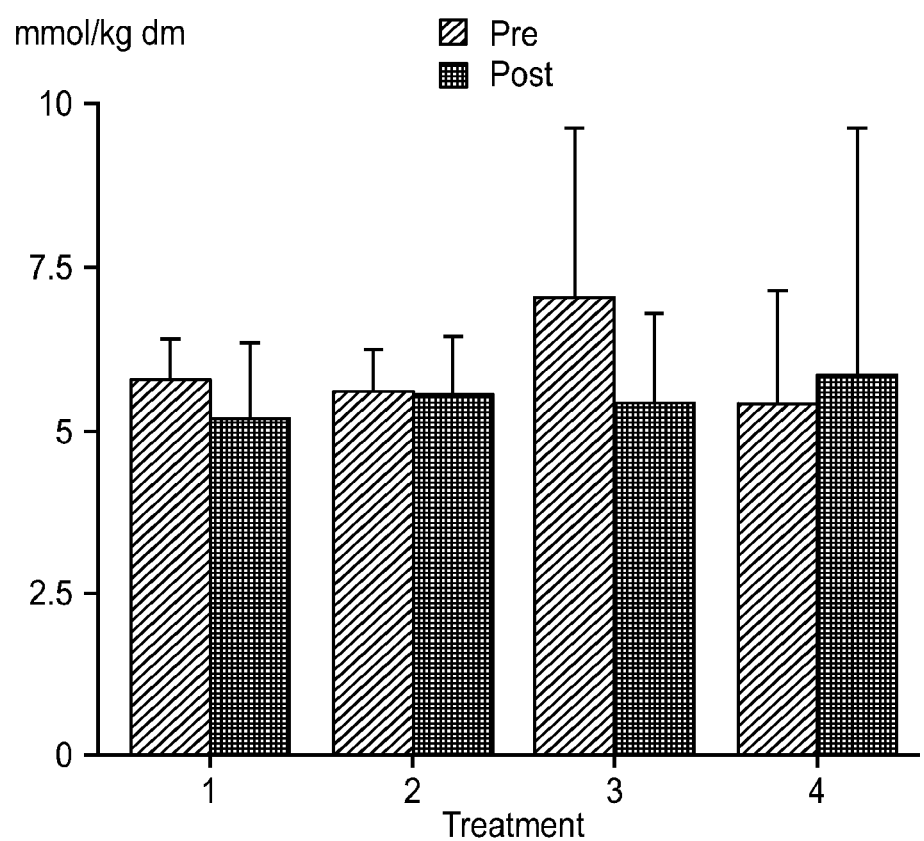
FIG. 14 is a graph depicting muscle concentration (mean+SD) of histidine before and post supplementation in three different treatment groups.

Changes in Muscle Beta-Alanine and Histidine (Table 11 and FIG. 14)

The muscle beta-alanine concentration was below the limit of detection (<0.2 mmol/kg dm) before and at the end of supplementation. In some subjects, a final dose of beta-alanine was taken within 1 to 2 hours of the final muscle biopsy.

There was no change in the muscle histidine concentration with supplementation with either beta-alanine or carnosine, the latter having the potential to release histidine into the general circulation. There was no decrease in the histidine concentration in response to the increased synthesis of carnosine (each mole requiring one mole of histidine).

Figure 15:
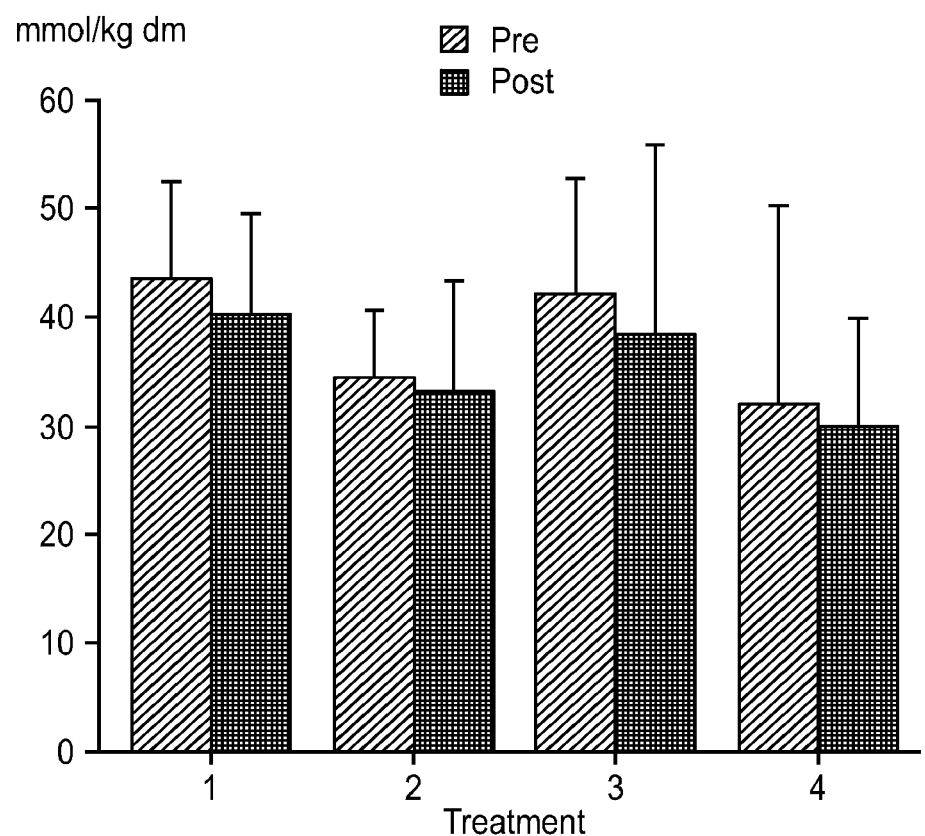
FIG. 15 is a graph illustrating data showing muscle concentration (mean+SD) of taurine before and post supplementation in four different treatment groups.
Figure 16:
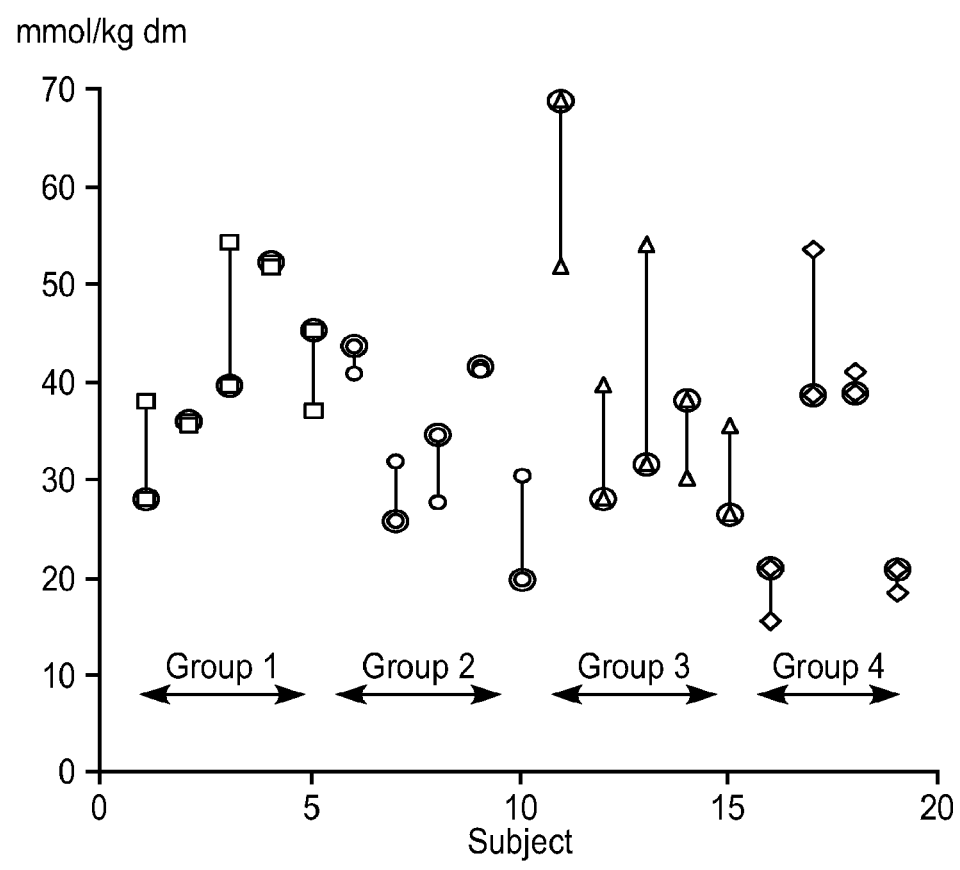
FIG. 16 is a graph illustrating data showing muscle concentration (mean+SD) of taurine before and post supplementation in different subjects.

Changes in Muscle Taurine (Table 12 and FIG. 15 and FIG. 16)

While beta-alanine at high concentrations may interfere with the uptake of taurine into tissues, previous observations show an increase in the plasma taurine concentration and loss of taurine in urine following both beta-alanine and carnosine administration, no loss of muscle taurine was noted in this study in any of the three Groups. Marked changes in the muscle taurine content occurred in some individuals, but both increases and decreases were observed. FIG. 15 is a graph illustrating data showing muscle concentration (mean+SD) of taurine before and post supplementation in four different treatment groups. FIG. 16 is a graph illustrating data showing muscle concentration (mean+SD) of taurine before and post supplementation in different subjects.

CONCLUSIONS

These studies demonstrate that the supplements of beta-alanine and carnosine of the invention have the potential to increase the muscle carnosine content. Based on the test results, they appear to be equally effective in increasing carnosine in tissue.

The changes in the muscle buffering capacity help maintain the intracellular microenvironment during intense exercise, countering the accumulation of $H^+$. As such, supplementation with beta-alanine or compounds delivering beta-alanine on ingestion may have a positive effect on exercise capacity in sports and those general daily activities leading to lactate accumulation. In view of the other chemical activities ascribed to carnosine (as an anti-oxidant and anti-glycating agent), an increase in carnosine concentration may have other beneficial effects apart from those arising from an increase in muscle buffering capacity.

Four weeks of supplementation did not result in any apparent loss of taurine in the muscles.

TABLE 11 summary data for histidine muscle concentrations in treatment Groups 1 to 3:

|  | Treatment | | |
| --- | --- | --- | --- |
|  | 1 n = 5 | 2 n = 5 | 3 n = 5 |
| mean pre | 5.76 | 5.56 | 7.01 |
| SD pre | 0.59 | 0.63 | 2.60 |
| mean post | 5.12 | 5.51 | 5.38 |
| SD post | 1.17 | 0.87 | 1.39 |
| mean diff | −0.64 | −0.05 | −1.63 |
| SD diff | 1.24 | 0.70 | 2.87 |
| Sign | ns | ns | ns |
| % change | −10.59 | −0.78 | −17.47 |
| SD % change | 21.65 | 12.65 | 29.56 |

TABLE 12

Summary data for taurine muscle concentrations in treatments Groups 1 to 3:

|  | Treatment | | |
| --- | --- | --- | --- |
|  | 1 n = 5 | 2 n = 5 | 3 n = 5 |
| Mean pre | 36.52 | 28.68 | 35.40 |
| SD pre | 7.77 | 5.29 | 8.92 |
| Mean post | 33.70 | 27.54 | 32.32 |
| SD post | 7.98 | 8.77 | 15.19 |
| Mean difference | −2.82 | −1.15 | −3.08 |
| SD difference | 7.96 | 6.04 | 13.61 |
| Sign | ns | ns | ns |
| % change | −6.28 | −4.46 | −7.66 |
| SD % change | 21.54 | 24.06 | 34.97 |

A number of embodiments of the invention have been described. Nevertheless, it will be understood that various modifications may be made without departing from the spirit and scope of the invention. Accordingly, other embodiments are within the scope of the following claims.

What is claimed is:

1. An improved method of delaying onset of muscle fatigue in a human comprising ingesting a human dietary supplement containing beta-alanine that is not part of a dipeptide, oligopeptide or polypeptide in an amount sufficient to increase beta-alanylhistidine synthesis in the muscle, wherein the improvement comprises increasing the amount of beta-alanine ingested in a 24 hour period for a period of time.

2. The method of claim 1, wherein the amount of beta-alanine ingested is increased to a maximum of 16 g.

3. The method of claim 1, wherein the improvement further comprises ingesting an amount of L-histidine to prevent loss of muscle histidine.

4. The method of claim 1, wherein the improvement further comprises decreasing the amount of beta-alanine ingested in a 24 hour period for a period of time following increasing the amount of beta-alanine ingested in a 24 hour period.

5. An improved method of increasing anaerobic working capacity of a muscle in a human comprising ingesting a human dietary supplement containing beta-alanine that is not part of a dipeptide, oligopeptide or polypeptide in an amount sufficient to increase beta-alanylhistidine synthesis in the muscle, wherein the improvement comprises increasing the amount of beta-alanine ingested in a 24 hour period for a period of time.

6. The method of claim 5, wherein the improvement further comprises ingesting an amount of L-histidine to prevent loss of muscle histidine.

7. The method of claim 5, wherein the amount of beta-alanine ingested is increased daily, every other day, weekly, every other week, or every day that the human participates in physical activity.

8. An improved method of increasing muscle strength in a human comprising ingesting a human dietary supplement containing beta-alanine that is not part of a dipeptide, oligopeptide or polypeptide in an amount sufficient to increase beta-alanylhistidine synthesis in the muscle, wherein the improvement comprises increasing the amount of beta-alanine ingested in a 24 hour period for a period of time.

9. The method of claim 8, wherein the improvement further comprises ingesting at least one of a creatine and a carbohydrate.

10. An improved method of increasing endurance of a muscle at submaximal force in a human comprising ingesting a human dietary supplement containing beta-alanine that is not part of a dipeptide, oligopeptide or polypeptide in an amount sufficient to increase beta-alanylhistidine synthesis in the muscle, wherein the improvement comprises increasing the amount of beta-alanine ingested in a 24 hour period for a period of time.

11. The method of claim 10, wherein the period of time is from 3 days to 8 weeks.

12. An improved method of delaying onset of muscle fatigue in a human comprising ingesting a human dietary supplement containing beta-alanine that is not part of a dipeptide, oligopeptide or polypeptide in an amount sufficient to increase beta-alanylhistidine synthesis in the muscle, wherein the improvement comprises ingesting a first daily dose of beta-alanine for a first period of time followed by a second daily dose of beta-alanine for a second period of time, wherein the first daily dose and second daily dose are different.

13. The method of claim 12, wherein the first daily dose of beta-alanine is from 3.5 to 16 g per 24 hour period.

14. The method of claim 12, wherein the second daily dose of beta-alanine is from 0.5 g to 3.5 g per 24 hour period.

15. An improved method of increasing anaerobic working capacity of a muscle in a human comprising ingesting a human dietary supplement containing beta-alanine that is not part of a dipeptide, oligopeptide or polypeptide in an amount sufficient to increase beta-alanylhistidine synthesis in the muscle, wherein the improvement comprises ingesting a first daily dose of beta-alanine for a first period of time followed by a second daily dose of beta-alanine for a second period of time, wherein the first daily dose and second daily dose are different.

16. The method of claim 15, wherein the improvement further comprises ingesting an amount of L-histidine to prevent loss of muscle histidine.

17. The method of claim 15, wherein the amount of L-histidine is 0.1 g to 16 g.

18. An improved method of increasing muscle strength in a human comprising ingesting a human dietary supplement containing beta-alanine that is not part of a dipeptide, oligopeptide or polypeptide in an amount sufficient to increase beta-alanylhistidine synthesis in the muscle, wherein the improvement comprises ingesting a first daily dose of beta-alanine for a first period of time followed by a second daily dose of beta-alanine for a second period of time, wherein the first daily dose and second daily dose are different.

19. The method of claim 18, wherein the first daily dose of beta-alanine is ingested daily, every other day, or every day that the human participates in physical activity.

20. An improved method of increasing endurance of a muscle at submaximal force in a human comprising ingesting a human dietary supplement containing beta-alanine that is not part of a dipeptide, oligopeptide or polypeptide in an amount sufficient to increase beta-alanylhistidine synthesis in the muscle, wherein the improvement comprises ingesting a first daily dose of beta-alanine for a period of time followed by a second daily dose of beta-alanine for a period of time, wherein the first daily dose and second daily dose are different.

21. The method of claim 1, wherein the method excludes administration of histidine.

22. The method of claim 5, wherein the method excludes administration of histidine.

23. The method of claim 8, wherein the method excludes administration of histidine.

24. The method of claim 10, wherein the method excludes administration of histidine.

25. The method of claim 12, wherein the method excludes administration of histidine.

26. The method of claim 15, wherein the method excludes administration of histidine.

27. The method of claim 18, wherein the method excludes administration of histidine.

28. The method of claim 20, wherein the method excludes administration of histidine.

* * * * *